(12) United States Patent
Marillonnet et al.

US008093458B2

(10) Patent No.: US 8,093,458 B2
(45) Date of Patent: Jan. 10, 2012

(54) BIOLOGICALLY SAFE TRANSIENT PROTEIN EXPRESSION IN PLANTS

(75) Inventors: Sylvestre Marillonnet, Halle (DE); Carola Engler, Halle (DE); Stefan Mühlbauer, Freising (DE); Stefan Herz, Munich (DE); Stefan Werner, Halle (DE); Victor Klimyuk, Halle (DE); Yuri Gleba, Halle (DE)

(73) Assignee: Icon Genetics GmbH, München (DE)

( * ) Notice: Subject to any disclaimer, the term of this patent is extended or adjusted under 35 U.S.C. 154(b) by 1007 days.

(21) Appl. No.: 11/631,719

(22) PCT Filed: Jul. 7, 2005

(86) PCT No.: PCT/EP2005/007361
§ 371 (c)(1),
(2), (4) Date: Nov. 9, 2007

(87) PCT Pub. No.: WO2006/003018
PCT Pub. Date: Jan. 12, 2006

(65) Prior Publication Data
US 2008/0057563 A1    Mar. 6, 2008

Related U.S. Application Data

(60) Provisional application No. 60/593,454, filed on Jan. 15, 2005.

(30) Foreign Application Priority Data

Jul. 7, 2004   (EP) .................................... 04016011

(51) Int. Cl.
*C12N 15/82*   (2006.01)
*C12N 15/63*   (2006.01)
*C12N 15/09*   (2006.01)

(52) U.S. Cl. ..... 800/294; 800/278; 800/288; 435/320.1; 435/468; 536/23.1; 536/23.2

(58) Field of Classification Search ........................ None
See application file for complete search history.

(56) References Cited

U.S. PATENT DOCUMENTS

| 4,190,495 | A | 2/1980 | Curtiss, III | |
| 6,323,396 | B1* | 11/2001 | Dirks et al. | ............. 800/294 |
| 6,632,980 | B1 | 10/2003 | Yadav et al. | |
| 6,740,526 | B1 | 5/2004 | Curtis | |
| 2002/0076751 | A1* | 6/2002 | Hattori et al. | ............. 435/69.1 |
| 2007/0044170 | A1 | 2/2007 | Marillonnet et al. | |

FOREIGN PATENT DOCUMENTS

| WO | WO 94/16089 A1 | 7/1994 |
| WO | WO 99/22003 A1 | 5/1999 |
| WO | WO 00/53780 A2 | 9/2000 |
| WO | WO 01/38512 A2 | 5/2001 |
| WO | WO 02/088369 A1 | 11/2002 |
| WO | WO 02/097080 A2 | 12/2002 |
| WO | WO 2005/049839 A2 | 6/2005 |

OTHER PUBLICATIONS

Marillonnet et al 2004 PNAS 10:6852-6857, provided by Applicant.*
Gleba et al 2004 Current Opinion in Plant Biology 7:182-188, provided by Applicant.*
Chakrabarty, R., et al., "*Agrobacterium*-mediated Transformation of Cauliflower: Optimization of Protocol and Development of Bt-transgenic Cauliflower,"*J. Biosci.*, 2002, pp. 495-502, vol. 27(5), Indian Academy of Sciences.
Citovsky, V., et al., "Nuclear Localization of *Agrobacterium* VirE2 Protein in Plant Cells," *Science*, 1992, pp. 1802-1805, vol. 256.
Collens, J., et al., "Development of Auxotrophic *Agrobacterium tumefaciens* for Gene Transfer in Plant Tissue Culture," *Biotechnol. Prog.*, 2004, pp. 890-896, vol. 20.
Gleba, Y., et al., "Engineering Viral Expression Vectors for Plants: the 'Full Virus' and the 'Deconstructed Virus' Stragegies," *Current Opinion in Plant Biology*, 2004, pp. 182-188, vol. 7.
Haseloff, J., et al., "Removal of a Cryptic Intron and Subcellular Localization of Green Fluorescent Protein are Required to Mark Transgenic *Arabidopsis* Plants Brightly," *Proc. Natl. Acad. Sci. USA*, 1997, pp. 2122-2127, vol. 94.
Hodges, L., et al.,"*Agrobacterium rhizogenes* GALLS Protein Substitutes for *Agrobacterium tumefaciens* Single-Stranded DNA-Binding Protein VirE2," *Journal of Bacteriology*, 2004, pp. 3065-3077, vol. 186(10).
Koziel, M., et al., "Optimizing Expression of Transgenes with an Emphasis on Post-transcriptional Events," *Plant Molecular Biology*, 1996, pp. 393-405, vol. 32.
Lee, et al., "pSa Causes Oncogenic Suppression of *Agrobacterium* by Inhibiting VirE2 Protein Export," *Journal of Bacteriology*, 1999, pp. 186-196, vol. 181(1).
Mallory, A., et al., "The Amplicon-plus System for High-level Expression of Transgenes in Plants," *Nature Biotechnology*, 2002, pp. 622-625, vol. 20.
Marillonnet, S., et al., "In planta Engineering of Viral RNA Replicons: Efficient Assembly by Recombination of DNA Modules Delivered by *Agrobacterium*," *Proc. Natl. Acad. Sci. USA*, 2004, pp. 6852-6857, vol. 101(18).

(Continued)

*Primary Examiner* — Brent T Page
(74) *Attorney, Agent, or Firm* — Alston & Bird LLP

(57) ABSTRACT

A process of producing a protein of interest by expression of said protein of interest from a sequence of interest in a plant or in plant leaves, comprising: (a) transfecting said plant or said plant leaves by infiltrating said plant or said plant leaves with an *Agrobacterium* strain in the presence of a complementing factor, said *Agrobacterium* strain containing in T-DNA a heterologous DNA sequence having a sequence portion encoding a replicon, wherein said sequence encoding a replicon contains sequences necessary for replicon function of said replicon, said sequences being derived from a plant virus, and said sequence of interest to be expressed from said replicon, (b) optionally isolating said protein of interest from said plant or said plant leaves infiltrated in step (a), wherein said *Agrobacterium* strain is provided with a first genetic modification rendering said *Agrobacterium* strain defective for transfecting organisms with said T-DNA in the absence of said complementing factor.

36 Claims, 33 Drawing Sheets

OTHER PUBLICATIONS

Rose, A.B., "Requirements for Intron-mediated Enhancement of Gene Expression in *Arabidopsis*," *RNA*, 2002, pp. 1444-1453, vol. 8.

Simpson, C., et al., "Expression of a Heterologous Gene can be Improved by Mutation of Cryptic Splice Sites," *Journal of Experimental Botany*, 1995, pp. 38, vol. 46(Suppl.).

Torres, B., et al., "A Dual Lethal System to Enhance Containment of Recombinant Micro-Organisms," *Microbiology*, 2003, pp. 3595-3601, vol. 149.

Ward, D.V. and P.C. Zambryski, "The Six Functions of *Agrobacterium* VirE2," *Proc. Natl. Acad. Sci. USA*, 2001, pp. 385-385, vol. 98(2).

Farrand, S., et al., "The *tra* Region of the Nopaline-Type Ti Plasmid is a Chimera with Elements Related to the Transfer Systems of RSF1010, RP4, and F," *Journal of Bacteriology*, 1996, pp. 4233-4247, vol. 178(14).

*Abstracts of Research Outcomes in Shizuoka Prefectural Agricultural Experiment Station*, 1999, vol. 43, pp. 263-264.

Baulcombe et al., "Jellyfish green flouroscent protein as a reporter for virus infections." *The Plant Journal*, 1995, vol. 7(6), pp. 1045-1053

Sakharkar et al., "Exlnt: an Exon/Intron database," *Nucleic Acids Research*, 2000, vol. 28(1), pp. 191-192.

Turpen et al., "Transfection of whole plants from wounds inoculated with *Agrobacterium tumefaciens* containing cDNA of tobacco mosaic virus," *Journal of Virological Methods*, 1993, vol. 42, pp. 227-240.

Genbank Report for Accession No. Z29370; Aug. 24, 2005.

* cited by examiner

Fig. 14C

SEQUENCE LISTING

<160> NUMBER OF SEQ ID NOS: 22

<210> SEQ ID NO 1
<211> LENGTH: 538
<212> TYPE: DNA
<213> ORGANISM: Artificial Sequence
<220> FEATURE:
<223> OTHER INFORMATION: NcoI-EcoRI fragment of pICH14833

<400> SEQUENCE: 1

```
ccatggacaa agtgataaag gcagctttt  gtggagacga tagcctgatt tacattccta      60
aaggtttaga cttgcctgat attcaggcgg gcgcgaacct catgtggaac ttcgaggcca     120
aactcttcag gaagaagtat ggttacttct gtggtcgtta tgttattcac catgatagag     180
gagccattgt gtattacgat ccgcttaaac taatatctaa gttaggttgt aaacatatta     240
gagatgttgt tcacttagaa gagttacgcg agtctttgtg tgatgtagct agtaacttaa     300
ataattgtgc gtattttca cagttagatg aggccgttgc cgaggttcat aagaccgcgg      360
taggcggttc gtttgctttt tgtagtataa ttaagtattt gtcagataag agattgttta     420
gagatttgtt ctttgtttga taatgtcgat agtctcgtac gaacctaagg tgagtgattt     480
cctcaatctt tcgaagaagg aagagatctt gccgaaggct ctaacgaggt tagaattc       538
```

<210> SEQ ID NO 2
<211> LENGTH: 636
<212> TYPE: DNA
<213> ORGANISM: Artificial Sequence
<220> FEATURE:
<223> OTHER INFORMATION: part of pICH15466

<400> SEQUENCE: 2

```
ggagataacc tgagcttctt cttccataat gagagcactc tcaattacac ccacagcttc      60
agcaacatca tcaagtacgt gtgcaagacg ttcttccctg ctagtcaacg cttcgtgtac     120
cacaaggagt tcctggtcac tagagtcaac acttggtact gcaagttcac gagagtggat     180
acgttcactc tgttccgtgg tgtgtaccac aacaatgtgg attgcgaaga gttttacaag     240
gctatggacg atgcgtggca ctacaaaaag acgttagcaa tgcttaatgc cgagaggacc     300
atcttcaagg ataacgctgc gttaaacttt tggttcccga agtgagagaa catggttatc     360
gtccctctct ttgacgcttc tatcacaact ggtaggatgt ctaggagaga ggttatggtg     420
aacaaggact tcgtctacac ggtcctaaat cacatcaaga cctatcaagc taaggcactg     480
acgtacgcaa acgtgctgag cttcgtggag tctattaggt ctagagtcat aattaacggt     540
gtcactgcca ggtctgaatg ggacacagac aaggcaattc taggtccatt agcaatgaca     600
ttcttcctga tcacgaagct gggtcatgtg caagat                               636
```

<210> SEQ ID NO 3
<211> LENGTH: 297
<212> TYPE: DNA
<213> ORGANISM: Artificial Sequence
<220> FEATURE:
<223> OTHER INFORMATION: part of pICH15900

<400> SEQUENCE: 3

```
gcggacgata cgtgatccac catgatagag gagccattgt gtattacgat ccgcttaaac      60
taatatctaa gctcggctgc aagcacatca gagacgtcgt gcacttagaa gagttacgcg     120
agtctttgtg cgacgtagct agtaacttga acaactgcgc ctacttctca cagttagatg     180
```

| aggccgttgc tgaggtccac aagactgcgg tcggaggctc cttcgcgttc tgtagcatca | 240 |
| tcaaatactt gtcagacaag aggctgttca gggacctgtt cttcgtctga gttgacg | 297 |

<210> SEQ ID NO 4
<211> LENGTH: 1419
<212> TYPE: DNA
<213> ORGANISM: Artificial Sequence
<220> FEATURE:
<223> OTHER INFORMATION: part of pICH15025

<400> SEQUENCE: 4

| cccgagctat actgtacctt cgccgaccga ttggtactac agtacaagaa ggcggaggag | 60 |
| ttccaatcgt gtgatctttc caaacctcta gaagagtcag agaagtacta caacgcatta | 120 |
| tccgagctat cagtgcttga gaatctcgac tcttttgact tagaggcgtt taagacttta | 180 |
| tgtcagcaga agaatgtgga cccggatatg gcagcaaagg taaatcctgg tccacacttt | 240 |
| tacgataaaa acacaagatt ttaaactatg aactgatcaa taatcattcc taaaagacca | 300 |
| cacttttgtt ttgtttctaa agtaatttttt actgttataa caggtggtcg tagcaatcat | 360 |
| gaagtcagaa ttgacgttgc ctttcaagaa acctacagaa gaggaaatct cggagtcgct | 420 |
| aaaaccagga gaggggtcgt gtgcagagca taaggaagtg ttgagcttac aaaatgatgc | 480 |
| tccgttcccg tgtgtgaaaa atctagttga aggttccgtg ccggcgtatg gaatgtgtcc | 540 |
| taagggtggt ggtttcgaca aattggatgt ggacattgct gatttccatc tcaagagtgt | 600 |
| agatgcagtt aaaaagggaa ctatgatgtc tgcggtgtac acagggtcta tcaaagttca | 660 |
| acaaatgaag aactacatag attacttaag tgcgtcgctg gcagctacag tctcaaacct | 720 |
| ctgcaaggta agaggtcaaa aggtttccgc aatgatccct cttttttttgt ttctctagtt | 780 |
| tcaagaattt gggtatatga ctaacttctg agtgttcctt gatgcatatt tgtgatgaga | 840 |
| caaatgtttg ttctatgttt taggtgctta gagatgttca cggcgttgac ccagagtcac | 900 |
| aggagaaatc tggagtgtgg gatgttagga gaggacgttg gttacttaaa cctaatgcga | 960 |
| aaagtcacgc gtggggtgtg gcagaagacg ccaaccacaa gttggttatt gtgttactca | 1020 |
| actgggatga cggaaagccg gtttgtgatg agacatggtt cagggtggcg gtgtcaagcg | 1080 |
| attccttgat atattcggat atgggaaaac ttaagacgct cacgtcttgc agtccaaatg | 1140 |
| gtgagccacc ggagcctaac gccaaagtaa ttttggtcga tggtgttccc ggttgtggaa | 1200 |
| aaacgaagga gattatcgaa aaggtaagtt ctgcatttgg ttatgctcct tgcattttag | 1260 |
| gtgttcgtcg ctcttccatt tccatgaata gctaagattt ttttctctg cattcattct | 1320 |
| tcttgcctca gttctaactg tttgtggtat ttttgtttta attattgcta caggtaaact | 1380 |
| tctctgaaga cttgattta gtccctggga aggaagctt | 1419 |

<210> SEQ ID NO 5
<211> LENGTH: 1159
<212> TYPE: DNA
<213> ORGANISM: Artificial Sequence
<220> FEATURE:
<223> OTHER INFORMATION: part of pICH15034

<400> SEQUENCE: 5

| ctgcaggtaa atattggat gccagacgat attctttctt ttgatttgta acttttttcct | 60 |
| gtcaaggtcg ataaatttta tttttttttgg taaaaggtcg ataattttttt tttggagcca | 120 |
| ttatgtaatt ttcctaatta actgaaccaa aattatacaa accaggtttg ctggaaaatt | 180 |
| tggttgcaat gatcaaaaga aacatgaatg cgccggattt gacagggaca attgacattg | 240 |

```
aggatactgc atctctggtg gttgaaaagt tttgggattc gtatgttgac aaggaattta      300
gtggaacgaa cgaaatgacc atgacaaggg agagcttctc caggtaagga cttctcatga      360
atattagtgg cagattagtg ttgttaaagt ctttggttag ataatcgatg cctcctaatt      420
gtccatgttt tactggtttt ctacaattaa aggtggcttt cgaaacaaga gtcatctaca      480
gttggtcagt tagcggactt taactttgtg gatttgccgg cagtagatga gtacaagcat      540
atgatcaaga gtcaaccaaa gcaaaagtta gacttgagta ttcaagacga atatcctgca      600
ttgcagacga tagtctacca ttcgaaaaag atcaatgcga ttttcggtcc aatgttttca      660
gaacttacga ggatgttact cgaaaggatt gactcttcga agtttctgtt ctacaccaga      720
aagacacctg cacaaataga ggacttcttt tctgacctag actcaaccca ggcgatggaa      780
attctggaac tcgacatttc gaagtacgat aagtcacaaa acgagttcca ttgtgctgta      840
gagtacaaga tctgggaaaa gttaggaatt gatgagtggc tagctgaggt ctggaaacaa      900
ggtgagttcc taagttccat ttttttgtaa tccttcaatg ttattttaac ttttcagatc      960
aacatcaaaa ttaggttcaa ttttcatcaa ccaaataata tttttcatgt atatataggt     1020
cacagaaaaa cgaccttgaa agattatacg gccggaatca aaacatgtct ttggtatcaa     1080
aggaaaagtg gtgatgtgac aacctttatt ggtaatacca tcatcattgc cgcatgtttg     1140
agctcaatga tccccatgg                                                  1159

<210> SEQ ID NO 6
<211> LENGTH: 774
<212> TYPE: DNA
<213> ORGANISM: Artificial Sequence
<220> FEATURE:
<223> OTHER INFORMATION: fragment of pICH15477

<400> SEQUENCE: 6
gttttagttt tattgcaaca acaacaacaa attacaataa caacaaacaa aatacaaaca       60
acaacaacat ggcacaattt caacaaacaa ttgacatgca aactctccaa gccgctgcgg      120
gacgcaacag cttggtgaat gatttggcat ctcgtcgcgt ttacgataat gcagtcgagg      180
agctgaatgc tcgttccaga cgtcccaagg taaaacaaca tttcattcac atatatgaat      240
acttttgtca ttgagtacga agaagacact tactacttgt tgatgaaagt ttccgccttt      300
atacttatct atatcatttt catcatttca aactagtatg aaattaggtg atgtttatat      360
gatatcatgg aacattaatc tatagggaaa ctgttttgag ttagttttgt ataatatttt      420
tccctgtttg atgttaggtt catttctcca aggcagtgtc tacggaacag acactgattg      480
caacaaacgc atatccggag ttcgagattt cctttactca tacgcaatcc gctgtgcact      540
ccttggccgg aggccttcgg tcacttgagt tggagtatct catgatgcaa gttccgttcg      600
gctctctgac ctacgacatc ggcggaaact tctccgcgca cctcttcaaa ggtaattttc      660
tttctctact caattttctc caagatccaa tatttgaaga ctgatctata gttaaaatta      720
atctctactc cattcttgtt acctcaggtc gcgattacgt tcactgctgc atgc            774

<210> SEQ ID NO 7
<211> LENGTH: 16
<212> TYPE: DNA
<213> ORGANISM: Artificial Sequence
<220> FEATURE:
<223> OTHER INFORMATION: spacer in construct pICH8543

<400> SEQUENCE: 7
taatcgataa ctcgag                                                       16
```

```
<210> SEQ ID NO 8
<211> LENGTH: 17
<212> TYPE: PRT
<213> ORGANISM: Artificial Sequence
<220> FEATURE:
<223> OTHER INFORMATION: interferon sequence portion

<400> SEQUENCE: 8

Leu Leu Val Ala Leu Leu Val Leu Ser Cys Lys Ser Ser Cys Ser Val
1               5                   10                  15

Gly

<210> SEQ ID NO 9
<211> LENGTH: 26
<212> TYPE: DNA
<213> ORGANISM: Artificial Sequence
<220> FEATURE:
<223> OTHER INFORMATION: PCR primer

<400> SEQUENCE: 9
gaggatccaa cgtttaggag aaccag                                        26

<210> SEQ ID NO 10
<211> LENGTH: 33
<212> TYPE: DNA
<213> ORGANISM: Artificial Sequence
<220> FEATURE:
<223> OTHER INFORMATION: PCR primer

<400> SEQUENCE: 10
ttggtctcac ggtatacgca cactgaacat gcg                                33

<210> SEQ ID NO 11
<211> LENGTH: 28
<212> TYPE: DNA
<213> ORGANISM: Artificial Sequence
<220> FEATURE:
<223> OTHER INFORMATION: PCR primer

<400> SEQUENCE: 11
ttggtctcaa ccggtttccg tttgtctc                                      28

<210> SEQ ID NO 12
<211> LENGTH: 28
<212> TYPE: DNA
<213> ORGANISM: Artificial Sequence
<220> FEATURE:
<223> OTHER INFORMATION: PCR primer

<400> SEQUENCE: 12
acgtctagag atcgcgttcc agaccaac                                      28

<210> SEQ ID NO 13
<211> LENGTH: 29
<212> TYPE: DNA
<213> ORGANISM: Artificial Sequence
<220> FEATURE:
<223> OTHER INFORMATION: PCR primer

<400> SEQUENCE: 13
ctgaattcag gcaaacgcac cgtgagatg                                     29

<210> SEQ ID NO 14
<211> LENGTH: 26
<212> TYPE: DNA
<213> ORGANISM: Artificial Sequence
```

```
<220> FEATURE:
<223> OTHER INFORMATION: PCR primer

<400> SEQUENCE: 14
tcaccatggg tcacgcggca ctcctg                                       26

<210> SEQ ID NO 15
<211> LENGTH: 27
<212> TYPE: DNA
<213> ORGANISM: Artificial Sequence
<220> FEATURE:
<223> OTHER INFORMATION: PCR primer

<400> SEQUENCE: 15
tcaccatggc ccaggcccgg cgtgaac                                      27

<210> SEQ ID NO 16
<211> LENGTH: 29
<212> TYPE: DNA
<213> ORGANISM: Artificial Sequence
<220> FEATURE:
<223> OTHER INFORMATION: PCR primer

<400> SEQUENCE: 16
acatctagat gccggcatcg aagatgttg                                    29

<210> SEQ ID NO 17
<211> LENGTH: 31
<212> TYPE: DNA
<213> ORGANISM: Artificial Sequence
<220> FEATURE:
<223> OTHER INFORMATION: PCR primer

<400> SEQUENCE: 17
ttggtctcac cggccgatag ccaaaaactg c                                 31

<210> SEQ ID NO 18
<211> LENGTH: 26
<212> TYPE: DNA
<213> ORGANISM: Artificial Sequence
<220> FEATURE:
<223> OTHER INFORMATION: PCR primer

<400> SEQUENCE: 18
gagctagctc cgtccttcac ctgggc                                       26

<210> SEQ ID NO 19
<211> LENGTH: 29
<212> TYPE: DNA
<213> ORGANISM: Artificial Sequence
<220> FEATURE:
<223> OTHER INFORMATION: PCR primer

<400> SEQUENCE: 19
ttggtctcgc cggccaaact ccggtttgc                                    29

<210> SEQ ID NO 20
<211> LENGTH: 29
<212> TYPE: DNA
<213> ORGANISM: Artificial Sequence
<220> FEATURE:
<223> OTHER INFORMATION: PCR primer

<400> SEQUENCE: 20
atgggccctt cgaacgcaat tcctgttgc                                    29
```

```
<210> SEQ ID NO 21
<211> LENGTH: 22
<212> TYPE: DNA
<213> ORGANISM: Artificial Sequence
<220> FEATURE:
<223> OTHER INFORMATION: PCR primer

<400> SEQUENCE: 21
cctcggccgc gaacggcctc ac                                              22

<210> SEQ ID NO 22
<211> LENGTH: 32
<212> TYPE: DNA
<213> ORGANISM: Artificial Sequence
<220> FEATURE:
<223> OTHER INFORMATION: PCR primer

<400> SEQUENCE: 22
ctacggccgc tgacagctaa aacaattcat cc                                   32
```

BIOLOGICALLY SAFE TRANSIENT PROTEIN EXPRESSION IN PLANTS

FIELD OF THE INVENTION

The present invention relates to a biologically safe process of recombinant protein production in plants using transient expression based on plant viral vectors delivered into target plants by Agrobacteria. The invention also relates to a process of expressing a sequence of interest in a target host plants or plant leaves. The invention describes the use of *Agrobacterium*-mediated delivery of viral vectors providing for high yield, large scale production of a protein of interest in whole plant or plant parts. The process of the invention confines transient expression via *Agrobacterium*-mediated delivery to said plant host, whereas transformation of undesired organisms is controlled. The invention further relates to biologically safe Agrobacteria for expressing a sequence of interest in a plant or in plant leaves. The invention provides for high-yield industrial protein production in plants with increased biosafety features.

BACKGROUND OF THE INVENTION

Today, plant biotechnology relies on two approaches for delivery and expression of foreign genes in plants: stable genetic transformation and transient expression. The last one can be built on agro-infiltration or viral infection (for review see: Fischer et al., 1999, *Biotechnol. Appl. Biochem.*, 30, 113-116). Transient expression can be achieved by agroinfiltrating plant tissue with a standard expression cassette under control of a constitutive, for example 35S promoter to drive expression of gene of interest (Vaquero et al., 1999, *Proc. Natl. Acad. Sci. USA.*, 96, 11128-11133) or, at larger scale, by transfecting a plant with viral vectors. Usually agro-infiltration does not provide for high yield, but in combination with post-transcriptional gene silencing (PTGS) suppressors, like p19 or HcPro the protein expression level can be increased up to 50-folds (Voinnet et al., 2003, *Plant J.*, 33, 549-556). Still it is far below the biological limits that can be achieved with the help of viral expression systems (Marillonnet et al., 2004, *Proc. Natl. Acad. Sci. USA*, 101, 6852-6857). A description of a bioreactor based on the use of agro-infiltration for transient expression of a recombinant protein of interest in plant tissue is provided in U.S. Pat. No. 6,740,526. However, this patent is silent on how to improve the yield of the protein to be expressed, i.e. it does not go beyond other known processes in the field (Vaquero et al., 1999, *Proc. Natl. Acad. Sci. USA.*, 96, 11128-11133). A more powerful approach for transient expression is the use of viral vectors. It was shown that TMV-based expression of a reporter gene (GFP or DsRed) can reach the biological yield limits of the system, producing several milligrams of recombinant protein per gram of fresh leaf biomass (Marillonnet et al., 2004, *Proc. Natl. Acad. Sci. USA*, 101, 6852-6857). The relative yield in such system can reach up to 80% of TSP, thus significantly facilitating and reducing the cost of downstream processing. Such a high relative yield is possible due to virus-induced shut-off of host protein biosynthesis.

It is evident that viral vectors can provide for higher expression levels than conventional vectors used in agro-infiltration (for review see: Porta & Lomonossoff, 1996, *Mol Biotechnol.*, 5, 209-221; Yusibov et al., 1999, *Curr. Top. Microbiol. Immunol.*, 240, 81-94) and are a powerful tool for functional genomics studies (Dalmay et al., 2000, *Plant Cell*, 12, 369-379; Ratcliff et al., 2001, *Plant J.*, 25, 237-245; Escobar et al., 2003, *Plant Cell*, 15, 1507-1523). Numerous publications and patents in the field describe systems based on DNA and RNA viral vectors (Kumagai et al., 1994, *Proc. Natl. Acad. Sci. USA*, 90, 427-430; Mallory et al., 2002, *Nature Biotechnol.* 20, 622-625; Mor et al., 2003, *Biotechnol. Bioeng.*, 81; 430-437; U.S. Pat. No. 5,316,931; U.S. Pat. No. 5,589,367; U.S. Pat. No. 5,866,785; U.S. Pat. No. 5,491,076; U.S. Pat. No. 5,977,438; U.S. Pat. No. 5,981,236; WO02088369; WO02097080; WO9854342). The existing viral vector systems are usually restricted to a narrow host range in terms of their best performance and even the expression level of such vectors in their most favourable host is far below the upper biological limits of the system. An important issue of virus-based systems is the method of delivery of the viral replicon to a plant cell. The most broadly applied method of delivery for large-scale production (simultaneous production in many plants, e.g. in a farm field or a greenhouse) is the use of infectious copies of RNA viral vectors (Kumagai et al., 1995, *Proc. Natl. Acad. Sci. USA*, 92, 1679-1683). Because of a relatively high tendency of recombinant viral RNA vectors to lose the heterologous inserts during cycles of their replication, the method requires transcription of DNA templates in vitro, and is therefore inefficient and expensive.

Although much faster, the transient route is very limited because of the virus's low infectivity, inability to transfect most of the plant body, and gene size limitations. There are publications describing the use of agro-infiltration for delivery of infectious viral vectors into the plant cell (Liu & Lomonossoff, 2002, *J. Virol. Methods*, 105, 343-348) or assembly of viral vectors from agrobacterium-delivered viral vector components (Marillonnet et al., 2004, *Proc. Natl. Acad. Sci. USA*, 101, 6852-6857). However, these publications do not address the issue of efficient and synchronized formation of viral replicons in each plant cell of agro-infiltrated tissue and further vector spread depends on the ability of the virus for cell-to-cell and systemic movement. This movement requires a relatively long time and usually viral vectors provide for the highest possible yield for said vector in approx. 10-14 days after infection. This is not acceptable for the production of recombinant proteins that strongly interfere with plant cellular processes, especially highly cytotoxic proteins like restriction enzymes, proteases, non-specific nucleases, many pharmaceutical proteins. In contrast, a standard vector delivered via agro-infiltration reaches its highest possible expression level in 3-4 days after agro-delivery, but the yield provided by such a vector is unacceptably low. We therefore face the problem caused by the low efficiency of standard transcriptional vectors driven by constitutive promoters to express the protein of interest, despite these vectors provide for expression of gene(s) of interest in practically every cell of agro-infiltrated plant tissue, and vice-versa, agro-delivered viral vectors are capable of providing for high expression level, but rarely initiate replication and thus do not provide for expression in the majority of cells, but only in a small fraction (less than 1% of all agroinfiltrated tissue). As the result, such virus-based vectors require significantly (3-4 folds) longer time to provide for expression, but productivity of the system remains lower than it could theoretically be, especially in case of cytotoxic proteins. This is serious drawback for using viral vectors in transient expression systems, as they do not provide for synchronized expression in agro-infiltrated tissue, thus affecting the yield, especially in case of cytotoxic genes to be expressed. Also, an infected plant host does not contain viral vectors in a large proportion of its tissues, thus excluding tissues from the production process. Additionally, the time required for achieving the best possible spreading (and expression level) of a viral vector over the infected plant is 3-4 times longer in comparison with standard agro-infiltration protocols. Moreover, none of the described systems for transient expression addressed the issue of increasing the biological safety of the system, which is an important element in industrial scale protein production involving the use of genetically engineered organisms.

Despite many publications in the field including patented technologies, there are still no large scale virus-based production systems that work with sufficient efficiency and yield for commercial high-yield production, predominantly due to two main reasons:

Firstly, transient plant virus-based expression systems are generally restricted to specific hosts, which may not be suitable for large scale cultivation due to their susceptibility to environmental factors. Moreover, they are generally restricted to certain parts of a plant host, thus excluding most of the plant biomass from the production process and as a result minimizes the relative yield of recombinant product per unit of plant biomass down to a level comparable to that achievable by a conventional transcription promoter in a transgenic plant;

Secondly, attempts to scale up the virus-based production system by generating transgenic plant hosts having the viral replicon precursor stably integrated in each cell has not provided a solution either, in particular because of underperformance of said replicons in such position, "leakiness" of the gene of interest to be expressed from said replicon and lack of an efficient switch system for said vectors. Some progress was achieved with PVX-based vectors by using suppressors of PTGS silencing as trigger of RNA replicon formation (Mallory et al., 2002, *Nature Biotechnol.*, 20, 622-625), but the system is still far below the practical value, as there is no solution provided for an efficient control of the switch (PTGS suppressor) triggering viral vector replication. However, this system provided for an expression level of the GUS gene reaching 3% of total soluble protein (TSP), which is the best known so far for this type of system, but still no better than a conventional transgene expression system under control of a strong promoter. Another inducible system based on a plant tripartite RNA virus (Mori et al., 2001, *Plant J.*, 27, 79-86), Brome Mosaic Virus (BMV), gave a very low yield of the protein of interest (3-4 µg/g fresh weight), which is comparable with the yields provided by standard transcriptional promoters.

The low expression levels achieved so far with plant expression systems are a major reason why these systems are hardly competitive with other expression systems like bacterial, fungal, or insect cell expression systems. Low expression levels give rise to very high downstream costs for protein isolation and purification in a huge background of plant material. Therefore, costs for downstream processing quickly decrease, as the yield of the protein or product of interest per unit plant biomass increases.

There is presently no large-scale plant transient expression system the yield and efficiency of which would be sufficiently high to compete on the market with other large-scale expression systems like bacterial, fungal, or insect cell expression systems. Such a plant expression would have to fulfill the following criteria as good as possible:

(i) high yield, including expression of the protein of interest in as many plant tissues as possible and in as many cells of said tissues;

(ii) for preventing a deleterious effect of protein expression on plant cells survival, expression of the protein or product of interest should start in all plant cells of the treated plant or plant tissue at the same time.

Typically, the protein or product of interest accumulates in each cell producing said product or protein up to a certain point. During accumulation, however, degradative processes frequently set on that tend to reduce the yield or quality of the protein or product of interest. Therefore, there is an optimal point in time after switching on expression, where the product or protein of interest should be harvested. This optimal point in time should be reached in all tissues or cells of a plant and in all plants of a selected lot at the same time in order to make the overall process efficient and profitable;

(iii) the system shall incorporate increased biosafety features, such that agrobacteria used for agroinfiltration shall have at least one of the following features: low or zero survival rate in open environment, low or zero infectivity toward non-target organisms or non-target plants.

Therefore, it is an object of the invention to provide a process for protein expression in a plant system that is scalable to large-scale applications, gives a high yield of the protein to be expressed, and, at the same time, is biologically safe in that the probability of transfection or transformation of non-target organisms with foreign DNA is low.

GENERAL DESCRIPTION OF THE INVENTION

This object is achieved by a process of producing a protein of interest by transient expression of said protein of interest from a sequence of interest in a target plant or in target plant leaves, comprising:

transfecting said plant or said plant leaves by infiltrating said plant or said plant leaves with an *Agrobacterium* strain in the presence or in the absence of a complementing factor, said *Agrobacterium* strain containing in T-DNA a heterologous DNA sequence having a sequence portion encoding a replicon, wherein said sequence encoding a replicon contains
(i) sequences necessary for replicon function of said replicon, said sequences being derived from a plant virus, and
(ii) said sequence of interest to be expressed, wherein said *Agrobacterium* strain is provided with a first genetic modification rendering said *Agrobacterium* strain defective for transfecting organisms including said plant or said plant leaves with said T-DNA in the absence of said complementing factor.

The invention further provides a kit of parts comprising
(i) the *Agrobacterium* strain as defined above and
(ii) a plant, or seeds thereof, encoding a complementing factor capable of complementing the defectiveness of said *Agrobacterium* strain defined above.

The invention further provides a kit of parts comprising
(i) the *Agrobacterium* strain as defined above and
(ii) a second *Agrobacterium* strain encoding a complementing factor capable of complementing the defectiveness of said *Agrobacterium* strain defined in above.

The invention further provides bacteria of the genus *Agrobacterium* for the processes of the invention, said bacteria being characterized by:

(i) having a first genetic modification rendering said bacteria defective in a function required for introducing T-DNA into cells of a plant or plant leaves in the absence of a complementing factor, (ii) being defective in their conjugative ability of plasmid transfer to other bacteria, and (iii) being auxotrophic for an essential metabolite required for growth of said *Agrobacterium*.

According to a general principle in nature, two or more conflicting properties of a system are difficult to improve at the same time, since the improvement of one property tends to affect negatively the other property and vice versa. In plant-based protein expression systems, achieving a high expression level of the protein to be expressed and, at the same time, achieving a high biological safety is difficult to achieve, since a high expression efficiency tends to make the system less selective and thereby less biologically safe. If, for example, the *Agrobacterium* strain used to infect a plant is made highly infectious for achieving a highly efficient expression system, that *Agrobacterium* strain tends to have a high likelihood of transfecting non-target plants and to spread recombinant T-DNA in the environment, which has to be avoided. If, on the other hand, the biological safety is improved by making the *Agrobacterium* strain less infectious, the transfection and expression efficiency in the target plant will suffer. Thus, biological safety and expression efficiency are such conflicting properties.

The requirements to a plant-based protein expression system get even more complex, if the system should be suited for large-scale applications, i.e. concomitant expression in many plants or many plant leaves. On the one hand, biological safety is more important in large-scale applications due to a higher probability that transgenic organisms escape into the open environment. On the other hand, a high protein expression efficiency and yield is essential in large-scale applications for achieving an economically competitive process.

The present invention provides for the first time the means for creating a large-scale, highly efficient, and biologically safe process for producing proteins of interest.

In the process of the invention, a protein of interest in expressed transiently from a sequence of interest in plants or plant leaves. Transient expression is achieved by transient transfection of said plant or said plant leaves. The term "transient transfection" means that the introduction of said heterologous DNA sequence is done without selection of transfected cells for stable incorporation of said heterologous DNA sequence into a plant chromosome. Said sequence of interest encodes said protein of interest. Said sequence of interest is introduced in said plant or said plant leaves using said *Agrobacterium* strain that is capable of introducing foreign DNA in plant cells. Said sequence of interest is heterologous to said plant virus from which said replicon is derived, i.e. the process of the invention does not comprise the case where a wild-type plant virus is transformed into plants or plant leaves. Said DNA sequence is heterologous, since it contains a heterologous sequence of interest. Preferably, said sequence of interest is not a sequence native to said *Agrobacterium* strain.

Said plants or plant leaves are transiently transfected with said *Agrobacterium* strain. Said plants or plant leaves should be transfected such that many cells and many tissues of said plant are transfected in one working step. This may best be achieved by agro-infiltration, but other methods that allow transfection of major parts of said plant or said plant leaves can also be applied. It is therefore preferred that said plants or plant leaves are transiently transfected by infiltrating said plant or said plant leaves with said *Agrobacterium* strain. Said infiltrating is an important element of the invention, since it contributes significantly to the efficiency of the system. The efficiency is the higher, the more cells of said plant or said plant cells express said protein of interest and the better the onset of expression is synchronized in various tissues and cells. Infiltration allows to transform many cells of said plant or said plant leaves in one working step, whereby the point in time at which expression of said protein of interest sets on in the various plant tissues and in various parts of said plant is substantially synchronized. Furthermore, infiltration substantially increases the probability that a large proportion of the cells of said plant or said plant leaves are transformed.

Transfection and expression then do not depend on long-distance movement of said replicon in said plant or in said plant leaves, although the capability for long-distance movement of said replicon may further increase the overall efficiency.

The process of the invention is designed for large-scale application to plants, i.e. for being carried out with many plants in parallel. In the process of the invention, preferably at least 5, more preferably at least 10, more preferably at least 30, even more preferably at least 100, and most preferably at least 1000 plants are transfected with said *Agrobacterium* strain in parallel.

If the process of the invention is performed with entire plants, transfection (preferably: infiltration) is performed at several parts of said plant, e.g. most leaves are transfected or infiltrated. Preferably, all leaves are transfected or infiltrated. More preferably, all leaves and the stem of the plant are transfected or infiltrated. All tissues should be transfected or infiltrated that are later harvested for isolating the protein of interest. There is in general no need to infiltrate roots, although expression and harvesting in roots may further increase the overall efficiency of the system. Whole plants or at least those parts above the soil may be infiltrated by dipping the plant upside down in a suspension of said *Agrobacterium* strain, application of vacuum, followed by rapid release of the vacuum. This procedure may be upscaled and applied to many plants one after the other or at the same time.

If the process of the invention is performed with plant leaves, infiltration is performed at more than one sectors of said leaves. Preferably, leaves are sprayed or dipped into a suspension of said *Agrobacterium* strain, preferably followed by pressing or sucking *Agrobacterium* cells into the leave tissue. Preferably, said plant leaves used according to the invention are attached to a plant. Preferably, the process of the invention is not performed in plant tissue culture.

Infiltration or agro-infiltration may be defined as a transfection method using a suspension of Agrobacteria, wherein a pressure difference is used for pressing Agrobacteria into plant tissue (intercellular space).

Alternatively, Agrobacteria can be delivered into the plant tissue by using high-pressure spray device to deploy a mixture of agrobacteria together with an abrasive to plants, as it was done for delivery of viral particles (Pogue et al., 2002, *Annu. Rev. Phytopathol.*, 40, 45-74).

Said *Agrobacterium* strain is provided with a first genetic modification rendering said *Agrobacterium* strain defective for transfecting organisms with said T-DNA in the absence of a complementing factor, which is an essential element of the invention for improving biological safety. Said organisms are organisms transfection of which with said heterologous DNA sequence is not desired ("non-target organisms"). Non-target organisms are inter alia plants and microbial organisms like bacteria or fungi. In the absence of said complementing factor, the plant species of the invention is also a non-target organism. In the absence of said complemeting factor, the *Agrobacterium* strain is defective in, preferably incapable of, infecting and transfecting such non-target organisms.

Said *Agrobacterium* strain, said plant (or said plant leaves), and said complementing factor are selected for allowing transfection and/or expression of said sequence of interest upon infection of said plant with said *Agrobacterium* strain, whereas transfection and/or expression of non-target organisms is unlikely. The defectiveness, preferably the incabability, of said *Agrobacterium* strain for transfecting non-target organisms is achieved by a genetic modification of said *Agrobacterium* strain, in the following referred to as said first genetic modification.

Said first genetic modification preferably renders said *Agrobacterium* strain defective in a function required for introducing said T-DNA in cells of said plant or plant leaves. This may be achieved by deleting or disrupting an agrobacterial gene coding for a function required for transfecting target organisms. Such functions are inter alia encoded on Ti-plasmids, like on the Ti-plasmid carrying said T-DNA to be introduced in cells of said plant or plant leaves. Examples of such genes are the agrobacterial genes VirE2, GALLS, and VirF.

In another embodiment, said first genetic modification renders said *Agrobacterium* strain auxotrophic, whereby its growth is dependent on an externally added metabolite. In the absence of the externally added metabolite, said *Agrobacterium* strain is defective for transfecting organisms with said T-DNA.

In a further embodiment, a function of said *Agrobacterium* strain required for transfecting said organisms is placed under the control of a heterologous chemically regulated promoter as said first genetic modification. Examples of such genes are the agrobacterial genes VirE2, GALLS, and VirF that may, for example, be placed under a lac promoter. In such embodiment, said complementing factor is a small molecular compound capable of regulating said chemically regulated promoter. In the case of the lac promoter, the complementing factor may be IPTG or lactose. A agrobacterial suspension applied to said plant or said plant leaves may then contain said small molecular compound such as IPTG or lactose for enabling infection of said plant and, preferably, introduction of said T-DNA into cells of said plant.

In another embodiment, said first genetic modification renders said *Agrobacterium* strain conditionally lethal, and said complementing factor is an essential metabolite for said *Agrobacterium* strain required for survival of said *Agrobacterium* strain.

The above-mentioned embodiments may be combined. For example, if said *Agrobacterium* strain is defective in a function required for introducing said T-DNA in cells of said plant or plant leaves, it may additionally be auxotrophic and/or conditionally lethal for increasing the biological safety to the system.

Said complementing factor provides the function rendered defective by said first genetic modification. In the presence of said complementing factor, transfection of cells of said plant or said plant leaves with said T-DNA by said defective *Agrobacterium* strain is reestablished. Said complementing factor may be a small molecular compound or, depending on the first genetic modification, a polymeric molecule like a protein or a nucleic acid coding for said protein. If said *Agrobacterium* strain is auxotrophic, said complementing factor allows growth and infectivity of said *Agrobacterium* strain. If said *Agrobacterium* strain has a defective VirE2, GALLS, and VirF gene as said first genetic modification, said complementing factor is or codes for VirE2, GALLS, or VirF, respectively. If said *Agrobacterium* strain is under the control of a chemically regulated promoter, said complementing factor may be small molecular compound capable of regulating, preferably inducing, said chemically regulated promoter.

Said complementing factor has to be provided such that it can perform its purpose. If said complementing factor is a small-molecular compound, it may be present in the aqueous suspension of said *Agrobacterium* strain used for infiltrating said plant or said plant leaves. If said complementing factor is a protein, it may also be added to this aqueous suspension. Preferably, however, a complementing factor which is a protein (e.g. VirE2, GALLS, or VirF) is encoded in DNA and provided such that it is present in said plant or in said plant leaves upon said infiltration. In one embodiment, said plant or said leaves are infiltrated with a second *Agrobacterium* strain capable of introducing said complementing factor or a DNA coding therefore into said plant or said plant leaves. Said second *Agrobacterium* strain preferably is an *Agrobacterium* strain not having said first genetic modification and not having said heterologous DNA sequence of the invention. Said *Agrobacterium* strains of the invention and said second *Agrobacterium* strain may be used as a mixture when infiltrating said plant or plant leaves. Should small amounts of such a mixture escape the (preferably contained) environment where the process of the invention is carried out, such a mixture of *Agrobacterium* strain is quickly diluted such that the likelihood of having both strains close to each other quickly diminishes. Non-target organisms will then not come in contact with both *Agrobacterium* strains at the same time, whereby no artificial or foreign nucleic acids (e.g. said heterologous DNA sequence) will be transformed into such a non-target organism.

In another, more preferred, embodiment, said complementing factor is expressed in said plant or said plant leaves, either stably or transiently, whereby stable expression of said complementing factor is preferred. In this embodiment, said plant is provided with a genetic modification (in the following and in the claims referred to as "second genetic modification") encoding said complementing factor. A high biological safety can be achieved in this way, since said *Agrobacterium* strain transforms exclusively the plant having said second genetic modification. The probability that said *Agrobacterium* strain transforms undesired organisms or undesired plants is very low, since these organisms lack said second genetic modification.

The biological safety of the process described so far can further be improved in various ways. Said sequence portion encoding a replicon may encode a replicon that is defective in a function enabling spreading of said replicon in said plant or in said plant leaves. Said function may be a function for long-distance or cell-to-cell movement of said replicon, e.g. a viral coat protein or a viral movement protein, respectively. Preferably, said replicon lacks at least the capabillity of long distance movement, whereby spread of said replicon to other plants can be prevented. The lack of the capability for long distance movement can, in principle, be disadvantageous for the protein expression efficiency. However, in the system of this invention, this disadvantage can be compensated by other elements of the invention, e.g. by infiltrating major parts of said plant or said plant leaves and/or by the method of improving RNA replicon formation described below.

Another approach for further improving biological safety is to use an *Agrobacterium* strain for transfecting said plant, that expresses the oncogenic suppressive activity protein Osa (REF) and to employ a second *Agrobacterium* strain for providing the virE2 gene. Further, said *Agrobacterium* strain may have a genetically modified quorum sensing or virulence induction regulatory systems for reducing T-DNA transfer to non-target organisms.

The biological safety of the process of the invention can also be improved in that said *Agrobacterium* strain has a further genetic modification that renders said *Agrobacterium* strain defective for conjugative transfer of plasmid DNA to other bacteria. Conjugative transfer may be achieved by disabling a function of at least one of the following agrobacterial genes: oriT, traG, and traF.

Said sequence portion of said heterologous DNA sequence may encode a DNA replicon or an RNA replicon. RNA replicons are preferred and the following description is mostly concerned with sequence portions encoding RNA replicons.

Said sequence portion encoding a replicon contains sequences necessary for replicon function and a sequence of interest to be expressed from said replicon. Said sequence of interest to be expressed typically codes for a protein of interest and may contain regulatory sequences for translating said protein of interest from said replicon or from subgenomic RNA of an RNA replicon.

If said replicon is an RNA replicon, the sequences necessary for RNA replicon function of said replicon (i) correspond to sequences of said RNA virus inter alia in that the former are a DNA copy (e.g. cDNA) of the latter. In the case of a DNA replicon, said sequences for replicon function provide the DNA replicon with the function to replicate in the cell nucleus; the DNA replicon may be formed from said heterologous DNA sequence by replication using the heterologous DNA sequence or a portion thereof as a template. In the case of an RNA replicon, said sequences for replicon function provide the RNA replicon with the function to replicate in the cytosol. Said sequences for RNA replicon function typically code for one or more proteins involved in replication like an RNA-dependent RNA polymerase (RdRp, replicase). Said sequences for replicon function may further be or code for functions required for expressing a replicase like subgenomic promoters, transcription enhancers or translation enhancers. Proteins involved in cell-to-cell or systemic spreading of an RNA virus in a plant like a movement protein or a coat protein do not have replicon functions, although they may be present in said heterologous DNA sequence. In any event, said sequence portion encoding a replicon does not code for a wild-type plant virus. Said sequences for replicon function are preferably derived from a sequence of a plant RNA virus, since plant RNA viruses are an easily accessible source for replicon functions. In the case of an RNA replicon, "being derived" means that said sequences for replicon function are a DNA copy of the corresponding sequences of said RNA virus and said DNA copy is incorporated in said heterologous DNA sequence contained in cell nuclei. "Being derived" implies that said sequences for replicon function do not have to be an exact DNA copy of the corresponding RNA sequence of said RNA virus, but may exhibit function-conservative differences as described below. Since said differences are function-conservative, said sequences for replicon function preferably code for proteins capable of carrying out replicon functions similarly as they do for said RNA virus.

In an embodiment where said replicon is based on a tobamovirus like tobacco mosaic virus, said replicon contains or encodes an RdRp. This replicon may further code for the movement protein. Preferably, this replicon does not contain or code for the coat protein (CP).

In a further preferred embodiment, the biological safety of the process of the invention is further improved by using highly diluted suspensions of said *Agrobacterium* strain. This embodiment not only decreases the likelihood that cells of said *Agrobacterium* strain spread in the environment, it also improves the efficiency of the process of the invention by decreasing the exposure and stress of said plant or said plant leaves upon infections with an *Agrobacterium* strain that is a pathogen for said plant. The inventors have surprisingly found that the efficiency of the process increases, within certain limits, with decreasing concentration of the Agrobacteria suspensions used in step (a) of the invention. Notably, the ability for cell-to-cell movement of the replicons generated in cells of said plant improves with decreasing concentration of these Agrobacteria suspensions. The reasons for this unexpected phenomenon have not yet been identified. It is speculated that this phenomenon is due to a response of the plant to infection by Agrobacteria and that this response does not occur (or occurs to a lesser extent) at lower Agrobacteria concentrations.

In this preferred embodiment, said plant or said plant leaves are infiltrated with a suspension of cells of said *Agrobacterium* strain, said suspension having a concentration of *Agrobacterium* cells obtainable by diluting a suspension of sells of said *Agrobacterium* strain of an OD (optical density) of 1.0 at 600 nm at least 25-fold, preferably at least 100-fold, more preferably at least 250-fold, and most preferably at least 1000-fold. Such dilutions thus lead to Agrobacteria suspensions having calculated OD values at 600 nm of at most 0.04, preferably at most 0.01, more preferably at most 0.004, and most preferably at most 0.001, respectively.

Next, an important embodiment is described that allows to increase significantly the expression efficiency in cases where said replicon is an RNA replicon. In this embodiment, said sequences for replicon function exhibit at selected localities of said sequence of said plant RNA virus function-conservative differences relative to said sequence of said plant RNA virus, said differences causing an increased frequency of replicon formation compared to an RNA replicon not exhibiting said differences. Said differences are causal for said increased frequency of replicon formation in plant cells, once the overall process has been switched on (see below). The causal connection between the increased frequency of replicon formation and said differences can be tested experimentally by comparing the frequency of replicon formation between sequences for replicon function having said differences and sequences for replicon function not having said differences. Such an experimental comparison can be made e.g. by counting protoplasts expressing said sequence of interest as described in the examples. Preferably, a sequence of interest coding for an easily detectable reporter protein like green fluorescent protein (GFP) is used for this purpose. As further described below, it is also preferred to perform the experimental comparison with RNA replicons not capable of cell-to-cell spreading.

Said function-conservative differences are introduced into said sequences for replicon function at selected localities of said sequence of said plant RNA virus. Said selected localities are localities in sequences for replicon function of said plant RNA virus that are responsible for a low probability of an RNA replicon transcribed in the nucleus to appear in the cytosol as a functional replicon. Preferably, such selected localities have a high A/T(U)-content, i.e. a high A-content and/or a high T-content (a high U-content on RNA level), or have cryptic splicing sites, i.e. sequence portions that are recognized by the nuclear splicing machinery as splicing sites. Said selected localities may be identified in an RNA virus on which an RNA replicon is based by analyzing the RNA profile of the RNA virus as exemplified below. Further, selected localities may be identified experimentally by analyzing the RNA formed in a plant cell after transfection with a heterologous DNA encoding an RNA replicon that does not exhibit the differences according to the invention. This experimental analysis may be done by RT-PCR, preferably together with sequencing of the RT-PCR products. In this way, undesired splicing products that indicate splicing events destroying the RNA replicon may be identified. Further, the exact sites of undesired splicing may be identified and then remedied by introducing said function-conservative differences at said selected localities.

Said function-conservative differences cause an increased frequency of RNA replicon formation by suppressing the deleterious effect of said selected localities on said frequency of RNA replicon formation. Said function-conservative differences may comprise a reduction of a high A/U-content in said RNA replicon by reducing a high A/T content in said sequences for replicon function of said sequence encoding said RNA replicon. Said high A/U content may be reduced by at least partial deletion or at least partial replacement by G/C bases (e.g. using the degeneracy of the genetic code), provided said differences are function-conservative. Further, cryptic splicing sites flanking A/U-rich regions of said sequences derived from a plant RNA virus may be removed. Such function-conserved differences may be introduced at one or at, preferably, several selected localities.

Preferred function-conservative differences comprise the insertion of one or more introns, most preferably nuclear introns, or one or more sequences capable of forming nuclear introns near or within A/U-rich localities of said sequences being derived from sequences of said plant RNA virus. It has surprisingly been found that the introduction of introns at or near A/U-rich localities results in an increased frequency of RNA replicon formation. Several introns may be introduced and examples are given herein for various numbers of introduced introns. The effects of more than one intron are cumulative. Further, intron insertion may be combined with other function-conservative differences at other selected localities.

FIG. 11 shows an example for the introduction of sequences capable of forming a nuclear intron, albeit in the sequence of interest to be expressed. In the example of FIG. 11, the intron is formed from two intron halves upon recombinase-catalyzed flipping of a part of said heterologous DNA sequence. This principle may also be applied to sequences for replicon function of said RNA replicon. In an embodiment wherein two different RNA replicons are formed in the same cell, recombination between said two different replicons may result in the formation of an intron from two intron halves present on different replicons. Further, an RNA replicon may be formed by recombination between two replicon precursors, neither of which is a replicon. Also in this case, an intron may be assembled from two intron halves derived from different replicon precursors.

Said heterologous DNA sequence having said sequence portion encoding said RNA replicon is operably linked or linkable to a transcription promoter, since transcription is a prerequisite for formation of said RNA replicon. The transcription promoter is preferably a constitutive promoter in order to achieve transient expression of said sequence of interest in all agroinfiltrated tissues. Examples of constitutive promoters are known in the art.

In one embodiment of the invention, said sequence encoding an RNA replicon has one or more segments that code together for said RNA replicon, i.e. said RNA replicon is not encoded by one continuous DNA. Instead, said RNA replicon is encoded discontinuously by two or more segments, whereby said segments may be present on the same T-DNA preferably contiguous to each other. Formation of said RNA replicon may then require rearrangement of said segments, e.g. by recombination. A recombinase for said recombinantion may be provided by an additonal *Agrobacterium* strain or by an engineered plant host, thus confining the transient expression to said plant host. As an example, a part of a sequence for replicon function (e.g. a part of a sequence coding for a replicase) may be present in said heterologous DNA sequence in a flipped orientation relative to other parts of such a sequence. The flipped part may be flanked by recombination sites. Then the transcript of the heterologous DNA will not be a replicon, since said replicon function cannot be provided (e.g. because the transcript does not code for a functional replicase). Providing a site-specific recombinase recognizing the recombination sites allows to flip one of said segments such that a replicon is encoded continuously. In this embodiment, providing the recombinase may function as a switch for switching on replicon formation and expression of a sequence of interest (see further below) and contributes to a high biological safety.

Alternatively, one of said segments may be present on Agrobacterial T-DNA and another one may be incorporated in a plant chromosome. Formation of an RNA replicon will then require transcription of both segments and trans-splicing of both transcripts for assembling said RNA replicon. This embodiment may be used for quickly segregating the segments that encode together said RNA replicon in progeny plants or cells as described in detail in PCT/EP03/02986, thus contributing to the biological safety of the system.

The process of the invention comprises transient transfection of a plant or plant leaves with said heterologous DNA sequence of the invention (step (a)). The term "transient transfection" means the introduction of heterologous DNA without selecting transformed transgenic cells having heterologous DNA stably integrated into a plant chromosome. Transient transfection usually provides for transient replication and/or transient expression of the gene(s) encoded by heterologous DNA sequence. Said transfection of the invention causes expression of said sequence of interest. Usually expression occurs spontaneously after providing said plant or said plant leaves with said heterologous DNA sequence via agroinfiltration. If necessary, various methods of causing or switching on expression can be used. If a recombinase is used for switching on the process of the invention, said recombinase may be provided to said plant or plant leaves transiently, whereby said providing may act as a switch for expressing said protein of interest. Preferably, such a recombinase may be stably encoded in plant cells, and expressing of the recombinase under control of a constitutive or stress-inducible promoter. Inducing recombinase expression by inducing said promoter may then cause expression of said sequence of interest.

Step (b) of the process of the invention comprises isolating said protein of interest from said plant or said plant leaves transfected, preferably infiltrated, in step (a). Isolation of said protein of interest preferably comprises homogenizing the plant or said plant leaves containing expressed protein of interest. Various methods for isolating proteins from plants are described in PCT/EP02/09605 which is incorporated herein by reference and in references cited therein.

The present invention may in principal be applied to any plants for which infectious DNA or RNA viruses exist and for which agroinfiltration providing for transient expression is efficient. Preferred plants are *Nicotiana* species like *Nicotiana benthamiana* and *Nicotiana tabacum*; preferred plant species other than *Nicotiana* species are *Petunia hybrida, Brassica campestris, B. juncea*, cress, arugula, mustard, Strawberry spinach, *Chenopodium capitatum*, lettuce, sunflower, and cucumber.

Suitable plant/DNA or RNA virus pairs may be derived from the list of DNA and RNA viruses given below. In particular, due to the very high efficiency of RNA replicon formation according to the invention, the plant species specificity of plant viruses is far less pronounced when this invention is practiced. Similarly, the present invention may be used with RNA replicons based on any RNA virus. RNA viruses have generally evolved outside the cell nuclei of their host plants and will have selected localities that make a replicon based on such a virus inefficient when the replicon is produced inside cell nuclei. The invention can be applied to all RNA viruses, although the level of improvement may vary between different plant RNA viruses. The most preferred plant RNA viruses the invention may be based on are tobamoviruses, notably tobacco mosaic virus, and Potexviruses such as potato virus X. In the case of tobacco mosaic virus, it will generally be the coat protein that is replaced by said sequence of interest to be expressed. The movement protein may also be removed or replaced by a sequence of interest to be expressed. Preferably, however, an RNA replicon derived from tobacco mosaic virus should code for the movement protein and have the coat protein be replaced by said sequence of interest.

Preferred compbinations of plants and virus from which said RNA replicon is derived are: *Nicotiana* species and tobamoviruses, *Nicotiana* species and tobacoo mosaic virus etc.

Among DNA viruses the most preferable viral vectors can be built on geminiviruses. A description of a viral expression vector based on Bean Golden Mosaic Virus (BGMV) is provided in EXAMPLE 15.

The major application of the present invention is the production of a protein of interest in plants or plant leaves. If the process of the invention is performed in plants, plants that do not enter the human or animal food chain are preferred, like *Nicotiana* species. Whole plants or plant parts after agroinfiltration shall be confined to a closed environment, e.g. a glasshouse or a specially designed chamber for the incubation period necessary to provide for desired level of expression.

The efficiency of the present invention is such that a new dimension in plant expression systems is attained. The expression levels achievable with the present invention are such that expenditures for downstream processing (including separation and purification of the protein of interest) are low enough to make the process of the invention competitive with other large-scale expression systems. In prior art expression systems using stably transformed plants, the expression level is low even if virus-based vectors are used, since replicons are produced in a small fraction of the cells. Replicons that spread in the plant cannot remedy this problem, as spreading is slow, notably over long distances. Therefore, expression does not proceed uniformly in the plant and degradation of the protein of interest will already take place in some parts of the plant while in others protein expression has not even started. Additionally, transfection or agroinfiltration-based transient expression systems of the prior art do neither provide high expression levels nor a high biosafety in one production system. The invention allows to trigger expression uniformly throughout the plant or detached plant parts (e.g. leaves) via agro-mediated delivery of competent plant host. The small fraction of cells that do not produce a replicon can be quickly infected by replicons from neighbouring cells. The invention provides the first high-yield plant expression system that can be used on large scale. The invention also provides for high biosafety features by confining the transient expression system to specifically engineered competent plant host, thus reducing the probability of giving expression in non-compatent (non-target) organisms and increasing the biosafety of the system.

Bank Acc. No K02703) and RNA2 (GenBank Acc. No K02702) and RNA3 (GenBank Acc. No L00163), respectively.

Figure 15:
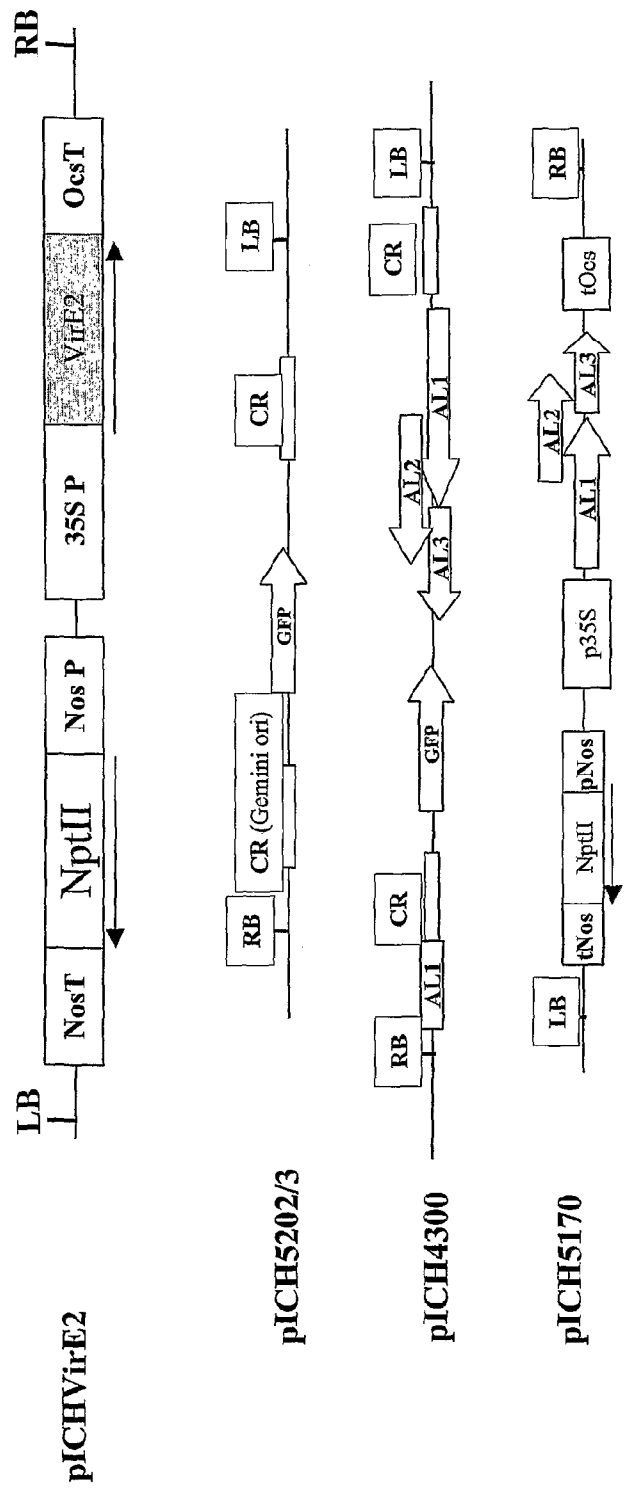

FIG. 15 is a schematic representation of T-DNA region of constructs pICHVirE2, pICH4300, pICH5202/3 and pICH5170.

Figure 16:
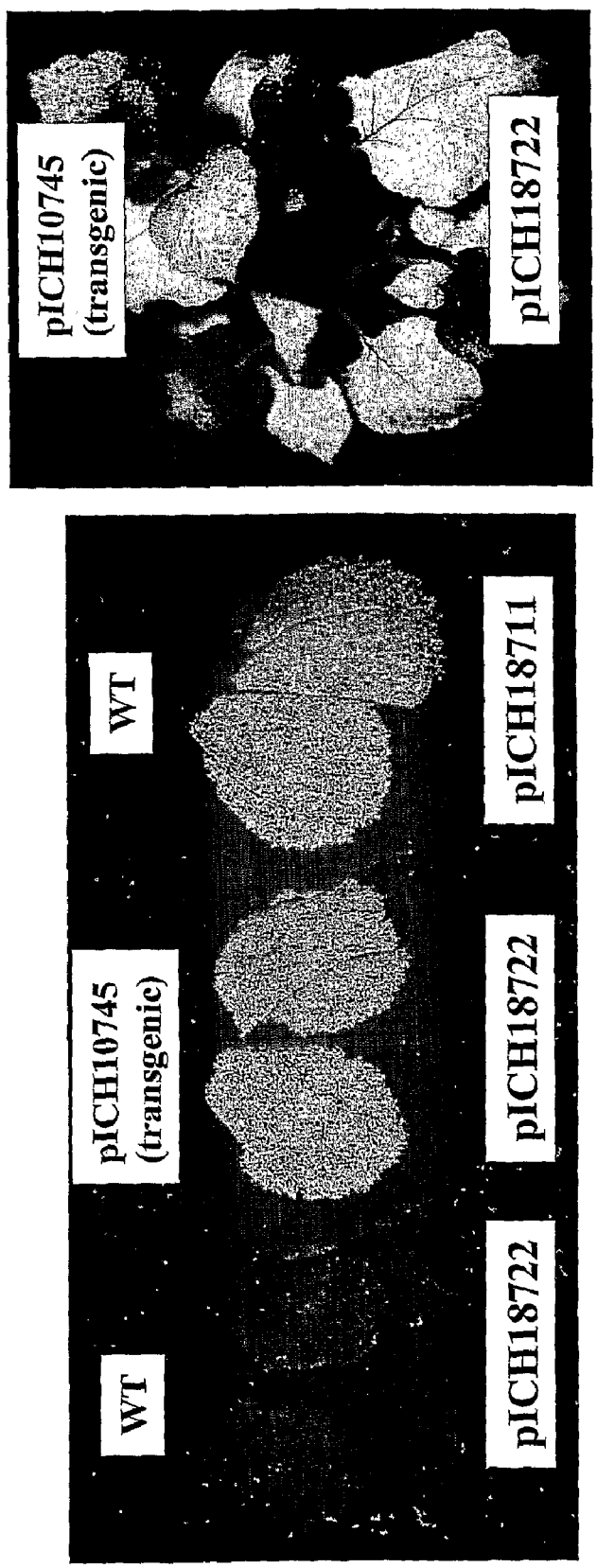

FIG. 16 shows the effect of trans-complementation of cell-to-cell movement of viral vector deficient in a functional MP (movement protein) from transgenic plant host (*N. benthamiana*). The labels at the top refer to the plant, labels at the bottom indicate the vectors used for agroinfiltration. The picture on the left shows a typical leaf of a plant treated as indicated. The picture on the right shows an entire transgenic plant.
WT: wild type plant; pICH10745 transgenic: transgenic plant expressing TVCV movement protein (MP); pICH18722: infiltration with viral vector deficient in cell-to-cell movement; pICH18711: infiltration with viral vector capable of cell-to-cell movement. Plants are shown under UV light in order to detect GFP expression.

Figure 17:
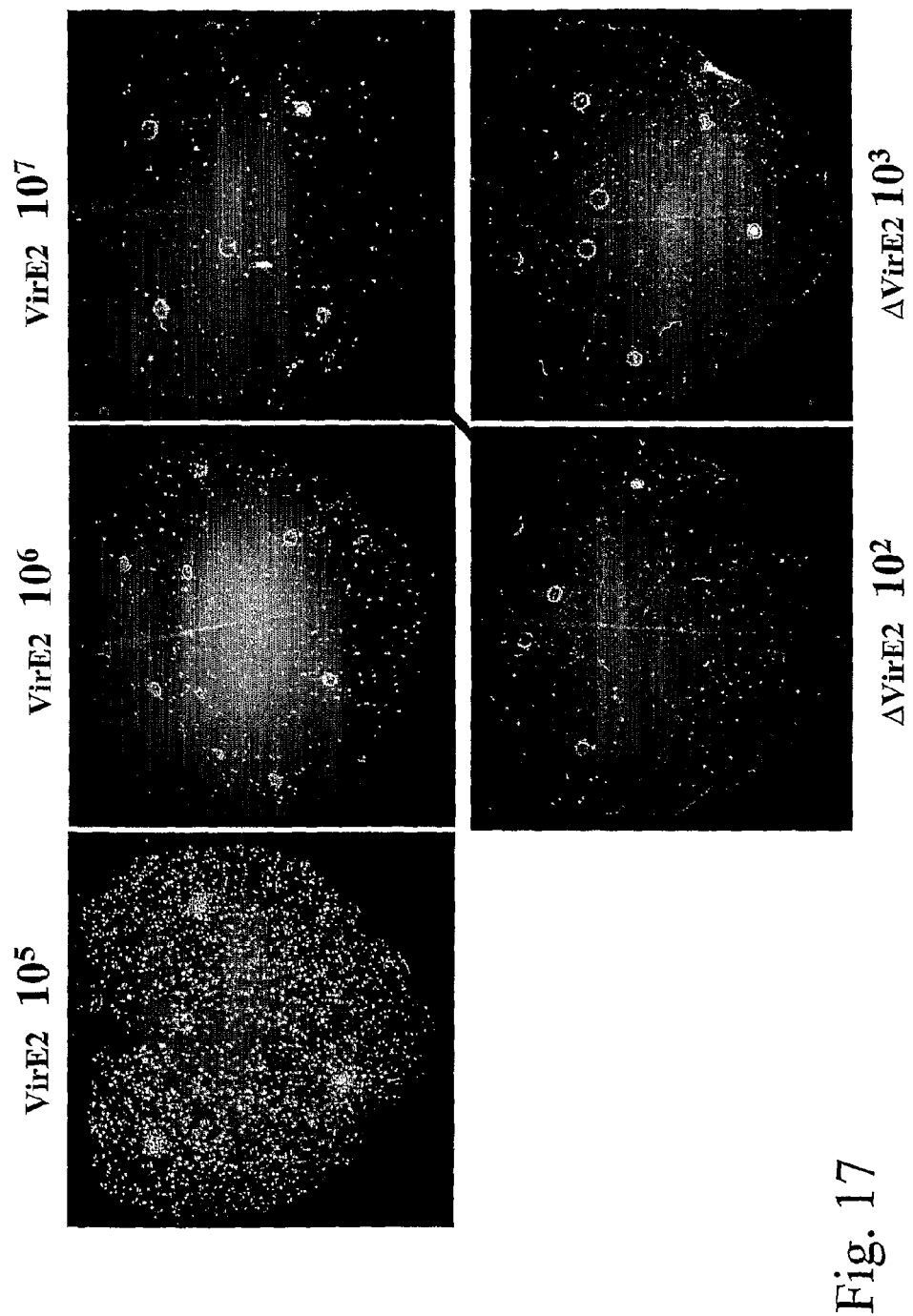

FIG. 17 shows the effect of VirE2 gene on T-DNA transfer efficiency from binary vector pICH18711. VirE2: leaves of *N. benthamiana* infiltrated with agrobacteria containing functional VirE2 gene; AvirE2: leaves of *N. benthamiana* infiltrated with agrobacteria deficient in VirE2 gene function; numbers $10^2$-$10^7$ indicate the dilutions of the agrobacterial stock before infiltration (identical $OD_{600}$ stocks for AVirE2 and VirE2 strains). The arrow links conditions exhibiting the same frequency of T-DNA transfer, that correspond to a $10^2$-fold dilution for ΔVirE2 and a $10^7$-fold dilution for VirE2 strains.

Figure 18:
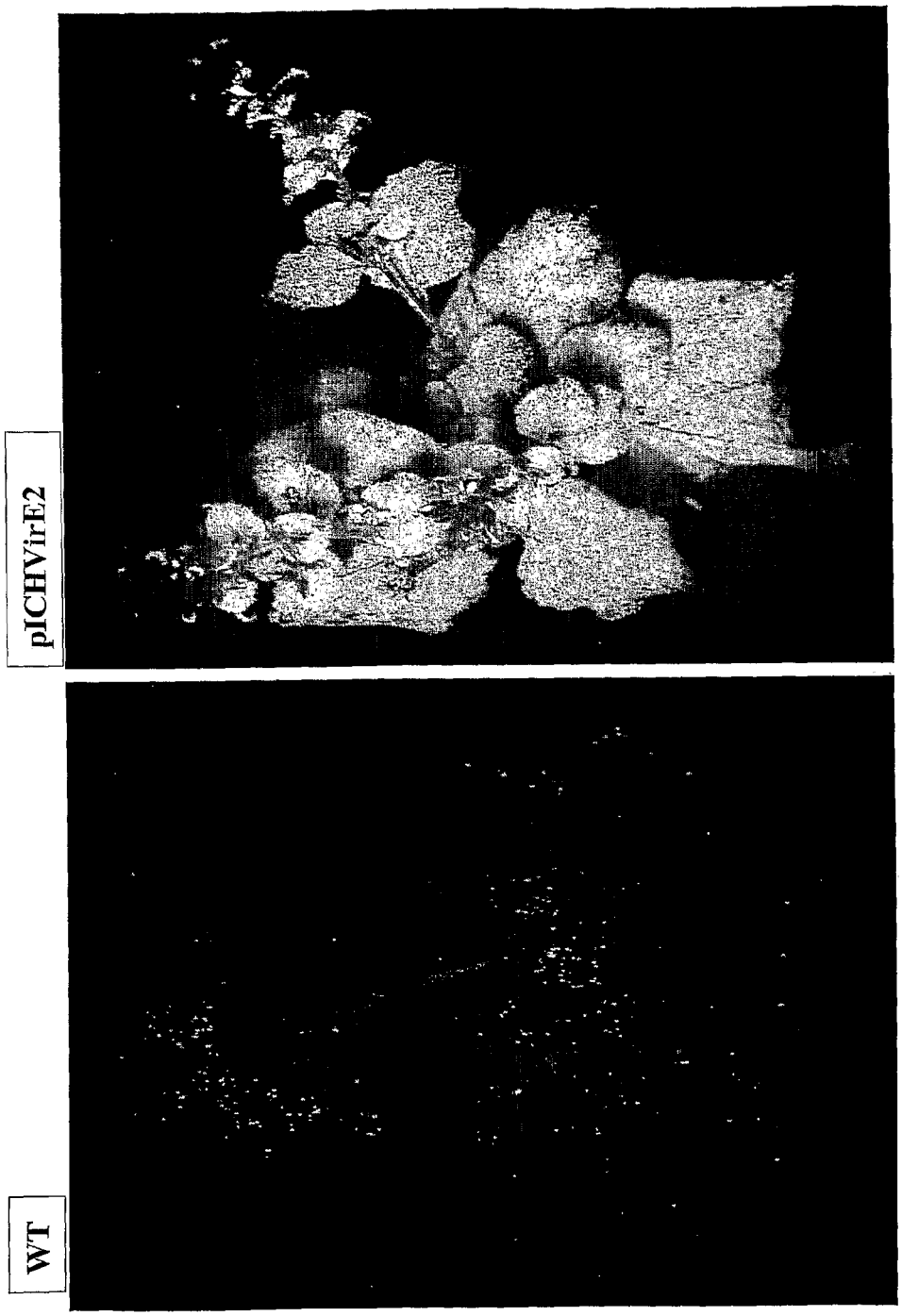

FIG. 18 shows the wild type (WT) and transgenic (pICH-VirE2) plants infiltrated with ΔVirE2 agrobacterial strain containing the pICH18711 binary vector. The pictures were taken under UV light 10 dpi (days post-infiltration). The same overnight agrobacterial culture was diluted 10-fold for infiltration of WT and 1000-fold for infiltration of the transgenic plant.

Figure 19:
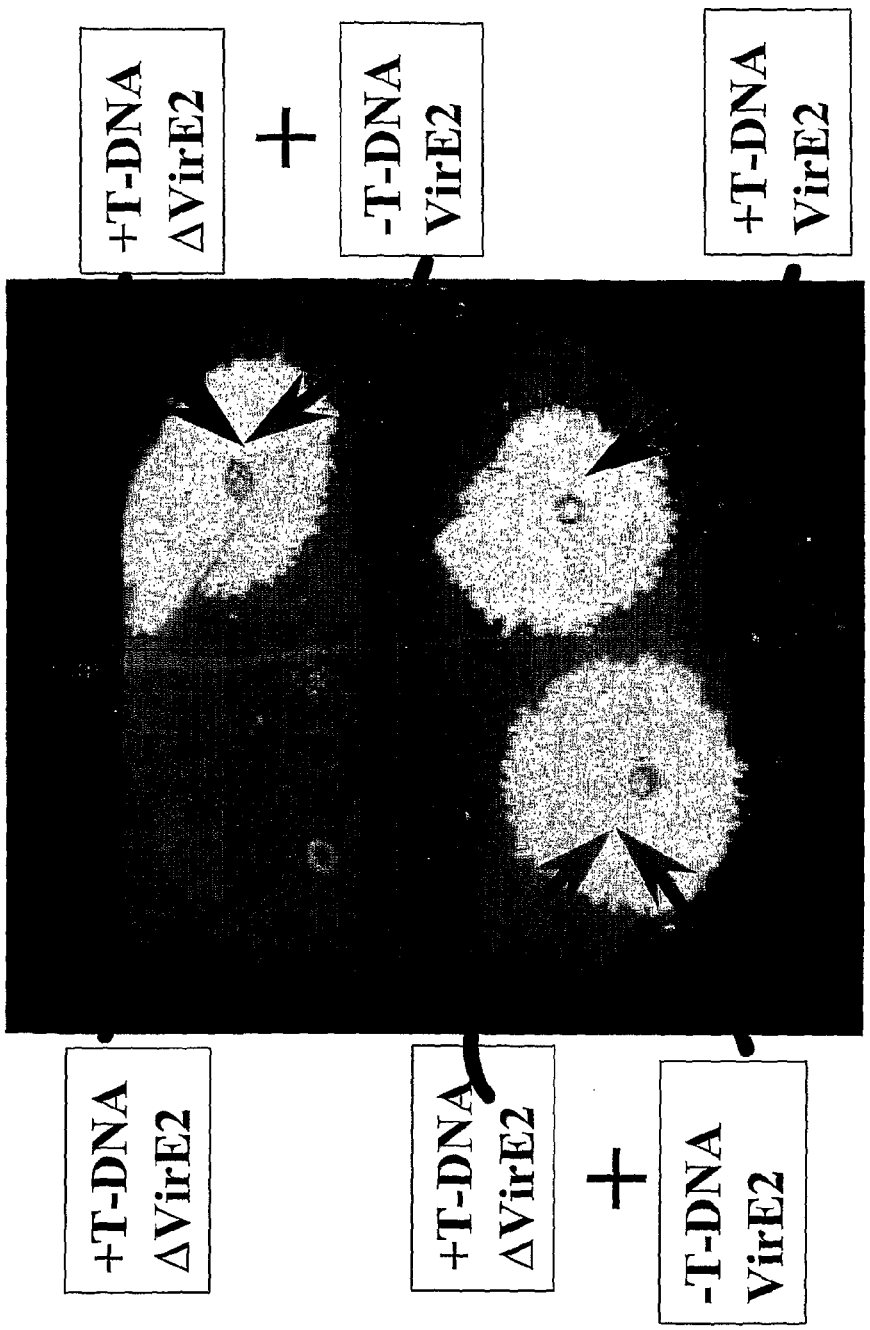

FIG. 19 shows complementation in-trans of VirE2 gene function by co-infiltration of mutant (lacking a functional virE2 gene) and wild type (maintaining VirE2 gene function) agrobacteria on a wild type plant. An *N. benthamiana* leaf infiltrated with different combinations of mutant and wild type agrobacteria is shown under UV light. A label in a box stands for a particular type of Agrobacteria. A plus sign between boxes indicates that two types of Agrobacteria were co-infiltrated on the same spot of the leaf. Plus or minus signs in front of "T-DNA" indicates the presence or absence, respectively, of T-DNA with GFP. The absence of a functional VirE2 is indicated by Δ.

Figure 20:
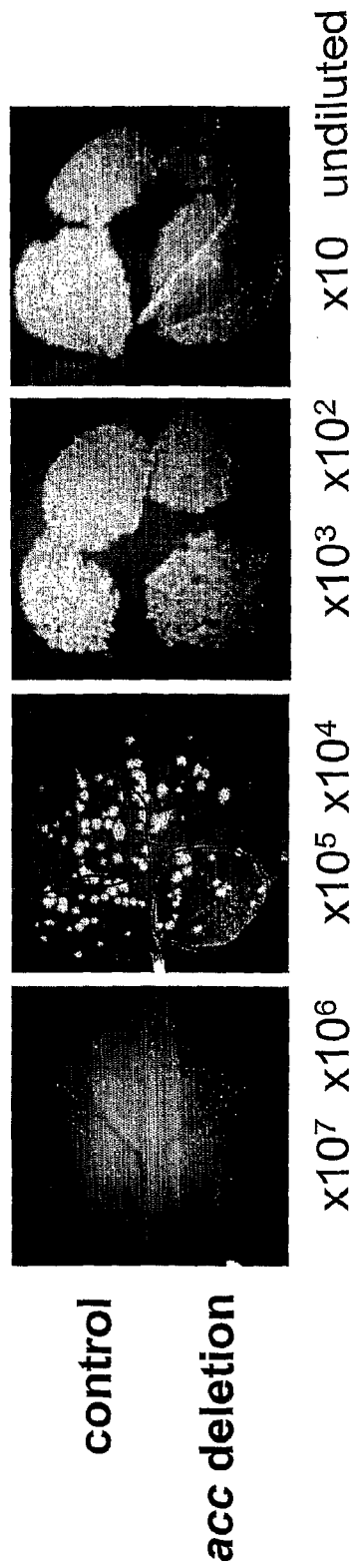

FIG. 20 shows the results of a test for the efficiency of T-DNA transfer from Agrobacteria with deletion of acc operon. An *Agrobacterium* strain GV3101 carrying Ti plasmids pMP90 (control) or pTiC58Δacc (acc deletion) was transformed with viral vector pICH18711 encoding GFP and different dilutions of an overnight culture were used for plant infiltration. The picture was taken under UV light 7 days after inoculation.

Figure 21:
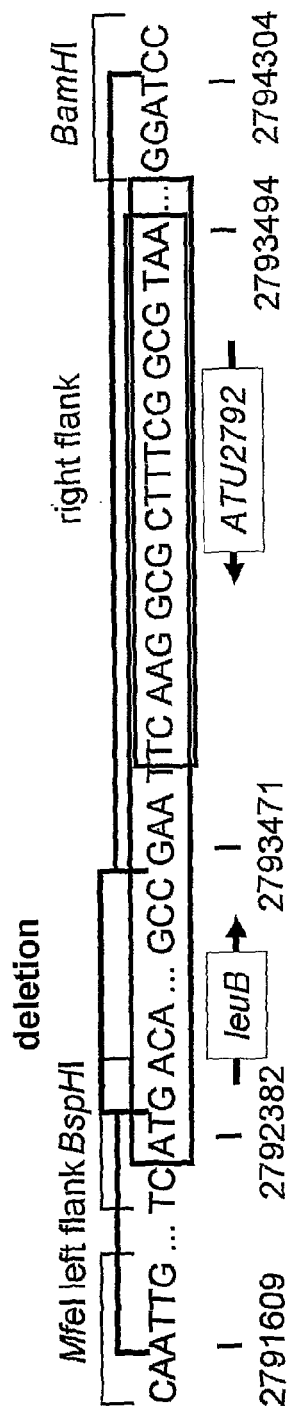
Figure 21:
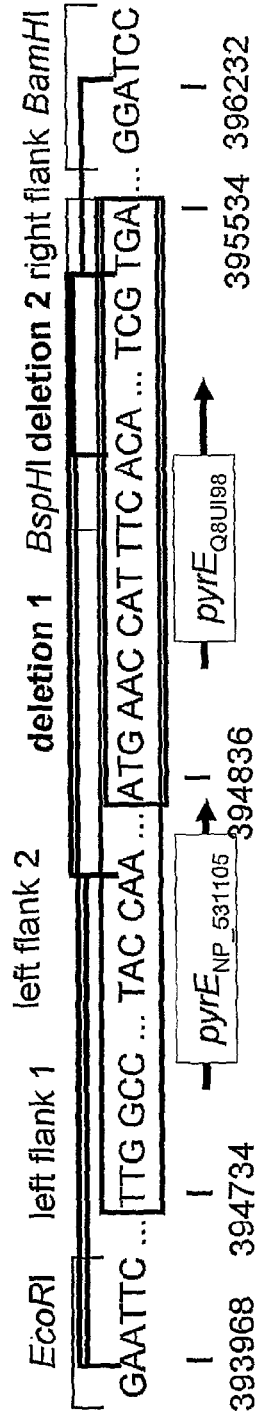

FIG. 21 depicts the strategy for generating ΔleuB and ΔpyrE mutants of agrobacteria.

Figure 22:
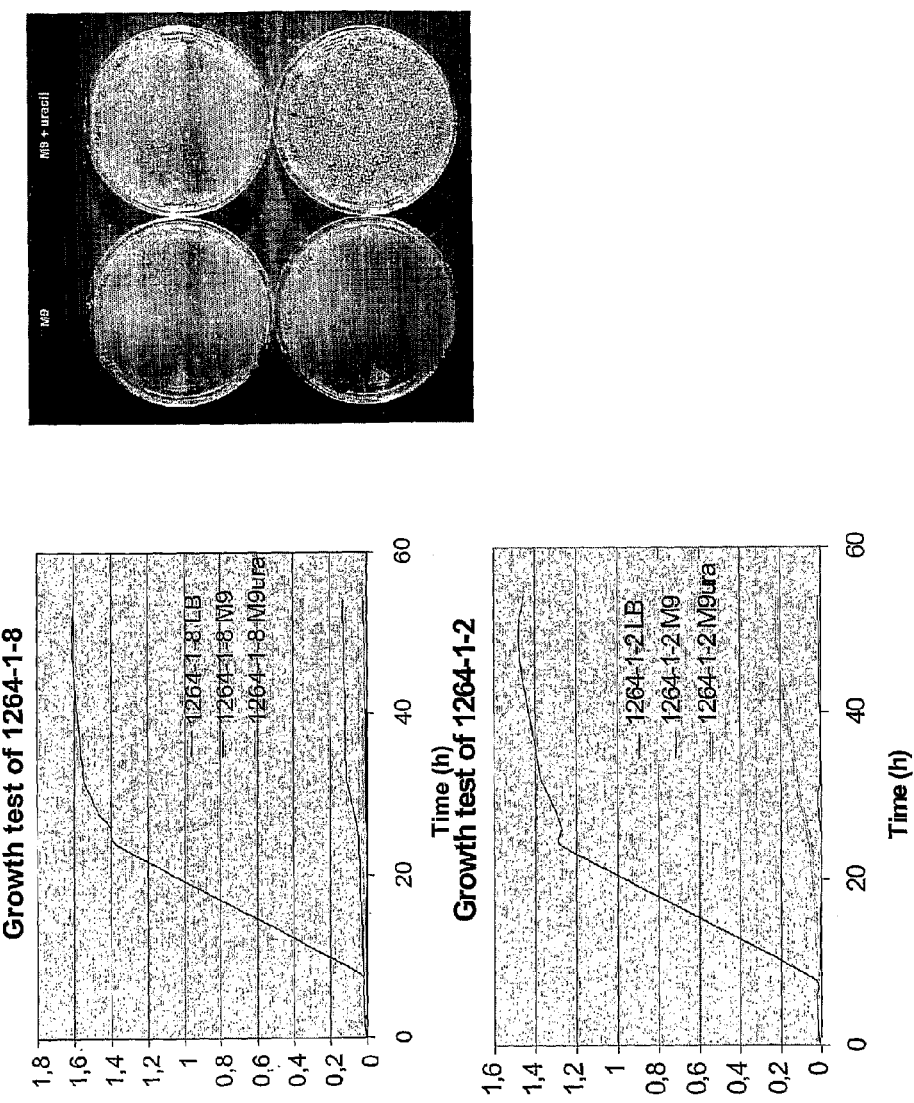

FIG. 22 shows the growth kinetic of *Agrobacterium* strain 1264 (ΔpyrE) on different media with and without complementation. The ΔpyrE mutant strains 1264-1-2 and 1264-1-8 grow only on media containing uracil. Values on the vertical axis indicate OD600.

Figure 23:
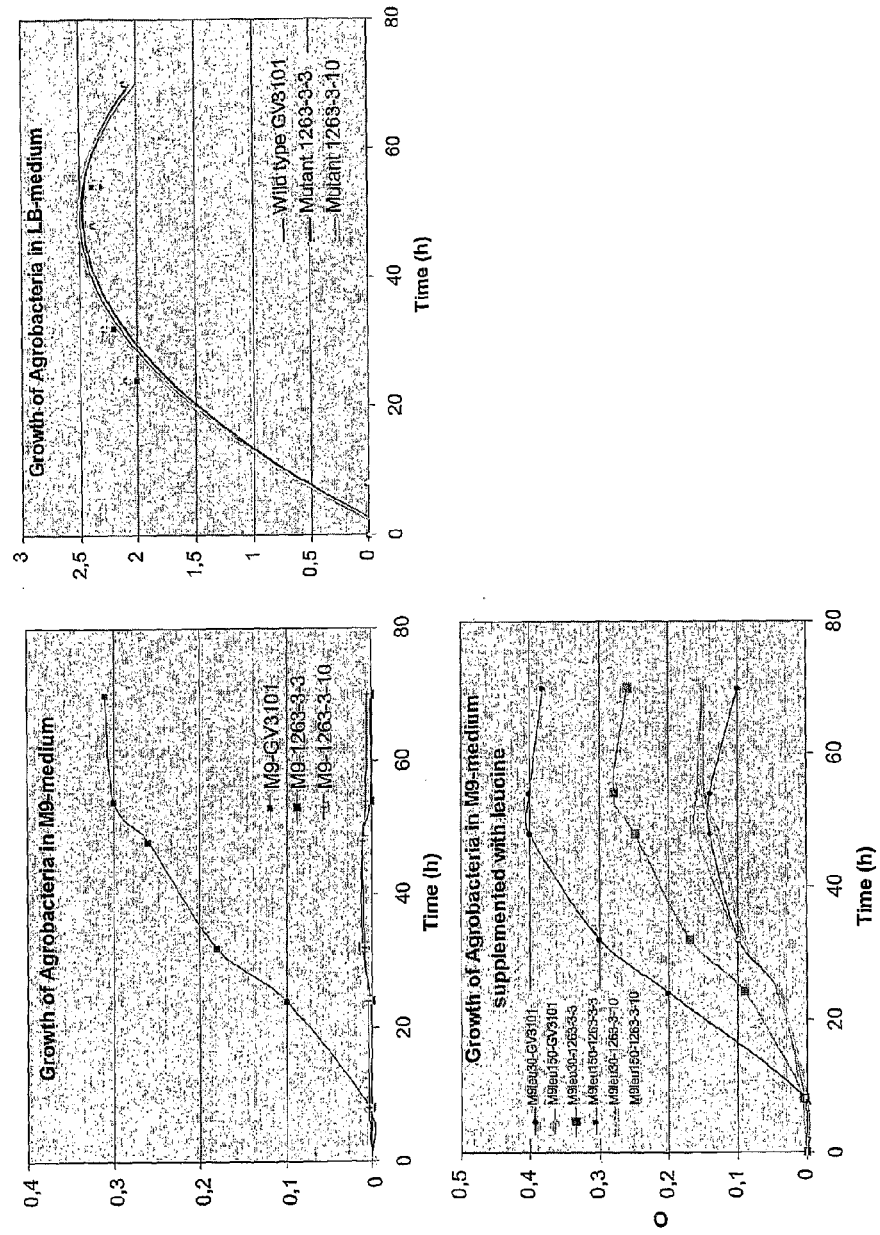

FIG. 23 shows the growth kinetics of *Agrobacterium* strain 1263 (ΔleuB) on different media with and without complementation. The ΔleuB mutant strains 1263-3-3 and 1263-3-10 are dependent on leucine whereas the wild type parent strain GV3101 is not. Values on the vertical axis indicate OD600.

PREFERRED EMBODIMENTS OF THE INVENTION

A process of producing a protein of interest by expressing a sequence of interest in a plant or in plant leaves, comprising: transfecting said plant or said plant leaves by infiltrating said plant or said plant leaves with an *Agrobacterium* strain in the presence of a complementing factor, said *Agrobacterium* strain containing in T-DNA a heterologous DNA sequence having a sequence portion encoding an RNA replicon,
wherein said sequence encoding a replicon contains
  sequences necessary for replicon function of said RNA replicon, said sequences being derived from a plant virus, and
  said sequence of interest to be expressed,
wherein said *Agrobacterium* strain is provided with a first genetic modification rendering said *Agrobacterium* strain defective for transfecting organisms with said T-DNA in the absence of said complementing factor.

A process of producing a protein of interest by expressing a sequence of interest in a plant or in plant leaves, comprising: transfecting said plant or said plant leaves, preferably by infiltrating said plant or said plant leaves, with an *Agrobacterium* strain in the presence of a complementing factor, said *Agrobacterium* strain containing in T-DNA a heterologous DNA sequence having a sequence portion encoding an RNA replicon,
wherein said sequence encoding a replicon contains
  sequences necessary for replicon function of said RNA replicon, said sequences being derived from a plant virus, and
  said sequence of interest to be expressed,
wherein said *Agrobacterium* strain is provided with a first genetic modification rendering said *Agrobacterium* strain defective for transfecting organisms with said T-DNA in the absence of said complementing factor, and
wherein said plant or said plant leaves have a second genetic modification encoding and expressing said complementing factor in said plant or said plant leaves.

A process of producing a protein of interest by expressing a sequence of interest in a plant or in plant leaves, comprising: transfecting said plant or said plant leaves by infiltrating said plant or said plant leaves in the presence of a complementing factor with a suspension of cells of an *Agrobacterium* strain, said suspension having a cell concentration corresponding to a calculated optical density at 600 nm of at most 0.04, preferably at most 0.01, more preferably at most 0.004, and most preferably at most 0.001, said *Agrobacterium* strain containing in T-DNA a heterologous DNA sequence having a sequence portion encoding an RNA replicon,
wherein said sequence encoding a replicon contains
  sequences necessary for replicon function of said RNA replicon, said sequences being derived from a plant virus, and
  said sequence of interest to be expressed,
wherein said *Agrobacterium* strain is provided with a first genetic modification rendering said *Agrobacterium* strain defective for transfecting organisms with said T-DNA in the absence of said complementing factor; and
wherein said sequences necessary for replicon function exhibit at selected localities function-conservative differences from said plant RNA virus, said differences causing an increased frequency of replicon formation compared to an RNA replicon not exhibiting said differences.

Further preferred embodiments are defined in the claims.

DETAILED DESCRIPTION OF THE INVENTION

We have developed highly active synthetic templates for the delivery of RNA viral vectors as DNA precursors using *Agrobacterium*, a soil bacterium and an efficient vector organism. Here we show that this improved 'agroinfection' process can be used to simultaneously start transient gene amplification and high-level expression in essentially all mature leaves of a plant, and that such a transfection route can be inexpensively performed on an industrial scale. We also address the biosafety issue by engineering target plant host organism, agrobacteria and/or plant virus in such a way that it allows to confine the production to engineered "competent" plant host and limit the ability of agrobacteria to infect other plants or microorganisms, that are not part of the production process. This technology combines advantages of three biological systems: speed and expression level/yield of a virus, transfection efficiency and systemic delivery of an *Agrobacterium*, and posttranslational capabilities and low production cost of a plant. The proposed process allows for an industrial production route that does not require stable genetic modification of plants with heterologous nucleic acids encoding the product of interest and is more safe, controlled and compatible with the current industrial infrastructure.

This invention describes a transient expression system for high-yield, large-scale production of a protein of interest using *agrobacterium*-mediated delivery of viral replicons or precursors thereof. Said replicon is capable of expressing the sequence of interest and said system has incorporated biosafety features, making at least two of three key components of the system (engineered plant host, agrobacteria, replicon) interdependent of each other.

Figure 1A:
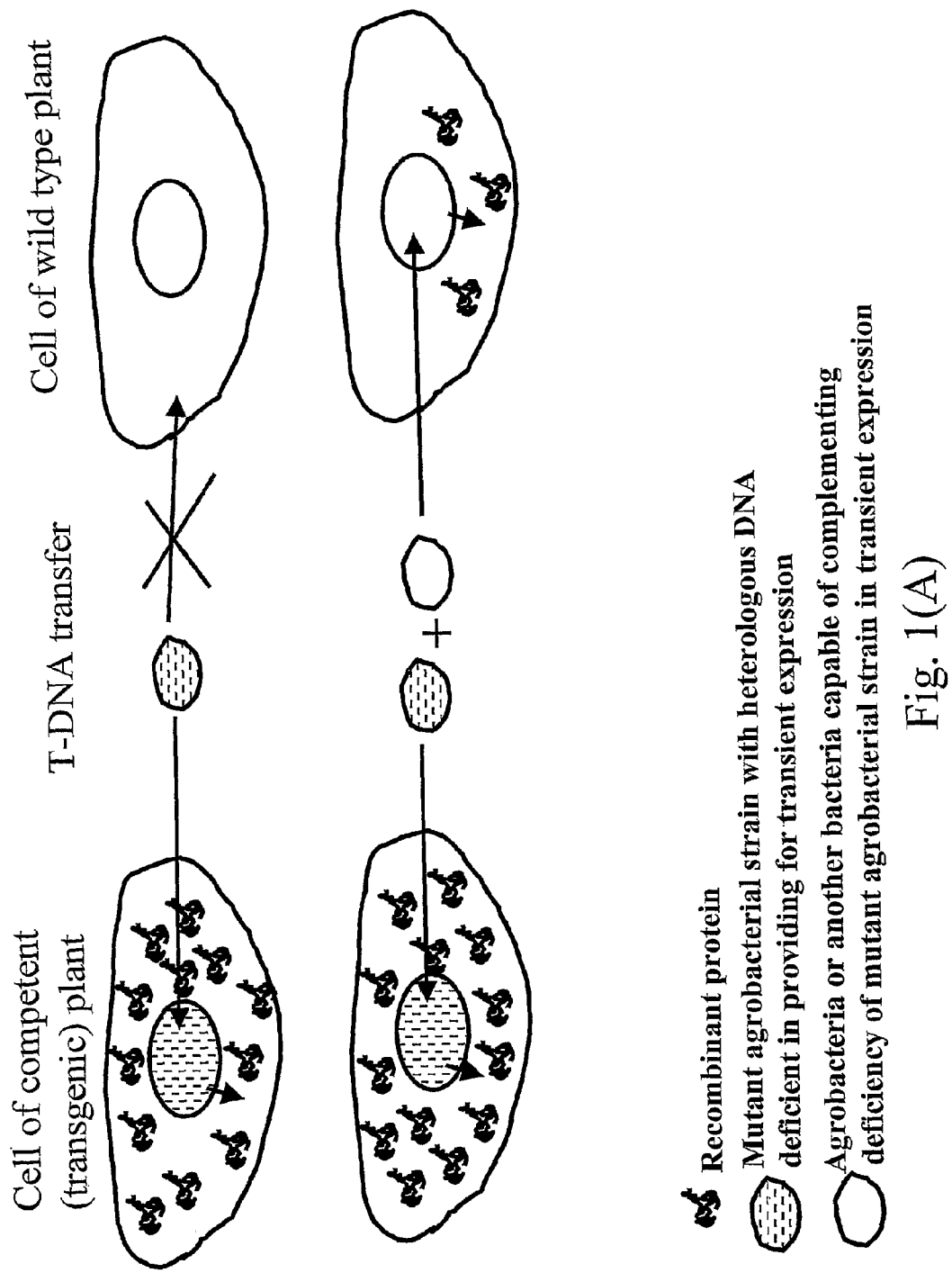
FIG. 1 depicts the general principle of the invention, based on increased frequency of increased biological safety (A) and RNA virus-based replicon formation (B).
Figure 1B:
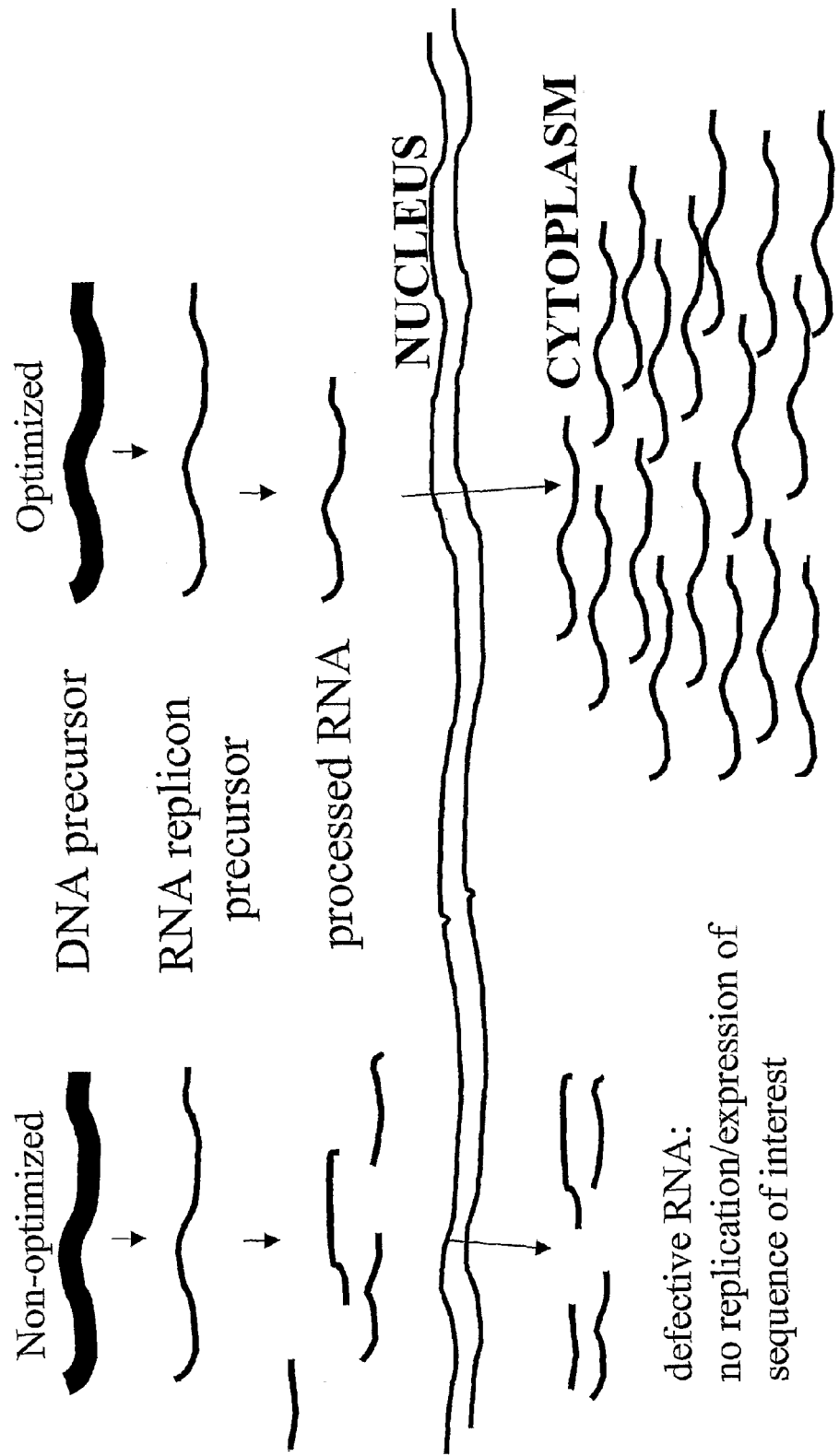
Figure 5:
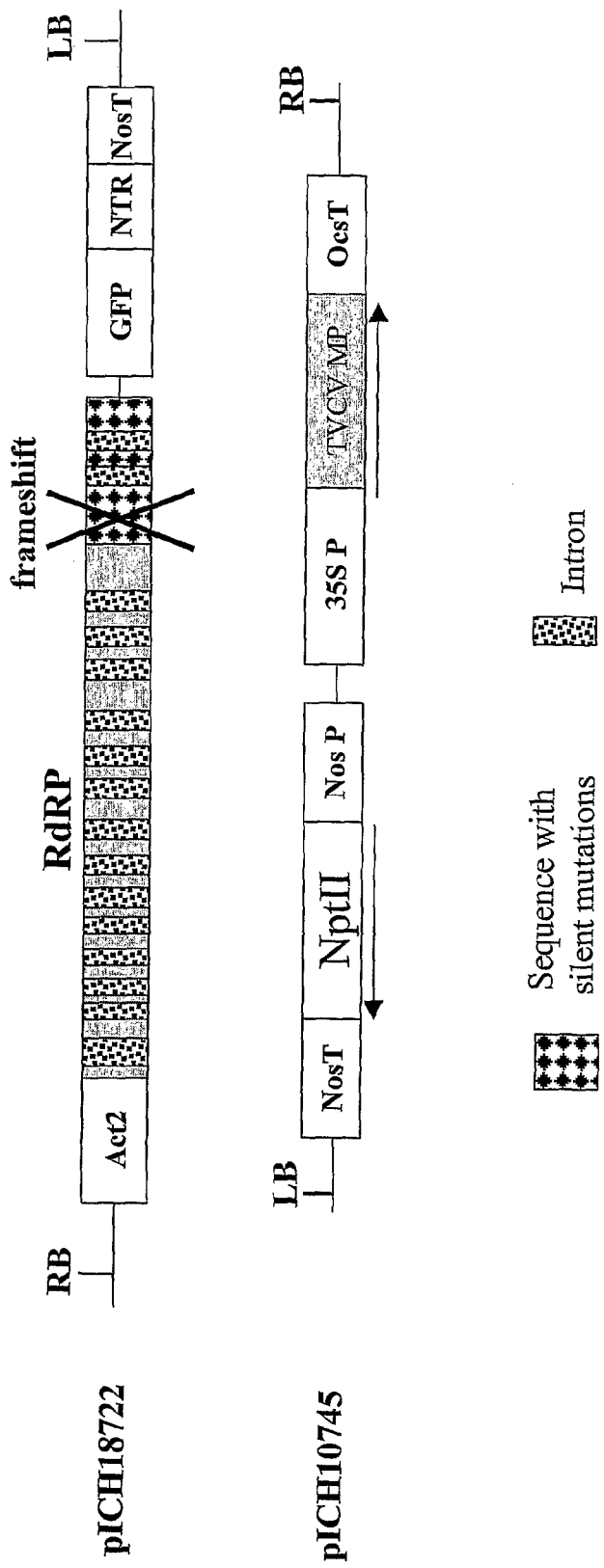
FIG. 5 show schematically the T-DNA regions of constructs pICH18722 and pICH10745. Act2—promoter of *Arabidopsis* ACTIN2 gene; RdRP viral RNA-dependent RNA polymerase; MP—viral movement protein; NTR—viral 3' non-translated region; GFP—green fluorescent protein; nosT—transcription termination region of nopaline synthase gene; nosP—transcription promoter of nopaline synthase gene; osc T—transcription termination region of octopine synthase gene; NPTII—coding sequence for neomycin phosphotransferase II gene; TVCV MP—movement protein of turnip vein-clearing virus.

We have surprisingly found that such an interdependency generated by partially delegating functions from one of said key components of the system to another one can be done such that the efficiency of the system is not affected negatively, but provides a better control over the whole process, thus increasing biosafety. The basic principle of the invention is shown in FIG. 1(A). A large scale protein production process based on agroinfiltration of viral replicon precursors can be performed on a transgenic host plant complementing either agrobacteria used for said agroinfiltration and/or said replicon in performing their functions required for expressing said protein of interest. One example of such a complementation for RNA replicon is described in EXAMPLE 4. In this example, a whole plant was transiently transformed with a heterologous DNA sequence encoding an RNA replicon lacking a functional movement protein (MP) (FIG. 5). This replicon is unable to move from cell to cell and consequently cannot provide a high yield in a plant host not having an expression cassette with a viral MP (pICH10745, FIG. 5).

If functions required for activation or operation of the viral replicon or for transient transfection are provided in trans by the plant or another strain of agrobacteria, no negative effect on the expression efficiency is found when the measures described herein for increasing the efficiency of RNA release from the nucleus into cytosol are used. Incorporation of plant introns into certain regions coding for viral RNA replicons, or removal or replacement of cryptic introns within sequences for replicon function can dramatically increase (at least $\times 10^2$ fold) the efficiency of said replicons in host plants. Such increase in efficiency was reflected in at least one easily measurable parameter: relative proportion of cells showing replication of said vector, i.e. in an increased frequency of replicon formation. Such optimisation of initiation of RNA replicon formation led to the ability of synchronized switching on of expression of a sequence of interest essentially in a whole plant, resulting in a dramatically increased yield of the protein of interest in shorter time than for a non-modified vector. EXAMPLES 6-14 of this invention describe the approach of improving said vectors in order to increase the efficiency of RNA viral vector release from nucleus into cytosol. Detailed account of viral vectors improvement was recently published by Marillonnet and colleagues (2005, *Nature Biotechnol.*, 23, 718-723). This improvement is an important embodiment of this invention, as it allows to exchange the functions between the RNA replicon, the plant host, and agrobacteria in an efficient way. Interestingly, such improved TMV-based vectors work efficiently in plant species other than *Nicotiana* like *Petunia hybrida, Brassica campestris, B. juncea* as well as cress, arugula and mustard. The best expressing non-*Solanaceae* species is Strawberry spinach, *Chenopodium capitatum*. *Asteraceae* like lettuce (notably seedlings) and sunflower as well as *Cucurbitaceae* cucumber indicate that several species from different plant families can be used successfully, preferably after additional optimization of the method.

Despite of publications concerning the increase of nuclear transgene expression by incorporation of introns in coding regions of recombinant DNA (Mascarenhas et al., 1990, *Plant Mol. Biol.*, 15, 913-920; Bourdon et al., 2001, *EMBO Reports*, 2, 394-398; Rose, A B., 2002, *RNA*, 8, 1444-1453; U.S. Pat. No. 5,955,330), there is no hint in the prior art showing that incorporation of introns into viral RNA replicon precursors would have any positive effect on the frequency of viral replicon formation and on the level of expression of a sequence of interest from said replicon. This effect is surprising considering that nuclear mRNA transcription and viral RNA replication take place in different sub-cellular compartments. Even if the cDNA copy of an RNA replicon is placed in the nucleus, only the first copy of the viral replicon precursor is produced in the nucleus and then amplified in the cytoplasm under conditions different from those in the nucleus. In the prior art, the use of introns for preventing the cytotoxic effect of "leaky" expression of viral genes in *E. coli* during cloning with wild type virus cDNAs was described (Johansen, I. E. 1996, *Proc. Natl. Acad. Sci. USA*, 93, 12400-12405; Yang et al., 1998, *Arch. Virol.*, 143, 2443-2451; Lopez-Moya & Garcia, 2000, *Virus Res.*, 68, 99-107). There is no hint that intron inclusion can increase the frequency of replicon formation from a viral cDNA clone.

The present invention provides a method for increasing fundamentally the frequency of RNA virus-derived replicon formation, said replicons are derived by transcription of a DNA precursor and designed for the expression of sequences of interest. Said method overcomes the limitations of existing viral vector-based expression systems, such as size limitation for heterologous sequences to be expressed and high instability of said vectors. Further, said method offers better biosafety characteristics and allows to design leakage-proof control over transgene expression (zero expression level in non-induced state), as such a design is an integrated part of the strategy for designing said RNA virus-derived replicon. By providing a high frequency of RNA virus-derived replicon formation, the approach described herein allows for a rapid initiation of the expression of a sequence of interest in an entire plant or in a part of a plant like leaves containing a heterologous DNA sequence encoding said RNA replicon. By practicing the invention, the performance of practically any plant RNA virus-derived replicon designed for the expression of a heterologous sequence of interest via agroinfiltration of a plant or plant leaves can be improved significantly by a dramatic increase of the frequency of replicon formation.

DNA and RNA viruses belonging to different taxonomic groups are suitable for constructing RNA replicons according to this invention. A list of DNA and RNA viruses to which this invention can be applied, is presented below. Taxa names in quotes (and not in italic script) indicate that this taxon does not have an ICTV international approved name. Species (vernacular) names are given in regular script. Viruses with no formal assignment to genus or family are indicated):

DNA Viruses:

Circular dsDNA Viruses: Family: Caulimoviridae, Genus: Badnavirus, Type species: commelina yellow mottle virus, Genus: Caulimovirus, Type species: cauliflower mosaic virus, Genus "SbCMV-like viruses", Type species: Soybean chloroticmottle virus, Genus "CsVMV-like viruses", Type species: Cassava vein mosaicvirus, Genus "RTBV-like viruses", Type species: Rice tungro bacilliformvirus, Genus: "Petunia vein clearing-like viruses", Type species: Petunia vein clearing virus;

Circular ssDNA Viruses: Family: Geminiviridae, Genus: Mastrevirus (Subgroup I Geminivirus), Type species: maize streak virus, Genus: Curtovirus (Subgroup II Geminivirus), Type species: beet curly top virus, Genus: Begomovirus (Subgroup III Geminivirus), Type species: bean golden mosaic virus;

RNA Viruses:

ssRNA Viruses: Family: Bromoviridae, Genus: Alfamovirus, Type species: alfalfa mosaic virus, Genus: Ilarvirus, Type species: tobacco streak virus, Genus: Bromovirus, Type species: brome mosaic virus, Genus: Cucumovirus, Type species: cucumber mosaic virus;

Family: Closteroviridae, Genus: Closterovirus, Type species: beet yellows virus, Genus: Crinivirus, Type species: Lettuce infectious yellows virus, Family: Comoviridae, Genus: Comovirus, Type species: cowpea mosaic virus, Genus: Fabavirus, Type species: broad bean wilt virus 1, Genus: Nepovirus, Type species: tobacco ringspot virus;

Family: Potyviridae, Genus: Potyvirus, Type species: potato virus Y, Genus: Rymovirus, Type species: ryegrass mosaic virus, Genus: Bymovirus, Type species: barley yellow mosaic virus;

Family: Sequiviridae, Genus: Sequivirus, Type species: parsnip yellow fleck virus, Genus: Waikavirus, Type species: rice tungro spherical virus; Family: Tombusviridae, Genus: Carmovirus, Type species: carnation mottle virus, Genus: Dianthovirus, Type species: carnation ringspot virus, Genus: Machlomovirus, Type species: maize chlorotic mottle virus, Genus: Necrovirus, Type species: tobacco necrosis virus, Genus: Tombusvirus, Type species: tomato bushy stunt virus, Unassigned Genera of ssRNA viruses, Genus: Capillovirus, Type species: apple stem grooving virus;

Genus: Carlavirus, Type species: carnation latent virus; Genus: Enamovirus, Type species: pea enation mosaic virus, Genus: Furovirus, Type species: soil-borne wheat mosaic virus, Genus: Hordeivirus, Type species: barley stripe mosaic virus, Genus: Idaeovirus, Type species: raspberry bushy dwarf virus;

Genus: Luteovirus, Type species: barley yellow dwarf virus; Genus: Marafivirus, Type species: maize rayado fino virus; Genus: Potexvirus, Type species: potato virus X; Genus: Sobemovirus, Type species: Southern bean mosaic virus, Genus: Tenuivirus, Type species: rice stripe virus, Genus: Tobamovirus, Type species: tobacco mosaic virus, Genus: Tobravirus, Type species: tobacco rattle virus, Genus: Trichovirus, Type species: apple chlorotic leaf spot virus; Genus: Tymovirus, Type species: turnip yellow mosaic virus; Genus: Umbravirus, Type species: carrot mottle virus; Negative ssRNA Viruses: Order: Mononegavirales, Family: Rhabdoviridae, Genus: Cytorhabdovirus, Type Species: lettuce necrotic yellows virus, Genus: Nucleorhabdovirus, Type species: potato yellow dwarf virus;

Negative ssRNA Viruses: Family: Bunyaviridae, Genus: Tospovirus, Type species: tomato spotted wilt virus;

dsRNA Viruses: Family: Partitiviridae, Genus: Alphacryptovirus, Type species: white clover cryptic virus 1, Genus: Betacryptovirus, Type species: white clover cryptic virus 2, Family: Reoviridae, Genus: Fijivirus, Type species: Fiji disease virus, Genus: Phytoreovirus, Type species: wound tumor virus, Genus: Oryzavirus, Type species: rice ragged stunt virus;

Unassigned Viruses:

Genome: ssRNA, Species Garlic viruses A, B, C, D, Species grapevine fleck virus, Species maize white line mosaic virus, Species olive latent virus 2, Species: ourmia melon virus, Species Pelargonium zonate spot virus.

The general principle of the invention is shown in FIG. 1(A). Many different approaches can be used to practice this invention. Said approaches can be based on using agrobacterial mutants unable to provide for transient expression, said mutations can be complemented in trans by transgenic host plant or by a second *agrobacterium* strain.

Preventing agrobacteria from infecting susceptible plants is used herein for increasing the biosafety of the system, thus increasing the control over the process of transient expression. There are comprehensive studies concerning the mechanisms of agrobacterial T-DNA transfer into the plant host that can be successfully applied in this invention.

One possible approach is to confine the agrobacterial strain carrying said heterologous DNA sequence encoding the viral replicon specifically to an engineered plant host. The osa gene of plasmid pSA encodes the oncogenic suppressive activity protein that can suppress transient expression by suppressing the virE2 protein necessary for T-DNA transport and further integration into plant nuclear DNA (Lee, L-Y. et al., 1999, *J. Bacteriol.*, 181, 186-196). However, this suppression can be reversed either by mixing agrobactreria expressing the osa gene with agrobacteria carrying wild type virE2 but no osa gene, e.g. by complementing the mutant phenotype in trans. Similar results can be achieved by generating transgenic plants expressing virE2. The T-DNA is transported into plant cells as a single-stranded intermediate with VirD2 covalently bound to its 5' end, but virE2 is an important component of this process, as agrobacterial mutants lacking virE2 are not tumorigenic. The tumorigenicity of such mutants can be restored by inoculating transgenic plants expressing virE2 (Citovsky, V. et al. 1992, *Science*, 256, 1802-1805). Additionally, there are agrobacterial mutants which entirely depend on acetosyringone. In EXAMPLE 5 of this invention we describe a process of transient expression wherein the ability of the *Agrobacterium* strain carrying the heterologous DNA sequence of the invention depends on the genetically engineered plant host or on wild type agrobacteria for complementing the virE2 protein in trans. Also, the *A. rhizogenes* GALLS protein can complement the function of VirE2 (Hodges et al., 2004, *J. Bacteriol.*, 186, 3065-3077). Such a system provides for a significant improvement of the control of the spread of the heterologous DNA, thus increasing the biosafety of the system. As described in said example, practically no expression of the protein of interest (GFP) was detected after agroinfiltration of wild-type *N. benthamiana* plants with agrobacteria lacking virE2. However, GFP was efficiently expressed when a complementing host plant expressing virE2 was agroinfiltrated, or when wild type agrobacteria were agroinfiltrated in a mixture with an *Agrobacterium* strain having this first genetic modification. Actually, the efficiency of T-DNA delivery by agrobacteria lacking vir E2 was reduced about 10,000-fold compared to wild type agrobacteria or mutant agrobacteria complemented in trans (see example 5, FIG. 17).

The approaches for engineering systems with increased biosafety are not restricted to in trans complementation of the virE2 function. The virF gene can also be used similarly as virE2 for generating plant hosts competent for transient expression by complementing virF deficient agrobacteria (Regensburg-Tuink, A J. & Hooykaas, P J. 1993, *Nature*, 363, 69-71). Interestingly, the osa protein prevents secretion of both, the virE2 and the virF protein (Chen, L. et al., 2000, *Proc. Natl. Acad. Sci. USA*, 97, 7545-7550). Alternatively, the *Agrobacterium tumefaciens* IncP- or IncN-type conjugal transfer system can be introduced into different bacteria, *Esherichia coli* strain and said strain can provide for T-DNA transfer in the presence of a disarmed *A. tumefaciens* strain (Pappas, K M. & Winans, S C, 2003. *Appl Envir. Microbiol.*, 69, 6731-6739). The latter shows that there are many different possibilities to engineer systems with improved biosafety, said system having a competent acceptor host and a bacterial donor strain or strains (e.g. donor and helper strains) restricted to said competent host. This approach significantly limits the likelihood of undesired T-DNA transfer to other organsims.

In addition to the ability of agrobacteria to transfer T-DNA into plant cells, agrobacteria are also able, like many other bacteria, to transmit genetic material (usually extrachromosomal plasmid DNA) via conjugation to other bacterial cells. Such ability to transfer plasmid DNA (for example a binary vector) from an industrial *Agrobacterium* strain to other agrobacterial strains (for example wild type agrobacteria) might compromise the control over transgene(s) release into the environment. In many cases, such conjugative transfer is only possible if a binary vector carrying a T-DNA region with transgene(s) recombines with a disarmed Ti plasmid, as many binary vectors do not contain structural elements (e.g. oriT which stands for origin of transfer) necessary for conjugative transfer and can therefore be introduced into an agrobacterial strain only by direct transformation, but not via tri-parental mating based on conjugative transfer of binary plasmid from *E. coli* to an agrobacterial strain of interest. For review on different binary vectors, see Hellens, R., Mullineaux, Ph. & Klee, H. (2000, *Trend Plant Sci.*, 5, 446-451). However, even if binary vector does not contain oriT, there is still a probability of recombination between the binary vector and a residential disarmed Ti plasmid. Such recombination can lead to the formation of a plasmid containing a T-DNA region with transgenes, whereby said plasmid may be capable of conjugative transfer between different bacteria. Several genes are involved in conjugative transfer between agrobacterial cells (Cook et al., 1997, *J. Bacterol.*, 179, 1291-1297; Beck et al., 1989, *J. Bacteriol.*, 171, 5281-5289). However, the most essential regions (oriT, traG, traF) are all located on a residential Ti plasmid (Oger & Farrand, 2002, *J. Bacteriol.*, 184, 1121-1131; Farrand, Hwang & Cook, 1996, *J. Bacteriol*, 178, 4233-4247; Li & Farrand, 2000, *J. Bacteriol.*, 182, 179-188). Removal of said regions via homologous recombination will impair inter-bacterial conjugative transfer even in the case of homologous recombination between a residential Ti plasmid and the binary vector takes place. The design of agrobacterial strain lacking said region involved in conjugative transfer can be easily carried out following the descriptions provided in the mentioned above references and in the example 16 of this invention using standard molecular biology techniques. Example 16 shows (see also FIG. 20) that the deletion of genes involved in conjugative plasmid transfer does not effect the efficiency of T-DNA transfer form agrobacteria to plant cells.

A further approach for increasing the expression efficiency of the expression system according to the invention is the use of host cellular factors and agrobacterial factors that limit agrobacterial infection. Many such factors are described in reviews on *agrobacterium*-mediated stable plant transfection (Gelvin, S B. 2003, *Trends Biotechnol*, 21, 95-98; Gelvin, S B. 2003, *Microbiol. Mol. Biol. Rev.*, 67, 16-37). For example, it was found that overexpression of the *Arabidopsis thaliana* gene VIP1 in transgenic tobacco plants made said plants significantly more susceptible to transient and stable genetic transfection by agrobacterium (Tzfira, T., Vaidya, M. & Citovsky, V. 2002, *Proc. Natl. Acad. Sci. USA*, 99, 10435-10440). The factor improving the efficiency of plant transfection can be constitutive expression of agrobacterial virulence genes. Usually such genes are under the control of environmental factors or cascades triggering the expression of vir genes and can be turned on by phenolic compounds, sugars, changed pH. Said factors may cause VirA protein-mediated phosphorylation of VirG, which in turn activates the promoters of other vir genes. A mutation caused by a single amino acid substitution within VirG can cause constitutive expression of other vir genes independent of VirA (Hansen, G., Das, A. & Chilton, M D. 1994, *Proc. Natl. Acad. Sci. USA*, 91, 7603-7607). In this publication, transient expression experiments with the GUS reporter gene using a mutant VirG strain of agrobacteria detected a significant increase in the number of foci expressing GUS in tobacco and maize tissues. A similar effect was observed when multiple copies of the wild type VirG were used for promoting the transient expression efficiency in tobacco, but they actually were ineffective in maize. The authors suggest that such VirG mutant strains can be useful for transformation of recalcitrant plant species. This means that they are also useful for developing viral vector-based transient expression system for plant species, which usually are difficult to transform. The use of a VirG mutant gene as described above is a useful approach for increasing the efficiency of transient expression together with or independent of different chemical factors such as phenolic compounds (Melchers et al., 1989, *Mol. Microbiol.*, 3, 969-977), acetosyringone or opines stimulating T-DNA transfer into the plant cells (Berthelot et al., 1998, *Phytochemistry*, 49, 1537-1548).

Other factors that can significantly improve the biological safety of the transient expression system and process of the invention are the use of auxotrophic agrobacterial strains, since such auxotrophic strains have a reduced probability of surviving in the open environment. The generation of auxotrophic agrobacterial strains via X-ray treatment is described by Dirks & Peeters (U.S. Pat. No. 6,323,396). Several such strains (a methionine or cysteine requiring one or a histidine and adenine requiring one) were described in said patent. One of the mutants requiring methionine for growth is deficient in the function of homocysteine methyltransferase. Considering the availability of a complete agrobacterium genome sequence in the databases, it is straightforward to generate such mutant for any well-characterised (sequenced) *Agrobacterium* strain using gene replacement via homologous recombination instead of the less predictable results obtained via X-ray treatment. For example, the *Agrobacterium tumefaciens* C58 genome sequence (GeneBank Acc. No. NC 00305) contains the gene (gene ID 1135697) coding for 5-methyltetrahydropteroyl-triglutamate-homocysteine methyltransferase. Using the available sequence information, a mutated gene version can be generated and cloned together with flanking sequences into a suicide vector containing e.g. the counter-selectable marker gene sacBR (Berger & Christie, 1993, *J. Bacteriology,* 175, 1723-1734) for further delivery into agrobacteria and selection for auxotrophic mutant of interest (e.g. mutant deficient in methionine metabolism in case of mutated homocysteine methyltransferase gene). Many other mutants can be generated using the described approach and publicly available information concerning different auxotrophic agrobacterial strains. Collens and colleagues (*Biotechnol. Prog.* 20 (2004), 890-896) generated auxotrophic agrobacterial mutants by means of insertional mutagenesis. Such mutant strains are unable to grow in the absence of adenine, leucine, cysteine or thiamine. Some of these mutants have a decreased efficiency of T-DNA delivery, while others (cys-32) have an ability to deliver T-DNA into the plant cells that is even higher than wild type agrobacteria. Probable agrobacterial genes affected are very likely leuB, thiD and cysE and cysK. Of course, the choice of auxotrophic strain shall be based on its suitability for an efficient T-DNA transfer into the plant cell. Also, for a higher biosafety level (lover frequency of reversion to wild type) strains can be generated that are auxotrophic for two or more different nutrient supplements (e.g. with two or more mutated genes). The generation of auxotrophic agrobacterial strains (DleuB and DpyrE) is described in example 17.

In addition to mutant strains of agrobacteria that can only perform their required function (e.g. T-DNA transfer) and/or survive in the presence of trans-complementing factors (e.g. virE2 protein, addition of metabolic compound), approaches based on active biological containment (ABC) systems for bacterial cells can be used. An example of such system was described by Ronchel & Ramos (2001, *Appl. Environ. Microbiol.,* 67, 2649-2656). In said publication, the authors described an ABC system designed to control at will the survival or death of a bacterial population via induction of cell death in the absence of a pollutant. The system is based on the use of a killing gene, such as a porin-inducing protein encoded by the *E. coli* gef gene. Said gene was put under the control of the lacI-inducible promoter. LacI expression in said system is under control of a promoter that depends on environmental signals. Similar schemes with the use of other killing genes for design of an ABC sytem were described in numerous publications (e.g. Knudsen et al. (1995) *Appl. Environ. Microbiol.* 61, 985-991; Ronchel et al. (1998) *Appl. Environ. Microbiol* 64, 4904-4911; Torres et al. (2003) *Microbiology* 149, 3595-3601). Streptavidin-based containment systems were described by Szafranski and colleagues (1997, *Proc. Natl. Acad. Sci. USA* 94, 1059-1063) and Kaplan and colleagues (1999, *Biomol. Eng.,* 16, 135-140).

Alternatively, inducible systems functional in bacterial cells can be used to control the expression of the genes responsible a specific functions (e.g. T-DNA transfer or biosynthesis of metabolites such as amino acids etc.) Actually, instead of deleting the gene from bacterial cell in order to create the mutant strain (e.g. auxotrophic mutant or mutant deficient in virE2 gene function), said gene can be put under control of regulatable promoter. The expression of the gene of interest from such regulatable promoter can be controlled via application of complementing factor that in this case can be a small molecule like tetracycline or IPTG. Different modifications of bacterial regulatable systems based, for example, on well-described tet and lac repressors can be used to control the expression of gene of interest in agrobacterial cells.

In addition to *Agrobacterium*, this invention can be extended to other microorganisms engineered for transferring T-DNA into plant cells. For example, it was recently shown that symbiotic bacterial species outside the *Agrobacterium* genus can be modified to mediate gene transfer to a number of diverse plants (Broothaerts et al. (2005) *Nature,* 433, 629-633). These bacteria were made competent for gene transfer by acquiring both a disarmed Ti-plasmid and a binary vector.

It is known that plant RNA viruses (exceptions are viroids—small non-coding RNAs amplifying in plant cell nuclei—for a review see Diener, T. O., 1999, *Arch. Virol. Suppl.,* 15, 203-220; Flores, R., 2001, *CR Acad. Sci. III,* 324, 943-952) do not occur in the cell nucleus, but in the cytoplasm. Therefore, the sequences of RNA viruses are not adapted to withstand nuclear RNA processing due to the presence of motifs that might be involved in processing steps including transport of processed RNA in cytoplasm, in which pre-mRNAs, rRNA and tRNA precursors are involved. The processing events, such as 5' end capping, splicing, 3' end generation, polyadenylation, degradation, base and sugar modification as well as editing (in plastids and mitochondria) have been intensively studied. However, many elements of such events still remain unclear. The most dramatic changes to pre-mRNA in the nucleus happen during pre-mRNA splicing, the process by which intervening RNA sequences (introns) are removed from the initial transcript and exons are concomittantly ligated. Splicing is mediated by the splicesome, a complex structure comprising uridilate-rich small nuclear ribonucleoprotein particles. The splicesome carries out the splicing reaction in two consecutive steps: the first one—cleavage at the 5' splice site of upstream exon/intron junction leading to lariat formation, and second step—cleavage at the 3' splice site of intron/downstream exon junction followed by upstream and downstream exons ligation (for review see: Kramer, A., 1996, *Annu. Rew. Biochem.,* 65, 367-409; Simpson, G G. & Filipowicz, W. 1996, *Plant. Mol. Biol.,* 32, 1-41). The 5' and 3' splicing site dinucleotides (5'/GU; AG/3') flanking the intron sequences are highly conserved in higher plants and single G replacement might abandon the splicing activity at the site concerned. Surprisingly, despite of a high conservation of splicing sites between plants and animals, heterologous introns are usually not spliced or spliced incorrectly in plants (van Santen, V L. et al., 1987, *Gene,* 56, 253-265; Wiebauer, K., Herrero, J. J., Filipowicz, W. 1988, *Mol. Cel. BioL,* 8, 2042-2051). Considering that plant viral RNAs were not under evolutionary pressure to resist the nuclear RNA processing machinery, these RNAs are very likely to become subject of such processing, including splicing, once they are placed into the nuclear environment. This situation is completely different from that of RNA transcripts encoded by nuclear genes, as the latter transcripts are evolutionary adapted to preserve their functionality, despite of series of RNA modifications taking place in the nucleus. However, such modifications can have dramatic consequences for viral RNA replicon formation. Re-engineering of the plant virus in order to make expression vectors for heterologous genes might further add to the instability of RNA virus-based replicons, as it would add further elements that might interact with RNA sequences of viral origin, producing defective RNA that is unable to replicate. Our invention addresses these problems by subjecting the expression vector to modifications that significantly increase the frequency of functional RNA replicon formation, when the expression vector is introduced as a DNA precursor into plants or plant cells to provide for transient expression or for stable integration into plant chromosomal DNA. Modifications of virus-derived sequences may be the best solution for increasing the efficiency of RNA virus-based replicons. The modifications may be direct (e.g. within said RNA virus-derived sequences) or indirect (e.g. within the sequences of non-viral origin), but said indirect modifications may have a stabilizing effect on the sequences of viral origin. In this invention, we predominantly focus on modifications within the RNA virus derived sequences, as they are crucial for increasing the efficiency of RNA replicon formation.

Figure 2A:
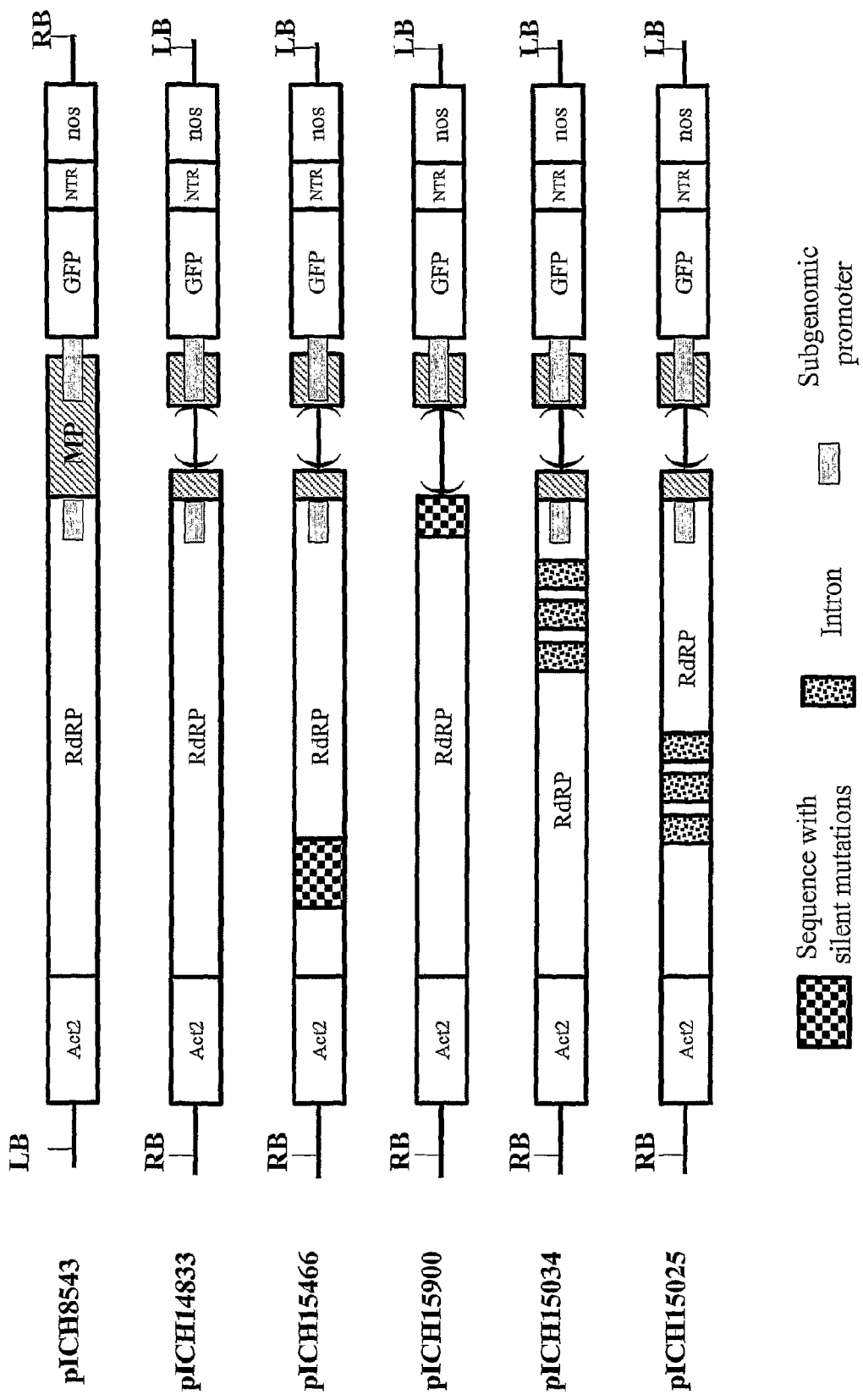
FIG. 2 (A, B, C) shows schematically viral constructs unmodified and modified according to the invention. Act2—promoter of *Arabidopsis* ACTIN2 gene; RdRP viral RNA-dependent RNA polymerase; MP—viral movement protein; NTR—viral 3' non-translated region; GFP—green fluorescent protein; interferon—human interferon alpha 2b; hGH—human growth hormone; nos—transcription termination region of nopaline synthase gene.

Surprisingly, our first attempt to find evidence that potentially problematic regions do exist, was successful and even more surprisingly, we obtained experimental confirmation by finding unexpectedly an improvement of orders of magnitude. An analysis of the sequence derived from the RNA virus of expression vector pICH8543 (EXAMPLE 1, FIG. 2A) using the Netgenell server program for the presence of cryptic introns and RNA splicing sites showed the presence of intron-like regions that might be spliced by the nuclear RNA processing machinery (see circled regions in FIG. 6). There are many other programs that can be used to identify potentially problematic regions (said selected localities) within plant viral RNA sequences, such as exon/intron prediction program or splicing signal prediction program for variety of organisms.

Figure 8:
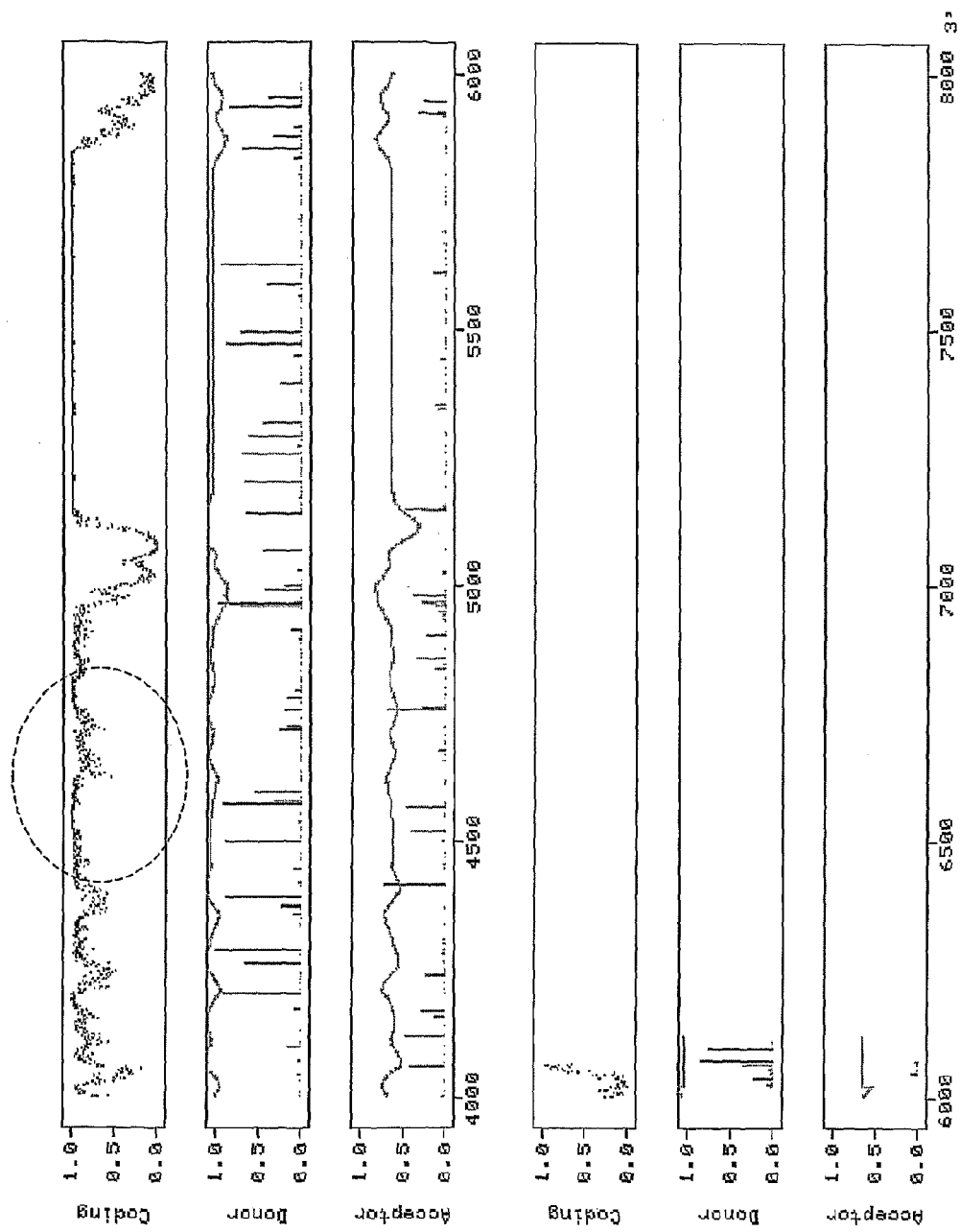

Considering that all existing programs are not ideal and are subject to mistakes, the potential problematic regions can also be determined experimentally. This can be done by analyzing the transcripts derived from the DNA vector under test in a nuclear environment with the help of RT-PCR (Frohman, M A., 1989, Methods Enzymol., 218, 340-356) or its more advanced version suitable for precise quantification of the concentration of different transcripts called real-time PCR (Gibson et al., 1996, *Genome Res.*, 6, 995-1001), preferably followed by sequencing of the PCR-amplified products. The function-conservative differences of the invention change dramatically the RNA profile, for example by replacing intron-like sequences with exon-like ones, e.g. by introducing silent mutations with replacement of A/U-rich regions (intron-like) with G/C-rich regions (exon-like) (see FIG. 3, circled regions). Plant introns, unlike exons, are usually A/U rich (Csank, C. et al., 1990, *Nucl. Acid Res.*, 18, 5133-5141; Goodall & Filipowicz, 1989, *Cell*, 58, 473-483), but there are exceptions, for example when in monocotyledonous plants G/C rich introns were found (Goodall & Filipowicz, 1989, *Cell*, 58, 473-483; Goodall & Filipowicz, 1991, *EMBO J.*, 10, 2635-2644). For practicing this embodiment of the invention, the A/U rich regions include not only prolonged stretches of sequences of at least 20 nucleotides in length with at least 55% or more of A/U content, but also shorter stretches ("islands") of 6-19 nucleotides in a row of purely A/U-containing sequences. An A/U content within this invention means that all sequences which are more A- than U-rich, or only A-rich and vice-versa are covered by this definition. In EXAMPLE 6, we demonstrate that the modification of A/U rich region increases the number of GFP expressing cells at least 10-fold. This is demonstrated in FIG. 10 by comparing the areas agroinfiltrated with pICH15466 (modified vector, FIG. 2A) and pICH14833 (control vector, FIG. 2A). Removing the movement protein (MP) allows for an accurate count of primary cells possessing functional RNA replicons, as cell-to-cell movement from the site of primary infection to neighbouring cells does not take place. In EXAMPLE 7, the modification of another U-rich intron-like region containing many cryptic splice sites (FIG. 6B) and covering the subgenomic promoter of the movement protein (MP) was performed (FIG. 8, circled). This modification gave a dramatic effect on the increase of the frequency of replicon formation from viral vector pICH15900. As it was established by protoplasts counting experiments (EXAMPLE 7), the increase was approximately 100-fold in comparison with unmodified vector pICH14833 for both tested *Nicotiana* species—*N. benthamiana* and *N. tobacco* (see the corresponding infiltrated areas in FIG. 10, A, B). In general, by using the approaches described in this invention, we could increase the frequency of RNA replicon formation approx. 300-fold, i.e. increasing the proportion of cells with functional replicons from about 0.2% (control vector) to more than 50% (modified vector). We believe this is not the limit and reaching a frequency of 100% is very realistic.

Figure 10A:
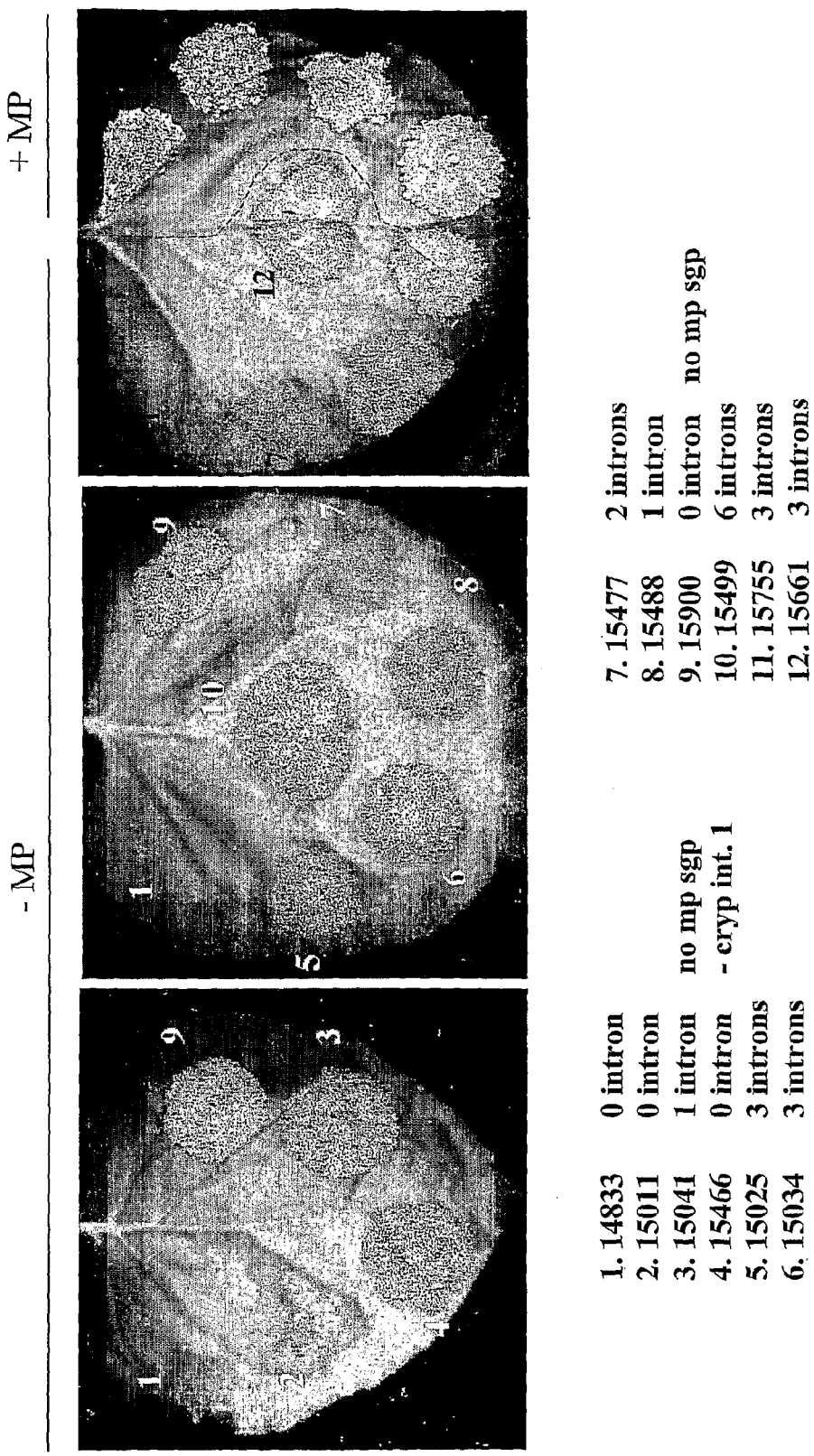
Figure 10B:
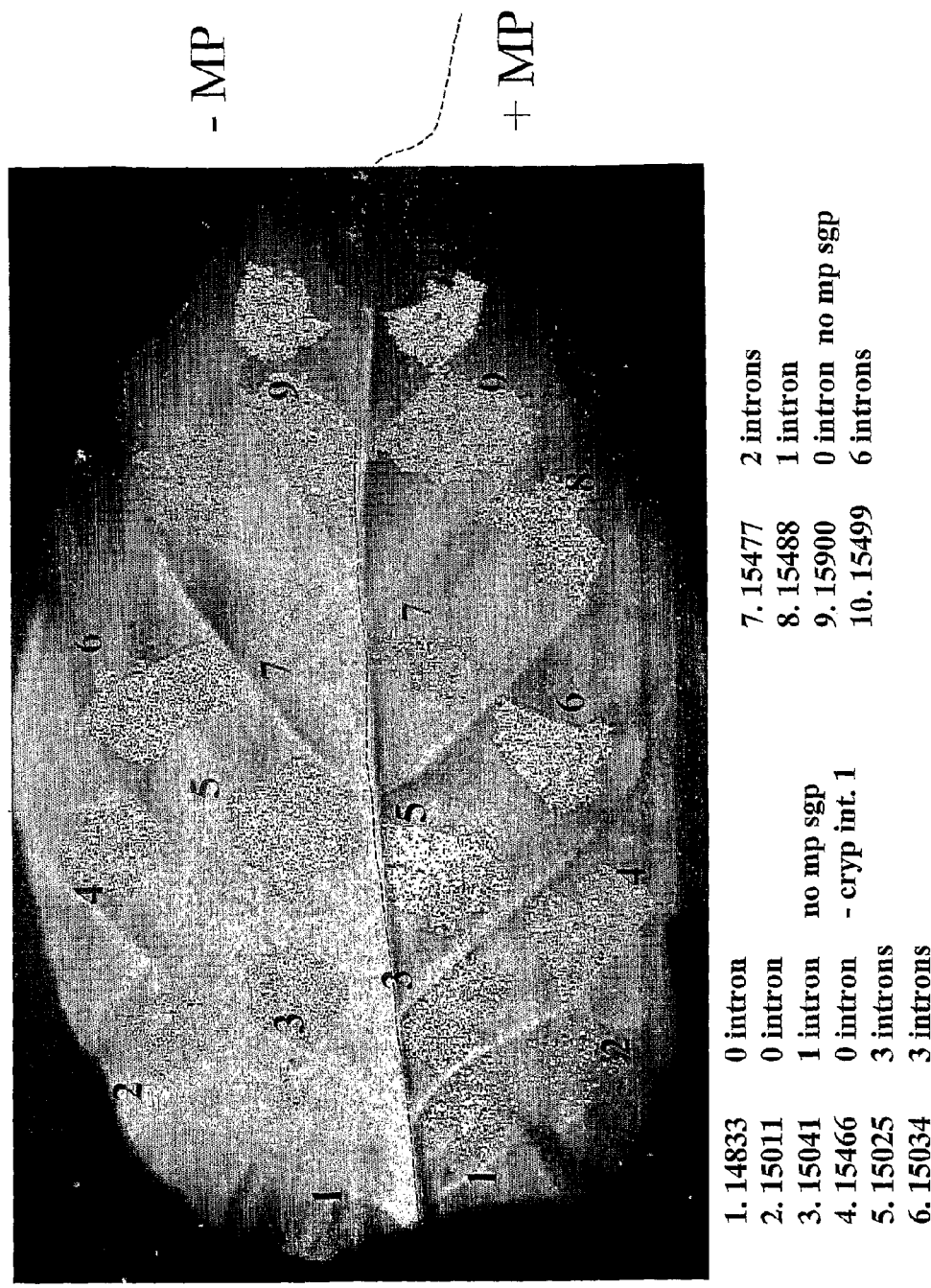
Figure 10C:
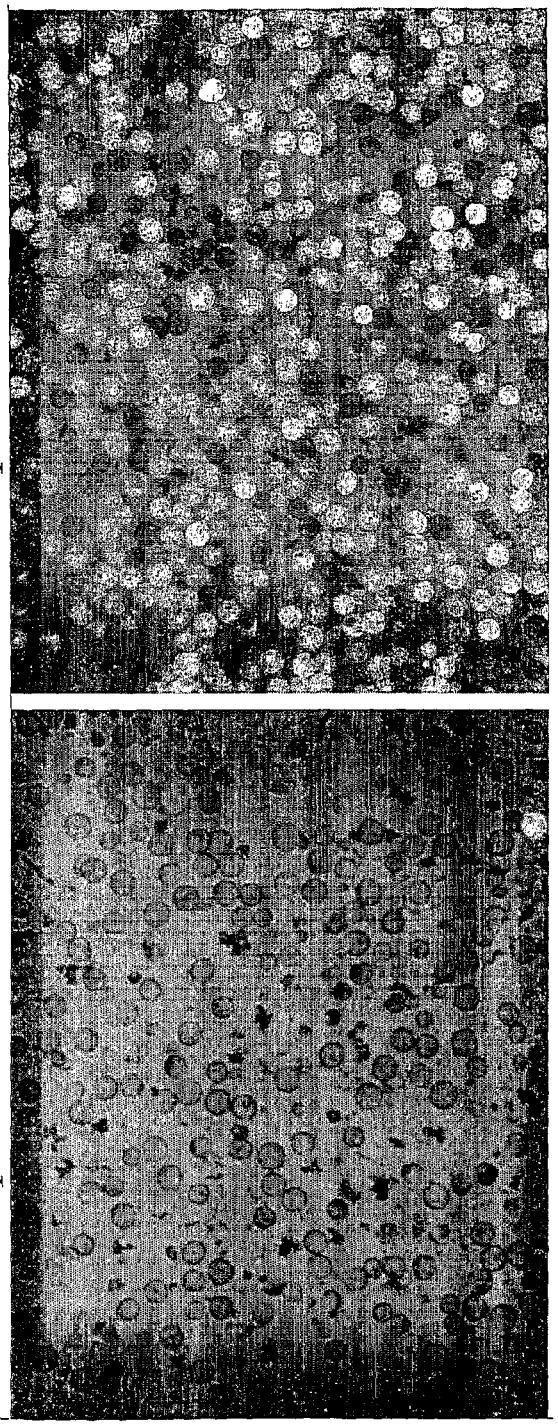
Figure 10C:
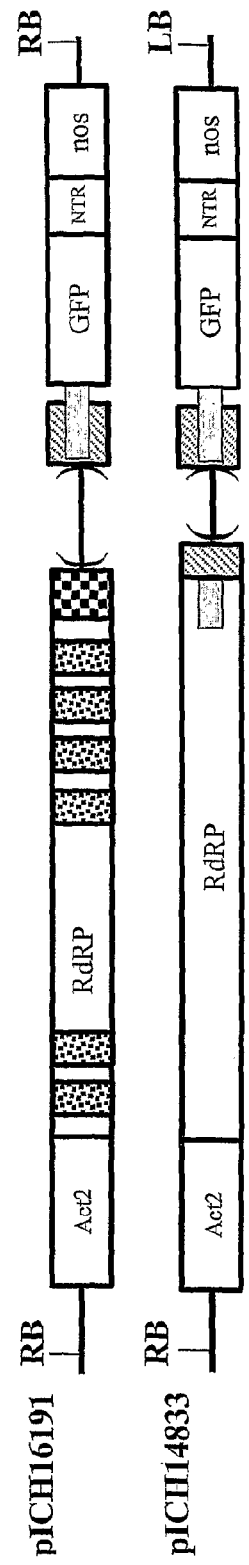
Figure 11:
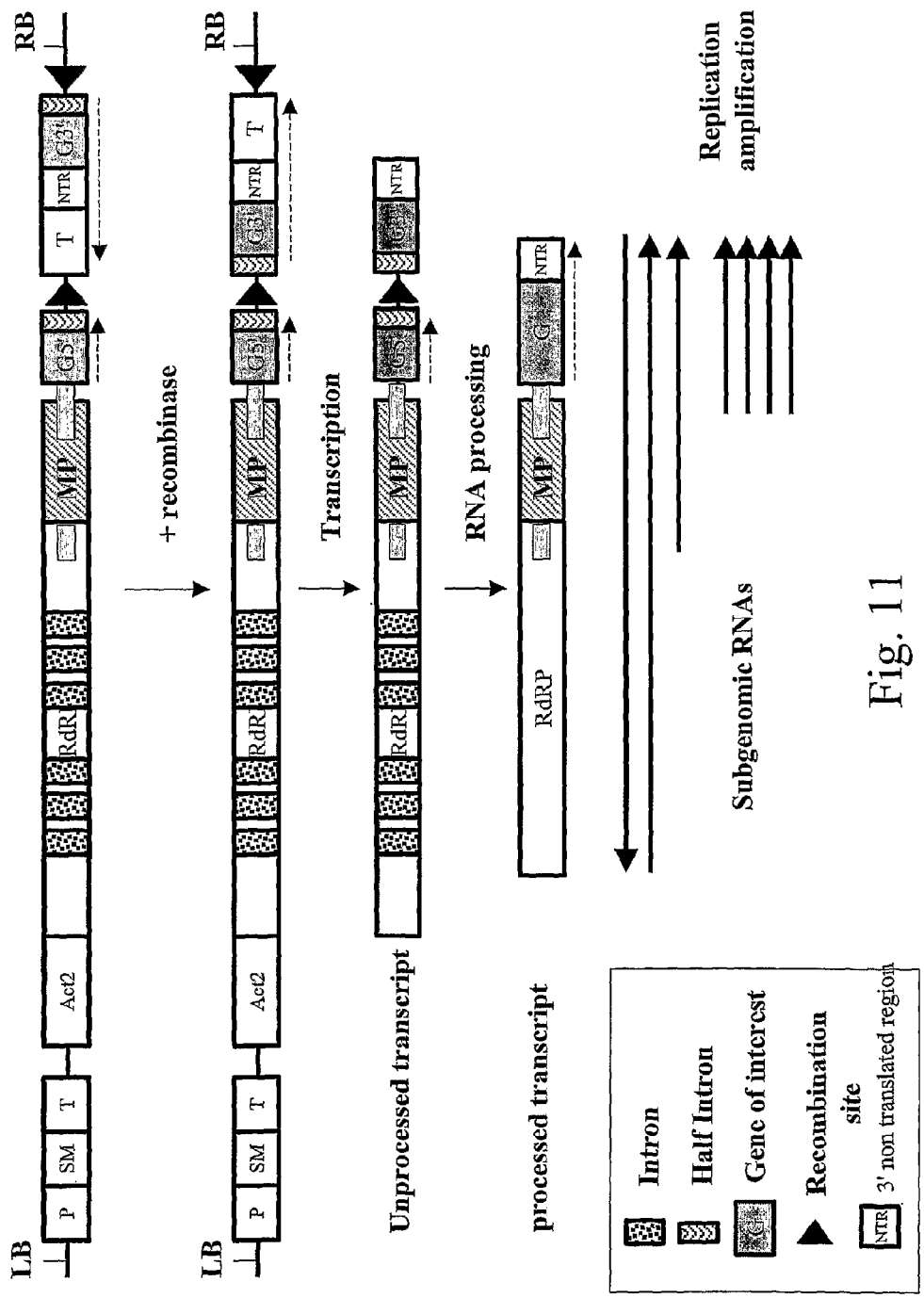

Such a high efficiency of replicon formation opens the door for expressing two or more different genes from two different RNA replicons within the same plant cell, e.g. co-expressing different genes by using plant RNA virus based vectors. The achievement of synchronized release of two or more replicons at same time in the same cell is crucial for such co-expression, as the principle "first come, first served" is especially true for viral vectors. Systemic or cell-to-cell movement does not help, as different viral vectors do normally not overlap in their areas of spread or such overlap is insignificant. Simple calculations demonstrate the importance of the technology described in this invention for achieving co-expression of two sequences of interest in the same plant cell from two replicons. In the case of a non-optimised viral vector with a frequency of functional replicon formation of 0.2% of all cells, the proportion of cells co-expressing two genes from two different RNA replicons will be 0.2×0.2=0.04%, while for the construct with increased frequency of functional RNA replicon formation (50% or ½ of all cells), said proportion of cells will be 0.5×0.5=0.25 or 25%, e.g. about 625-fold higher. With some of the best performing vectors (e.g. pICH16191, FIG. 10C), the proportion of cells having a functional replicon reaches ca. 90% (FIG. 10C, top right). This means that using such a vector for expressing two different sequences of interest from two independent replicons, co-expression can take place in 80% of all cells. It appears very likely that the technology can be further improved and that 100% co-expression can be reached.

It is worth to note that function-conservative differences in heterologous sequences of interest to be expressed from said RNA replicon might also be used to increase the frequency of RNA replicon formation, notably in combination with differences in sequences for replicon function. For example, modifications within said sequences of interest can be introduced that are necessary for formation and/or processing of said replicon.

Figure 2B:
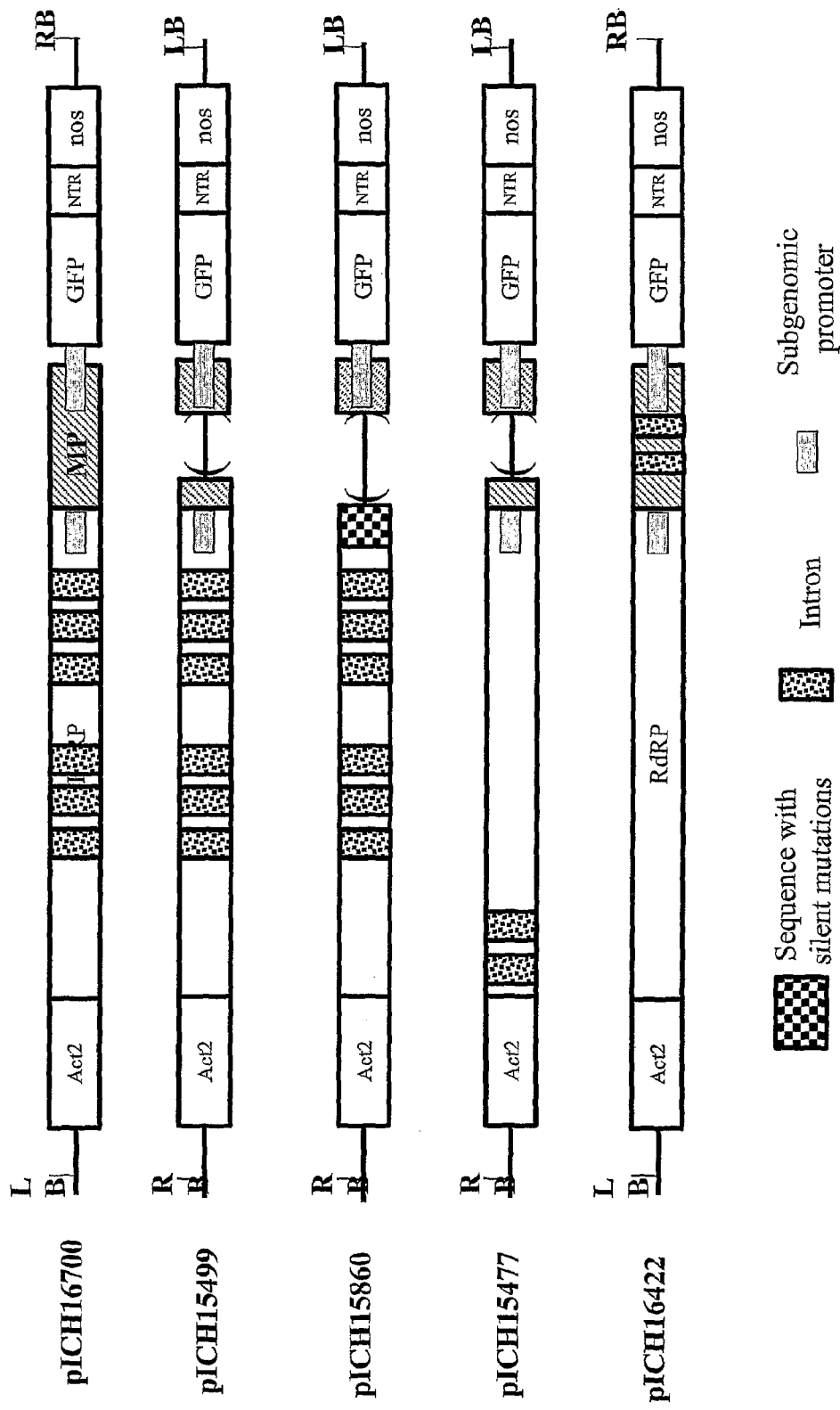
Figure 9A:
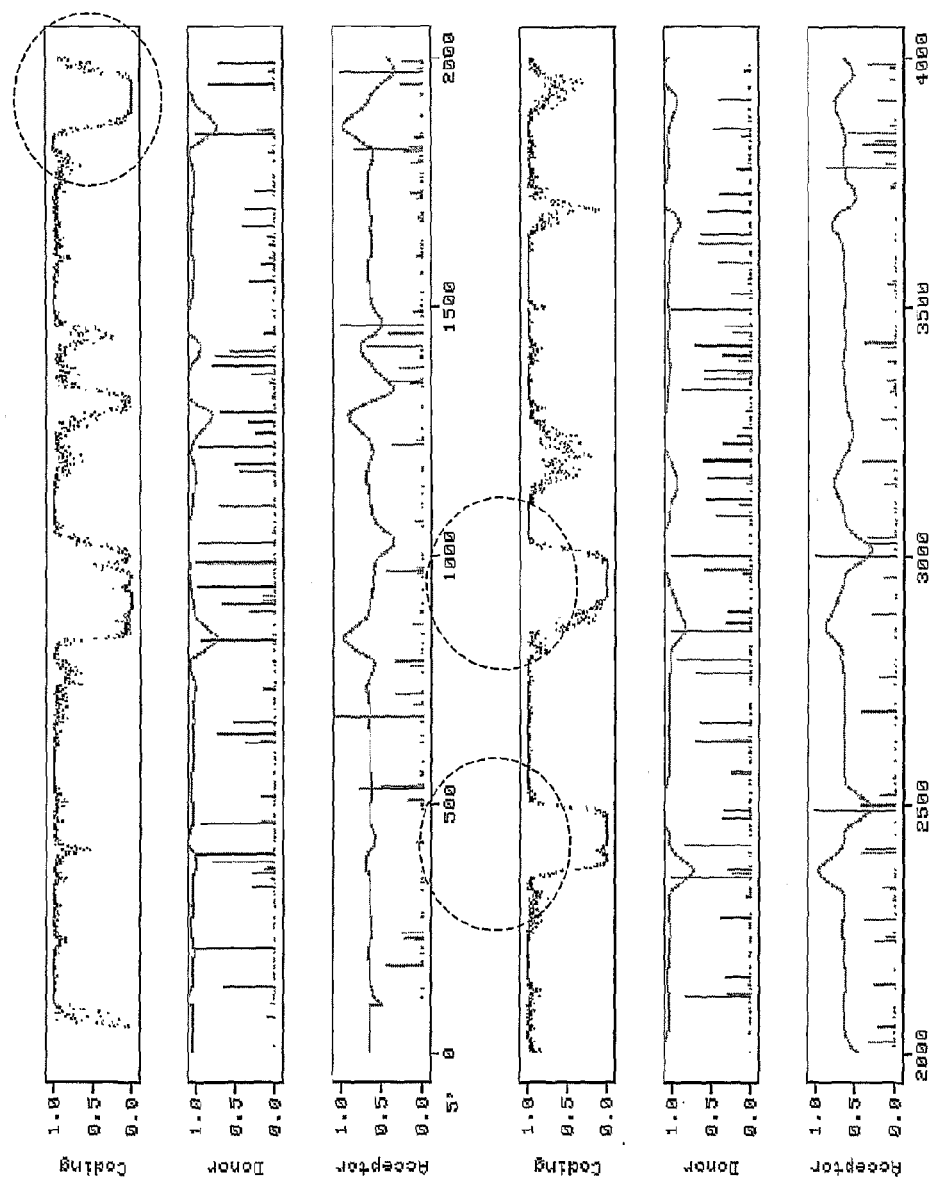
Figure 9B:
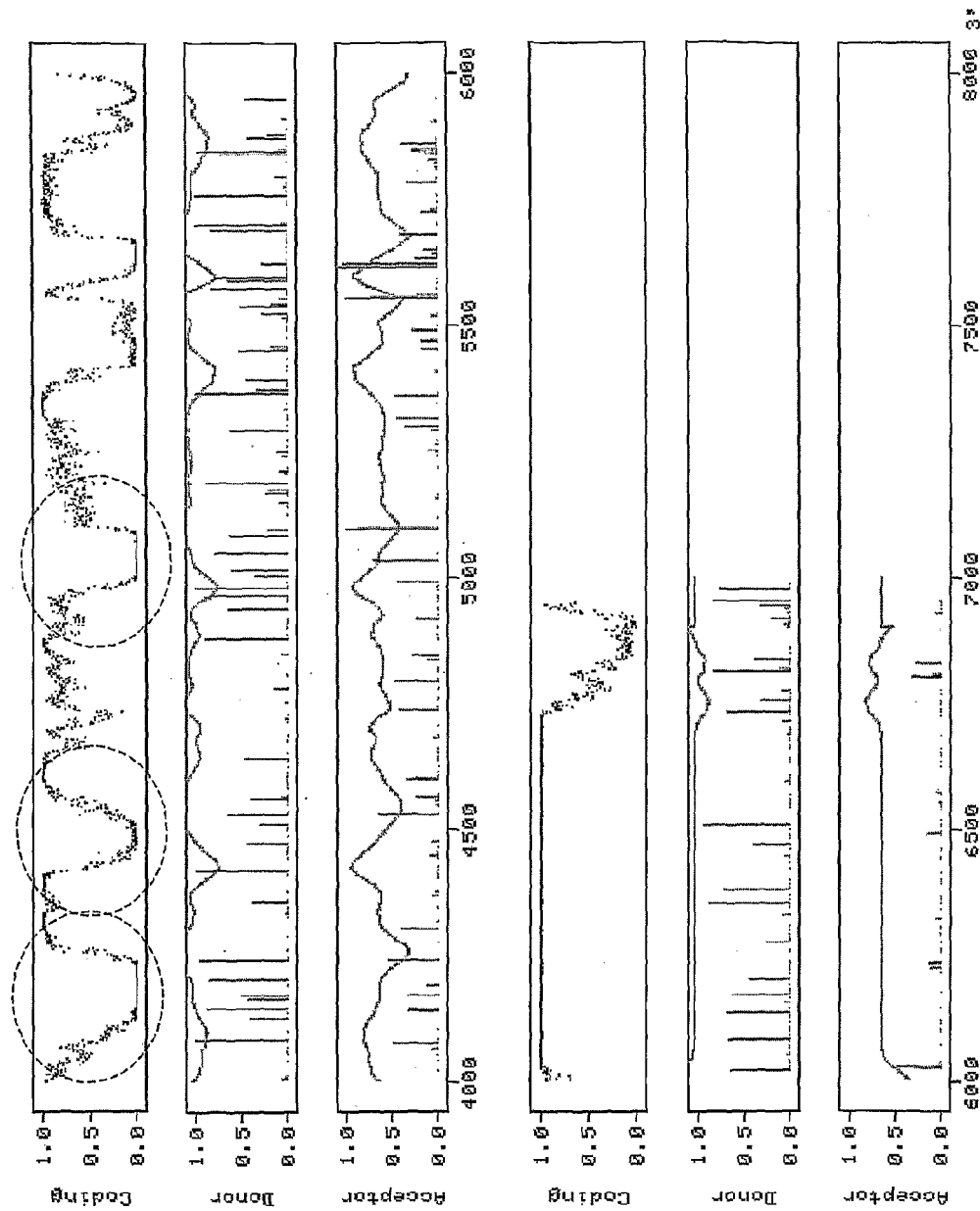

In another embodiment of this invention, the frequency of replicon formation was improved by inserting nuclear introns in said sequences for replicon function (EXAMPLE 8). The incorporation of introns into the coding region of a viral RNA-dependent RNA polymerase (RdRP) (EXAMPLES 8 and 12) resulted in a significant (at least 50-fold) increase in the frequency of replicon formation from (FIG. 10A,B) modified vectors (pICH15034, pICH15025, pICH15499 in FIG. 2 A,B). The RNA profile for a vector containing 6 inserted introns from *Arabidopsis* is shown in FIG. 9. In another example (EXAMPLE 11), insertion of introns in MP sequences increases the frequency of replicon formation at least 100 times.

Many nuclear introns can be used to practice this invention. Examples of such introns include but are not limited to the introns from rice tpi Act1, and salT genes (Rethmeier et al., 1997, *Plant J.*, 12, 895-899; Xu et al., 1994, *Plant Physiol.*, 100, 459-467; McElroy et al., 1990, *Plant Cell*, 2, 163-171); from the maize Adh1, GapA1, actin and Bz1 genes (Callis et al., 1987, *Genes Dev.*, 1, 1183-11200; Donath et al., 1995, Plant Mol. Biol., 28, 667-676; Maas et al., 1991, Plant Mol Biol, 16, 199-207; Sinibaldi &Mettler, 1992, in W E Cohn, K Moldave, eds, *Progress in Nucleic Acids Research and Molecular Biology*, vol 42, Academic Press, New York, pp 229-257), from petunia rubisco gene SSU301 (Dean et al., 1989, *Plant Cell*, 1, 201-208), *Arabidopsis* A1EF1α, UBQ10, UBQ3, PAT1 genes (Curie et al., 1993, *Mol. Gen. Genet.* 228, 428-436; Norris et al., 1993, *Plant Mol. Biol.*, 21, 895-906; Rose & Last, 1997, *Plant J*, 11, 455-464) and many others. Synthetic introns can also be used for this invention. The smallest usable introns or their parts may be limited to splice donor and acceptor sites which usually flank the internal intron sequences. Preferably, the introns should have a size of at least 50 nt., more preferably a size of 100 to 200 nt., but actually there are no limitations regarding the size of the introns. However, the size of the construct should be kept suitable for genetic manipulations. The origin of the intron, its structure and size may be selected individually depending on the nature of the vector. Transient expression experiments may be used for testing the efficiency of a chosen intron or the corresponding intron parts.

The modifications described above have a cumulative effect, e.g. if intron insertion(s) are combined with a modification of the MP subgenomic promoter, the increase in frequency of replicon formation can be approx. 300-fold (EXAMPLE 9). The preferred regions for intron insertions in order to have an increase in the frequency of RNA replicon formation are called selected localities herein. Such localities may contain "intron-like" structures. This is confirmed by the insertion of introns in MP, actually in close proximity to such a problematic region as the MP subgenomic promoter (EXAMPLE 11). A 100-fold increase in frequency of replicon formation was observed. Insertion of introns into "exon-like" regions does not have such a pronounced effect as insertion in said intron-like regions (EXAMPLE 10).

Different methods may be used for generating transgenic plant hosts with delegated functions required for making a plant host competent for transient expression of said sequence of interest, i.e. competent for complementing said defective *Agrobacterium* strain of the invention. Vectors may be transformed into plant cells by a Ti-plasmid vector carried by *Agrobacterium* (U.S. Pat. No. 5,591,616; U.S. Pat. No. 4,940,838; U.S. Pat. No. 5,464,763) or particle or microprojectile bombardment (U.S. Pat. No. 5,100,792; EP 00444882B1; EP 00434616B1). Other plant transformation methods can also be used like microinjection (WO 09209696; WO 09400583A1; EP 175966B1), electroporation (EP00564595B1; EP00290395B1; WO 08706614A1) or PEG-mediated transformation of protoplasts etc. The choice of the method for vector delivery may depend on the plant species to be transformed. For example, microprojectile bombardment is generally preferred for monocot transformation, while for dicots, *Agrobacterium*-mediated transformation gives better results in general.

In the examples described below, we used *Agrobacterium*-mediated delivery of vectors (said heterologous DNA sequence) into *Nicotiana* cells. However, said vectors may be introduced into the plants in accordance with any of the standard techniques suitable for stable or transient transformation or transfection of the plant species of interest. Transformation techniques for dicotyledonous are well known in the art and include *Agrobacterium*-based techniques and techniques which do not require *Agrobacterium*. Non-*Agrobacterium* techniques involve the uptake of exogenous genetic material directly by protoplasts or cells. These techniques include PEG or electroporation mediated uptake, particle bombardment-mediated delivery and microinjection. Examples of these techniques are described in Paszkowski et al., *EMBO J* 3, 2717-2722 (1984), Potrykus et al., *Mol. Gen. Genet.* 199, 169-177 (1985), Reich et al., *Biotechnology* 4:1001-1004 (1986), and Klein et al., *Nature* 327, 70-73 (1987). In each case, the transformed cells are regenerated to whole plants using standard techniques.

*Agrobacterium*-mediated transfection is a preferred technique for the transfection of dicotyledons because of its high transfection efficiency and its broad utility with many different species. The many crop species which may be routinely transformed by *Agrobacterium* include tobacco, tomato, sunflower, cotton, oilseed rape, potato, soybean, alfalfa and poplar (EP 0 317 511 (cotton), EP 0 249 432 (tomato), WO 87/07299 (Brassica), U.S. Pat. No. 4,795,855 (poplar)).

In the examples of this invention, we used agro-inoculation, a method of *Agrobacterium*-mediated delivery of T-DNA for transient expression of gene(s) of interest (Vaquero et al., 1999, *Proc. Natl. Acad. Sci. USA*, 96, 11128-11133). Agro-inoculation is an extremely useful tool not only for small-to-middle scale recombinant protein production systems, but as an element for vectors optimisation, allowing to obtain fast results with different variants of constructs.

For performing agro-infiltration, an overnight culture of *Agrobacterium* is generally prepared, as described in the prior art (Marillonnet et al., 2004, *Proc. Natl. Acad. Sci. USA.*, 101, 6853-6857). Usually, an overnight culture reaches an optical density (O.D.) of 3-3.5 units at a wavelength 600 nm and is diluted 3-5 times before agro-infiltration, yielding $5-9 \times 10^9$ colony forming units (Turpen et al., 1993, *J. Virol. Methods*, 42, 227-240). We have found that a $10^2$, $10^3$ and $10^4$ fold dilution also works very efficiently, especially in combination with sequences for replicon function having said function-conservative differences as described herein. Surprisingly, the vectors in infiltrated tobacco leaves further improved their performance giving better yield of GFP with increasing dilutions of the transforming Agrobacteria. For example, a $10^3$-fold dilution gave a better result than a $10^2$-fold dilution. A $10^2$-fold dilution provides a better GFP yield than a 10-fold dilution. A possible explanation for this phenomenon is the negative effect of highly concentrated *Agrobacterium* suspension on the function of a viral vector, e.g. on cell-to-cell movement, possibly as the result of a plant response to high concentrations of pathogenic bacteria. This phenomenon is of special value for large-scale industrial protein expression processes, as it allows to reduce the amount of agrobacteria required for recombinant protein production via agro-infiltration by at least one order of magnitude compared to prior art processes.

In EXAMPLE 13, a DNA precursor of an inactivated viral RNA-based replicon is shown. Said replicon is optimised according to the invention. In addition, the replicon contains a structure preventing expression of the sequence of interest, if agro-delivered into non-competent plant, e.g. plant that does not contain an expression cassette providing for recombinase stably incorporated into genomic DNA. Expression as well as formation of the functional RNA replicon can be triggered by flipping one part of the construct with the help of site-specific recombination. Said flipping can lead to the formation of two introns as well as to the assembly of a functional sequence of interest. The system described in EXAMPLE 13 shows not only the optimisation of a viral vector but also a way of achieving high biosafety standards with plant expression systems for expressing technical or pharmaceutical proteins.

Transcription of said recombinase can be under the control of an inducible or any other regulated (e.g. developmentally regulated) promoter. Inducible promoters can be divided into two categories according to their induction conditions: those induced by abiotic factors (temperature, light, chemical substances) and those that can be induced by biotic factors, for example, pathogen or pest attack. Examples of the first category are heat-inducible (U.S. Pat. No. 5,187,287) and cold-inducible (U.S. Pat. No. 5,847,102) promoters, a copper-inducible system (Mett et al., 1993, *Proc. Natl. Acad. Sci.*, 90, 4567-4571), steroid-inducible systems (Aoyama & Chua, 1997, *Plant J.*, 11, 605-612; McNellis et al., 1998, *Plant J.*, 14, 247-257; U.S. Pat. No. 6,063,985), an ethanol-inducible system (Caddick et al., 1997, *Nature Biotech.*, 16, 177-180; WO09321334), and a tetracycline-inducible system (Weinmann et al., 1994, *Plant J.*, 5, 559-569). One of the latest developments in the area of chemically inducible systems for plants is a chimaeric promoter that can be switched on by glucocorticoid dexamethasone and switched off by tetracycline (Bohner et al., 1999, *Plant J.*, 19, 87-95). For a review on chemically inducible systems see: Zuo & Chua, (2000, *Current Opin. Biotechnol.*, 11, 146-151) and Padidam, M (2003, *Curr. Opin. Plant Biol*, 6, 169-177). Other examples of inducible promoters are promoters which control the expression of patogenesis-related (PR) genes in plants. These promoters can be induced by treatment of a plant with salicylic acid, an important component of plant signaling pathways in response to pathogen attack, or other chemical compounds (benzo-1, 2,3-thiadiazole or isonicotinic acid) which are capable of triggering PR gene expression (U.S. Pat. No. 5,942,662).

Figure 12:
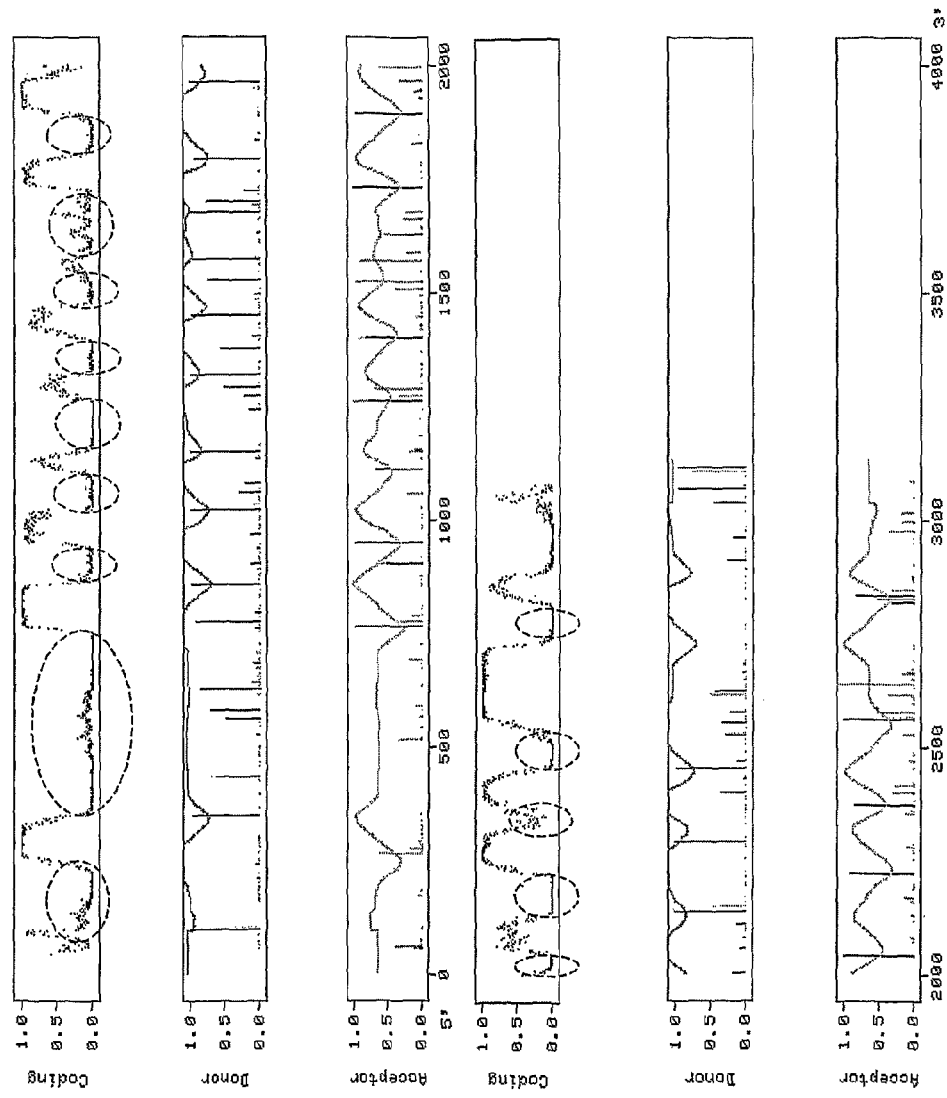
Figure 13A:
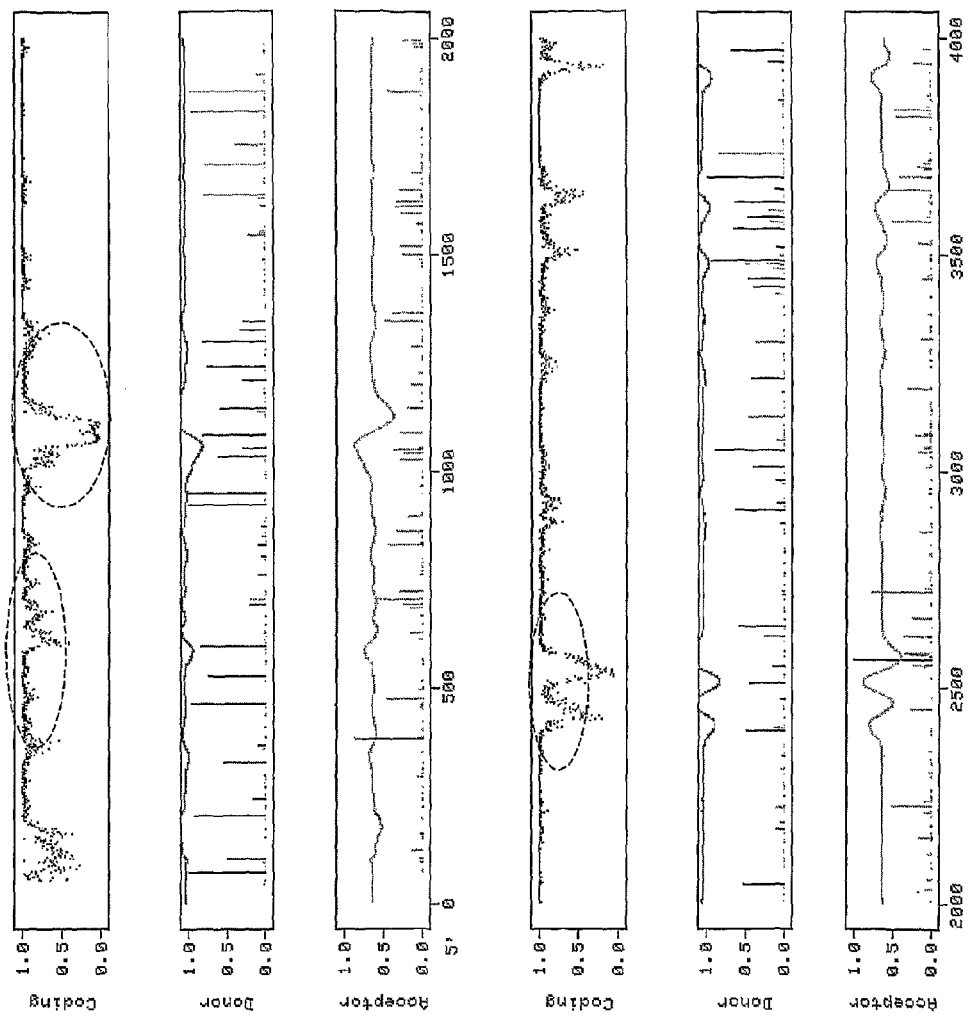
Figure 13B:
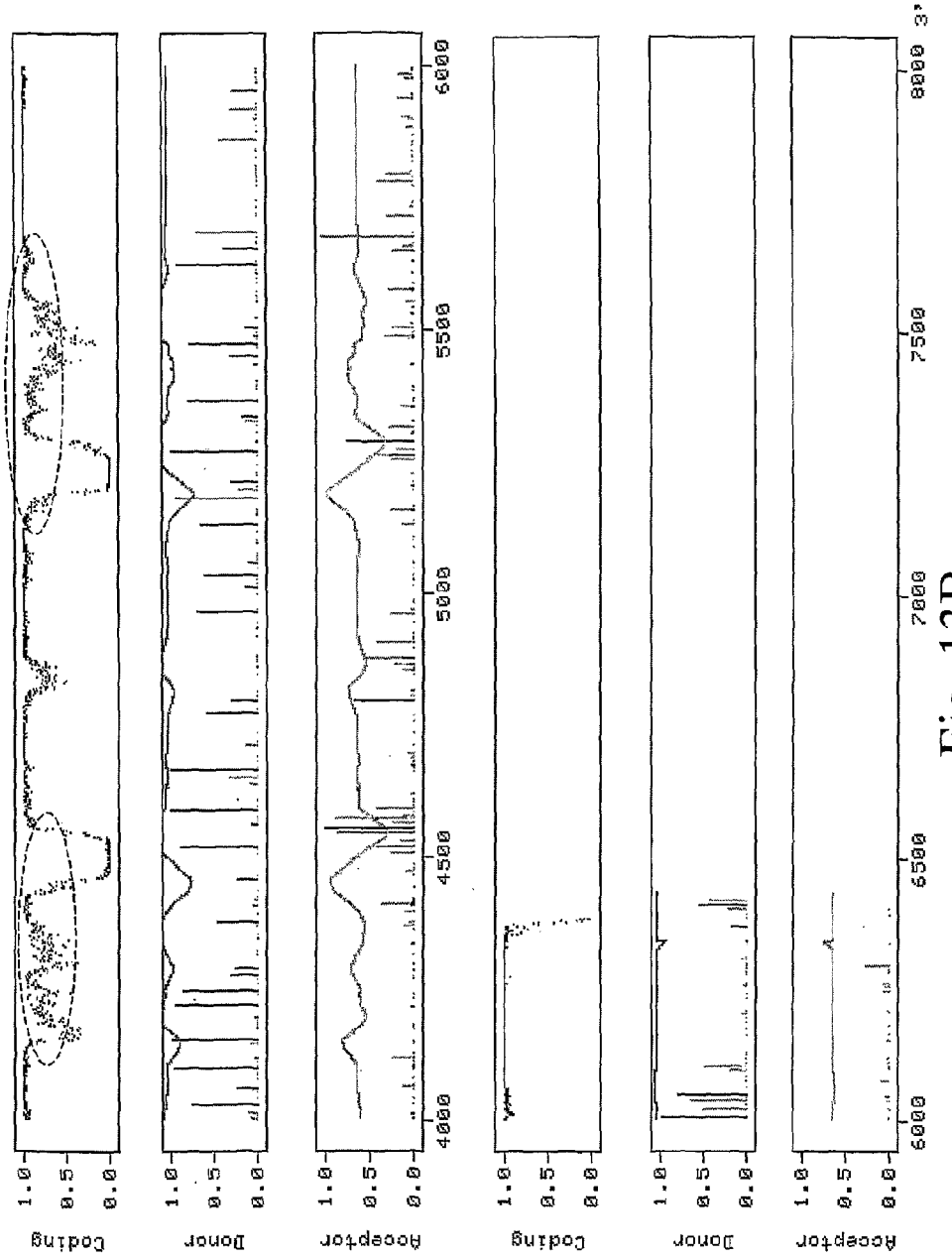
Figure 14A:
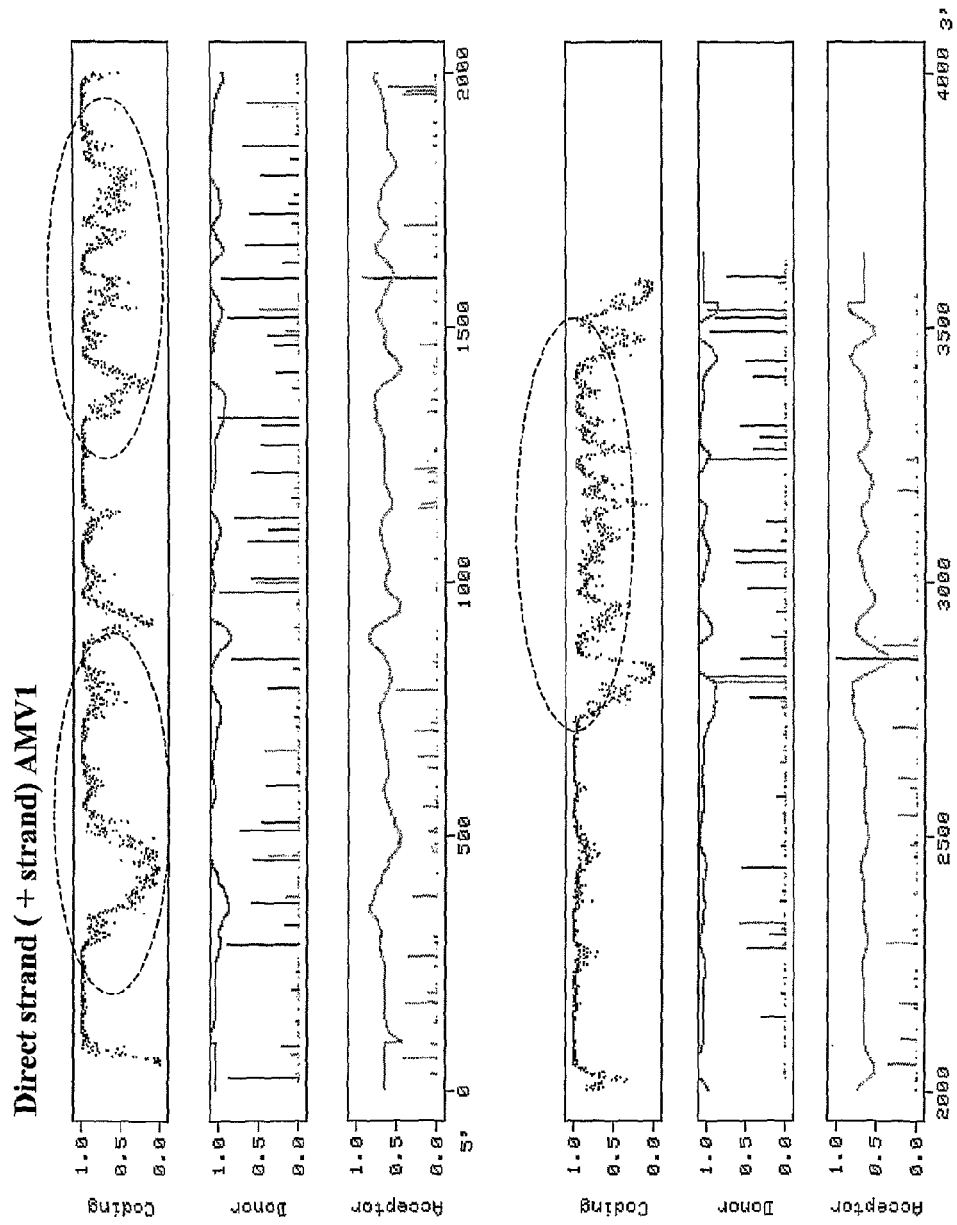
Figure 14B:
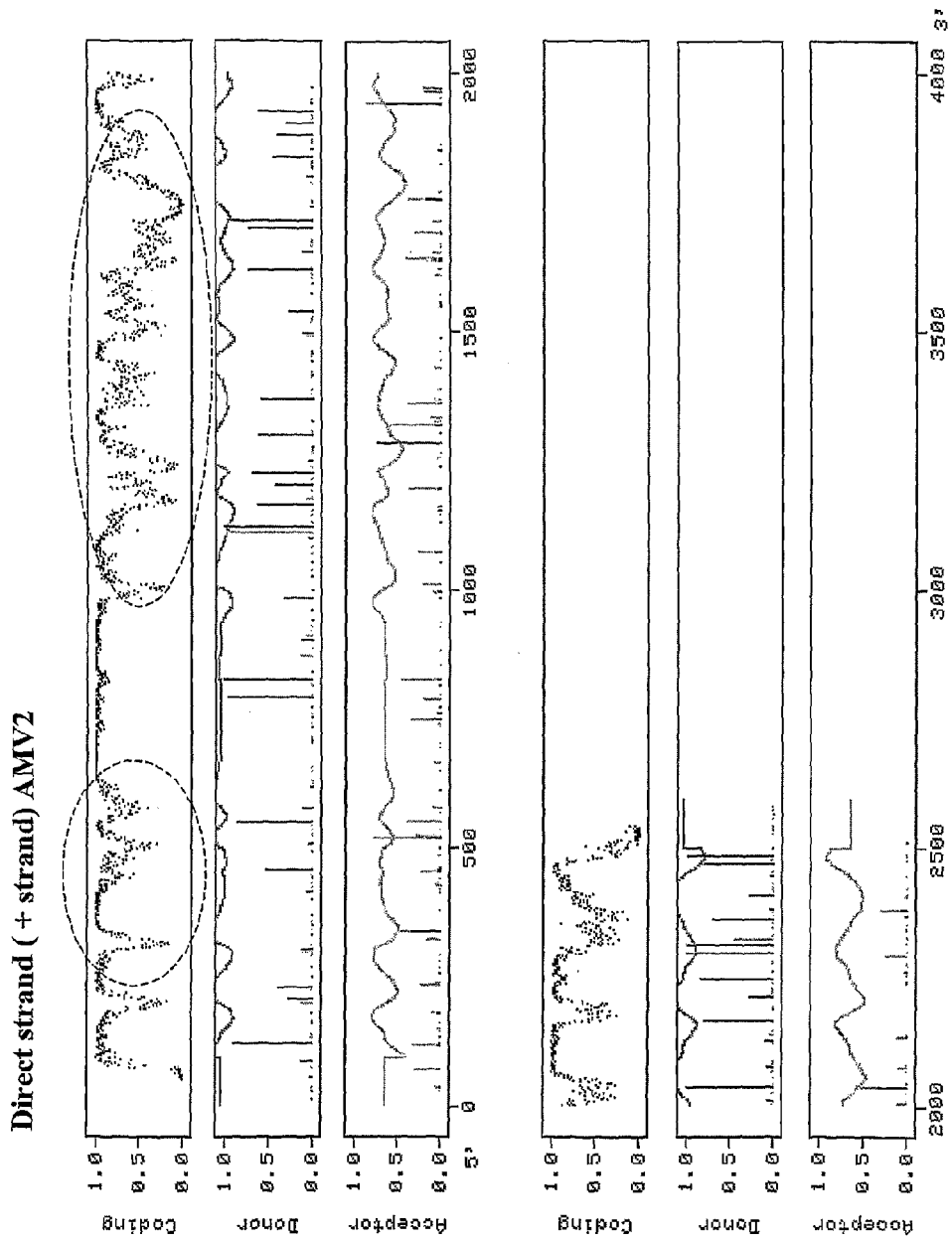
Figure 14C:
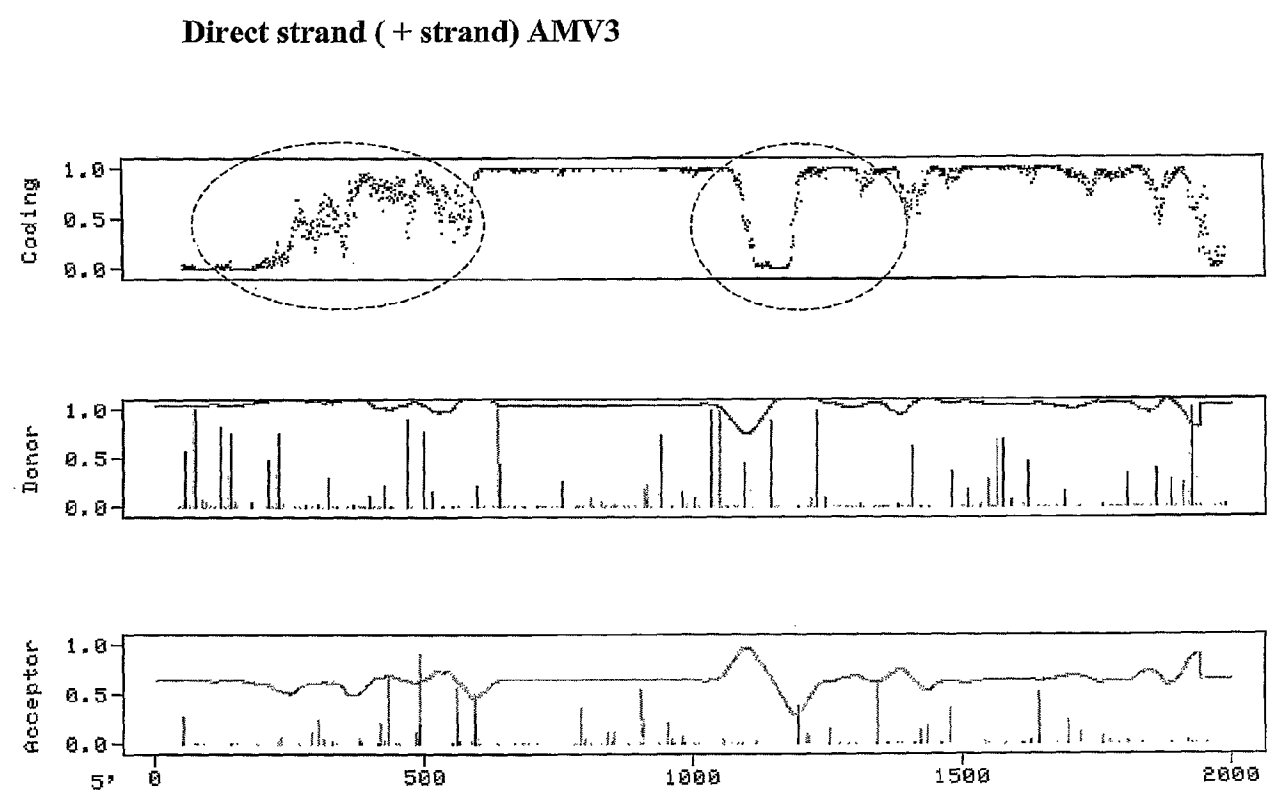

This invention is not limited to TMV-based vectors described in the examples, but also applicable to replicons based on other plant RNA viruses. The analysis of other plant viral RNA sequences (EXAMPLE 14, FIGS. 13, 14) shows selected localities similar to those described for TMV and the sequences of pre-mRNA of plant nuclear genes (FIG. 12). This is strong evidence that, using the approaches described in this invention, practically any plant RNA virus-derived replicon can be improved by removing/replacing problematic regions and/or inserting nuclear introns.

Proteins of interest, their fragments (functional or non-functional) and their artificial derivatives that can be expressed in plants or plants cells using the present invention include, but are not limited to: starch modifying enzymes (starch synthase, starch phosphorylation enzyme, debranching enzyme, starch branching enzyme, starch branching enzyme II, granule bound starch synthase), sucrose phosphate synthase, sucrose phosphorylase, polygalacturonase, polyfructan sucrase, ADP glucose pyrophosphorylase, cyclodextrin glycosyltransferase, fructosyl transferase, glycogen synthase, pectin esterase, aprotinin, avidin, bacterial levansucrase, *E. coli* gIgA protein, MAPK4 and orthologues, nitrogen assimilation/metabolism enzyme, glutamine synthase, plant osmotin, 2S albumin, thaumatin, site-specific recombinase/integrase (FLP, Cre, R recombinase, Int, SSVI Integrase R, Integrase phiC31, or an active fragment or variant thereof), oil modifying enzymes (like fatty acids desaturases, elongases etc), isopentenyl transferase, Sca M5 (soybean calmodulin), coleopteran type toxin or an insecticidally active fragment, ubiquitin conjugating enzyme (E2) fusion proteins, enzymes that metabolise lipids, amino acids, sugars, nucleic acids and polysaccharides, superoxide dismutase, inactive proenzyme form of a protease, plant protein toxins, traits altering fiber in fiber producing plants, Coleopteran active toxin from *Bacillus thuringiensis* (Bt2 toxin, insecticidal crystal protein (ICP), CrylC toxin, delta endotoxin, polypeptide toxin, protoxin etc.), insect specific toxin AaIT, cellulose degrading enzymes, E1 cellulase from *Acidothermus celluloticus*, lignin modifying enzymes, cinnamoyl alcohol dehydrogenase, trehalose-6-phosphate synthase, enzymes of cytokinin metabolic pathway, HMG-CoA reductase, *E. coli* inorganic pyrophosphatase, seed storage protein, *Erwinia herbicola* lycopen synthase, ACC oxidase, pTOM36 encoded protein, phytase, ketohydrolase, acetoacetyl CoA reductase, PHB (polyhydroxybutanoate) synthase, enzymes involved in the synthesis of polyhydroxylalkanoates (PHA), acyl carrier protein, napin, EA9, non-higher plant phytoene synthase, pTOM5 encoded protein, ETR (ethylene receptor), plastidic pyruvate phosphate dikinase, nematode-inducible transmembrane pore protein, trait enhancing photosynthetic or plastid function of the plant cell, stilbene synthase, an enzyme capable of hydroxylating phenols, catechol dioxygenase, catechol 2,3-dioxygenase, chloromuconate cycloisomerase, anthranilate synthase, *Brassica* AGL15 protein, fructose 1,6-biphosphatase (FBPase), AMV RNA3, PVY replicase, PLRV replicase, potyvirus coat protein, CMV coat protein, TMV coat protein, luteovirus replicase, MDMV messenger RNA, mutant geminiviral replicase, *Umbellularia californica* C12:0 preferring acyl-ACP thioesterase, plant C10 or C12:0 preferring acyl-ACP thioesterase, C14:0 preferring acyl-ACP thioesterase (luxD), plant synthase factor A, plant synthase factor B, D6-desaturase, proteins having an enzymatic activity in fatty acids biosynthesis and modifications, e.g. the peroxysomal β-oxidation of fatty acids in plant cells, acyl-CoA oxidase, 3-ketoacyl-CoA thiolase, lipase, maize acetyl-CoA-carboxylase, etc.; 5-enolpyruvylshikimate-3-phosphate synthase (EPSP), phosphinothricin acetyl transferase (BAR, PAT), CP4 protein, ACC deaminase, protein having posttranslational cleavage site, DHPS gene conferring sulfonamide resistance, bacterial nitrilase, 2,4-D monooxygenase, acetolactate synthase or acetohydroxyacid synthase (ALS, AHAS), polygalacturonase, Taq polymerase, bacterial nitrilase, many other enzymes of bacterial or phage origin including restriction endonucleases, methylases, DNA and RNA ligases, DNA and RNA polymerases, reverse trascryptases, nucleases (Dnases and RNAses), phosphatases, transferases etc.

The present invention can be used for the purpose of molecular farming and purification of commercially valuable and pharmaceutically important proteins including industrial enzymes (cellulases, lipases, proteases, phytases etc.) and fibrous proteins (collagen, spider silk protein, etc.). Human or animal health protein may be expressed and purified using described in our invention approach. Examples of such proteins of interest include inter alia immune response proteins (monoclonal antibodies, single chain antibodies, T cell receptors etc.), antigens including those derived from pathogenic microorganisms, colony stimulating factors, relaxins, polypeptide hormones including somatotropin (HGH) and proinsulin, cytokines and their receptors, interferons, growth factors and coagulation factors, enzymatically active lysosomal enzyme, fibrinolytic polypeptides, blood clotting factors, trypsin, trypsinogen, al-antitrypsin (AAT), human serum albumin, glucocerebrosidases, native cholera toxin B as well as function-conservative proteins like fusions, mutant versions and synthetic derivatives of the above proteins, thrombin, human gastric lipase, granulocyte-macrophage colony stimulating factor (GM-CMF), serpin, lactoferrin, lysozyme, oleosin, prothrombin, alpha-galactosidase.

The content of European patent application No. 04016011.1, the priority of which is claimed by the present patent application, is incorporated herein by reference in its entirety.

EXAMPLES

The following examples are presented to illustrate the present invention. Modifications and variations may be made as the case requires.

Example 1

Construction of a TMV-Based RNA Vector

Cloned cDNAs of the crucifer-infecting tobamovirus (cr-TMV; Dorokhov et al., 1994, *FEBS Lett.* 350, 5-8) and of the turnip vein-clearing virus (TVCV; Lartey et al., 1994, *Arch. Virol.* 138, 287-298) were obtained from Prof. Atabekov from Moscow University, Russia. A viral vector containing a green fluorescence protein (GFP) gene was made in several cloning steps. The resulting construct, pICH8543 (FIG. 2A), contains in sequential order: a 787 bp fragment from the *Arabidopsis* actin 2 promoter (ACT2, ref An et al, 1996, GenBank accession AB026654, bp 57962 to 58748), the 5' end of TVCV (GenBank accession BRU03387, bp 1 to 5455), a fragment of cr-TMV (GenBank accession Z29370, bp 5457 to 5677, with thymine 5606 changed to cytosine to remove the start codon of the coat protein, CP), sequences "taa tcg ata act cga g", a synthetic GFP (sGFP) gene, cr-TMV 3' nontranslated region (3' NTR; GenBank accession Z29370, bp 6078 to 6312), and finally the nopaline synthase (Nos) terminator. The entire fragment was cloned between the T-DNA left (LB) and right (RB) borders of pICBV10, a Carb$^R$ pBIN19-derived binary vector. pICH8543 was transformed into *Agrobacterium* strain GV3101 and infiltrated into a *Nicotiana benthamiana* leaf. Foci of GFP fluoresence that appeared 3 dpi grew and became confluent. Surprisingly, even though most cells in the infiltrated area finally expressed GFP due to viral replication and movement, only a fraction of the cells initiated viral replication, as detected by a number of independent GFP expressing foci. It becamce clear that the limiting factor is not DNA delivery to plant cells, since infiltration of *Nicotiana benthamiana* leaves with a GFP gene under control of the 35S promoter leads to GFP expression in almost every cell in the infiltrated area (not shown).

To confirm this observation, we made a viral vector construct containing a mutation in the MP. This construct, called pICH14833, is similar to pICH8543 but differs by a deletion of 389 bp in the MP gene, upstream of the EcoRI site present in the MP. The sequence of the NcoI to EcoRI fragment that includes this deletion is given in the annex as SEQ ID No. 1. The entire viral construct (from the ACT2 promoter to the Nos terminator) was cloned between the T-DNA left and right borders of pICBV49, a pBIN19-derived Kan$^R$ binary vector. Due to the deletion in the MP, replicons produced from this construct cannot move from cell to cell but are able to replicate autonomously within a cell. Cell to cell movement can be restored when MP is provided in trans, e.g. from a constitutive promoter such as the cauliflower mosaic virus 35S promoter.

To make an MP expression construct, the TVCV MP gene was amplified by PCR from cloned TVCV cDNA (GenBank accession Z29370, bp 4802 to 5628) and subcloned in a binary vector under control of the 35S promoter. The resulting construct, called pICH10745 (not shown), and pICH14833 were transformed into *Agrobacterium* strain GV3101 and were infiltrated in *Nicotiana benthamiana* leaves. Infiltration of pICH14833 alone led to the appearance of a few GFP expressing cells within the infiltrated area. By counting protoplasts prepared from the infiltrated area, we found that only one to three protoplasts expressed GFP from a total of 500 protoplasts (0.2 to 0.6%). Coinfiltration of pICH14833 and pICH10745 led to the formation of GFP-expressing foci that grew from each initial GFP-expressing cell. Ultimately, due to cell-to-cell movement, a large proportion of cells in the infiltrated area expressed GFP (FIG. 10A).

The same cloned cDNAs of the crucifer-infecting tobamovirus as described above (cr-TMV; Dorokhov et al., 1994, *FEBS Lett.* 350, 5-8) and of the turnip vein-clearing virus (TVCV; Lartey et al., 1994, *Arch. Virol.* 138, 287-298) obtained from Prof. Atabekov from Moscow University, Russia were used for constructing several additional viral vectors. A viral vector containing a green fluorescence protein (GFP) gene was made in several cloning steps. The resulting construct, pICH16707 (FIG. 2C), contains in sequential order: a 787 bp fragment from the *Arabidopsis* actin 2 promoter (ACT2, ref An et al, 1996, GenBank accession AB026654, bp 57962 to 58748), the 5' end of TVCV (GenBank accession BRU03387, bp 1 to 5455), a fragment of cr-TMV (GenBank accession Z29370, bp 5457 to 5677, with thymine 5606 changed to cytosine to remove the start codon of the coat protein, CP), sequences "taa tcg ata act cga g", a synthetic GFP (sGFP) gene, cr-TMV 3' nontranslated region (3' NTR; GenBank accession Z29370, bp 6078 to 6312), and finally the nopaline synthase (Nos) terminator. The entire fragment was cloned between the T-DNA left (LB) and right (RB) borders of pICBV29, a KanR pBIN19-derived binary vector. pICH16707 was transformed in agrobacterium strain GV3101. The transformed agrobacterium strain was grown in LB medium overnight until saturation. 200 µl of overnight cultures grown *Agrobacterium* were sedimented with a microcentrifuge at 8000 rpm for 3 minutes. The pellet was resuspended in 1 ml of a solution containing 10 mM MES (pH 5.5), 10 mM MgSO4 resulting in an OD of approximately 0.7. Leaves of greenhouse-grown *Nicotiana benthamiana* plants were infiltrated using a syringe without a needle. Foci of GFP fluorescence appeared 3 days after infiltration. The foci of fluorescence grew and became confluent several days later.

Figure 3:
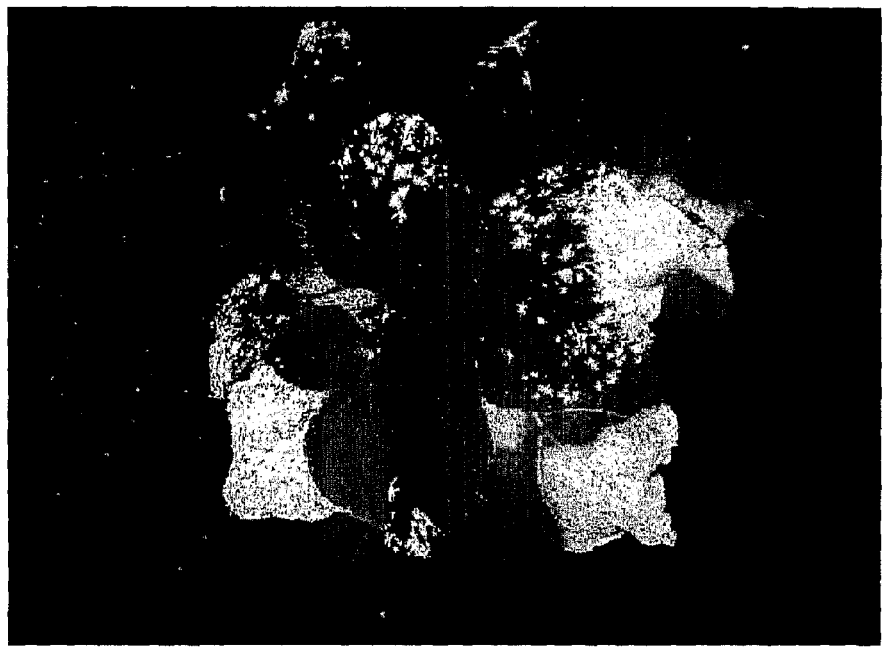
FIG. 3 shows a *Nicotiana benthamiana* plant under UV light 10 days after agro-infiltration with vector pICH16707.

A larger volume of infiltration solution (3 litres) was prepared, with agrobacteria at an OD of 0.3-0.4. A whole *Nicotiana benthamiana* plant was dipped into the solution with the pot in an upside-down position, and inserted in an exsiccator to apply vacuum for 1 to 2 minutes, until enough solution had penetrated the leaves. The plant was then removed and placed to recover in the greenhouse. After 3 to 4 days after infiltration, spots of fluorescence appeared in the infiltrated areas as in areas infiltrated by hand with a syringe. A picture is shown of such a plant 10 days after infiltration (FIG. 3).

RNA viruses such as tobamoviruses replicate in the cytoplasm and never enter the nucleus. Therefore, they have evolved in an environment where they are not exposed to the nuclear pre-mRNA processing machinery. As a result, RNA replicon transcripts generated in the nucleus from artificial viral constructs may not be recognized and processed properly by the RNA processing machinery. Moreover, RNA replicons from viral vectors are very large: approximately 7,000 nt in the case of the replicon based on TMV. Very few plant genes have such a large size and the majority of such genes contains introns that facilitate processing of the pre-mRNAs, export from the nucleus, and that improve the stability of the processed transcripts. We therefore hypothesized that modifications of the pre-mRNAs that would increase the efficiency of accurate processing and of export of correctly processed transcripts from the nucleus to the cytosol would lead to an increase of the number of cells that would initiate viral replication. It turned out that there are two approaches that can be used to make RNA virus-based vectors that can more efficiently initiate viral replication after DNA delivery to the nucleus: (1) one approach is the removal of sequence features that might induce unwanted processing events (such as alternative splicing events using cryptic splice sites, or premature termination events); (2) a second approach is the addition of introns to increase the amount of properly processed transcripts, to improve export of the RNA from the nucleus to the cytoplasm, and/or to improve stability of the transcripts.

Example 2

Construction of an Improved TMV-Based RNA Vector

Figure 4:
FIG. 4 shows 17 (A), 22 (B), 28 (C) and 35 (D) days old *Nicotiana benthamiana* plants under UV light 4 days after agro-infiltration with vector pICH18711.

To improve the speed at which the sequence of interest is expressed in infiltrated leaves, 16 arabidopsis introns, ranging in size from 91 to 443 nt, were added to the vector at positions 1 to 16: (position given relative to in TVCV sequence, GenBank accession BRU03387): 1, bp 209; 2, bp 423; 3, bp 828; 4, bp 1169; 5, bp 1378; 6, bp 1622; 7, bp 1844; 8, bp 2228; 9, bp 2589; 10, bp 2944; 11, bp 3143; 12, bp 3381; 13, bp 3672; 14, bp 3850; 15, bp 4299; 16, bp 4497; 17, bp 5099; 18, bp 5287; 19, bp 5444. The resulting construct, pICH18711 (FIG. 2C), was used for vacuum-infiltration of several Nicotiana benthamiana plants of different ages (17 to 35 days after sowing). GFP fluorescence appeared after two days and was very high at 6 days post infiltration. A picture is shown at 4 days after infiltration (FIG. 4). GFP fluorescence covered the entire leaf area much faster (4 to 6 days after infiltration) than with the non-improved vector pICH16707. A detailed description of improved viral vectors was recently published (Marillonnet et al., 2005, Nature Biotechnol., 23, 718-723).

Instead of an entire plant, a branch of a Nicotiana benthamiana plant (stem and leaves) was vacuum-infiltrated. The stem was left to recover by placing the base of the stem in a cup of water. GFP appeared in leaves three days later, showing that parts of a plant rather than an entire plant can be used for the expression of a gene of interest.

Example 3

Figure 2C:
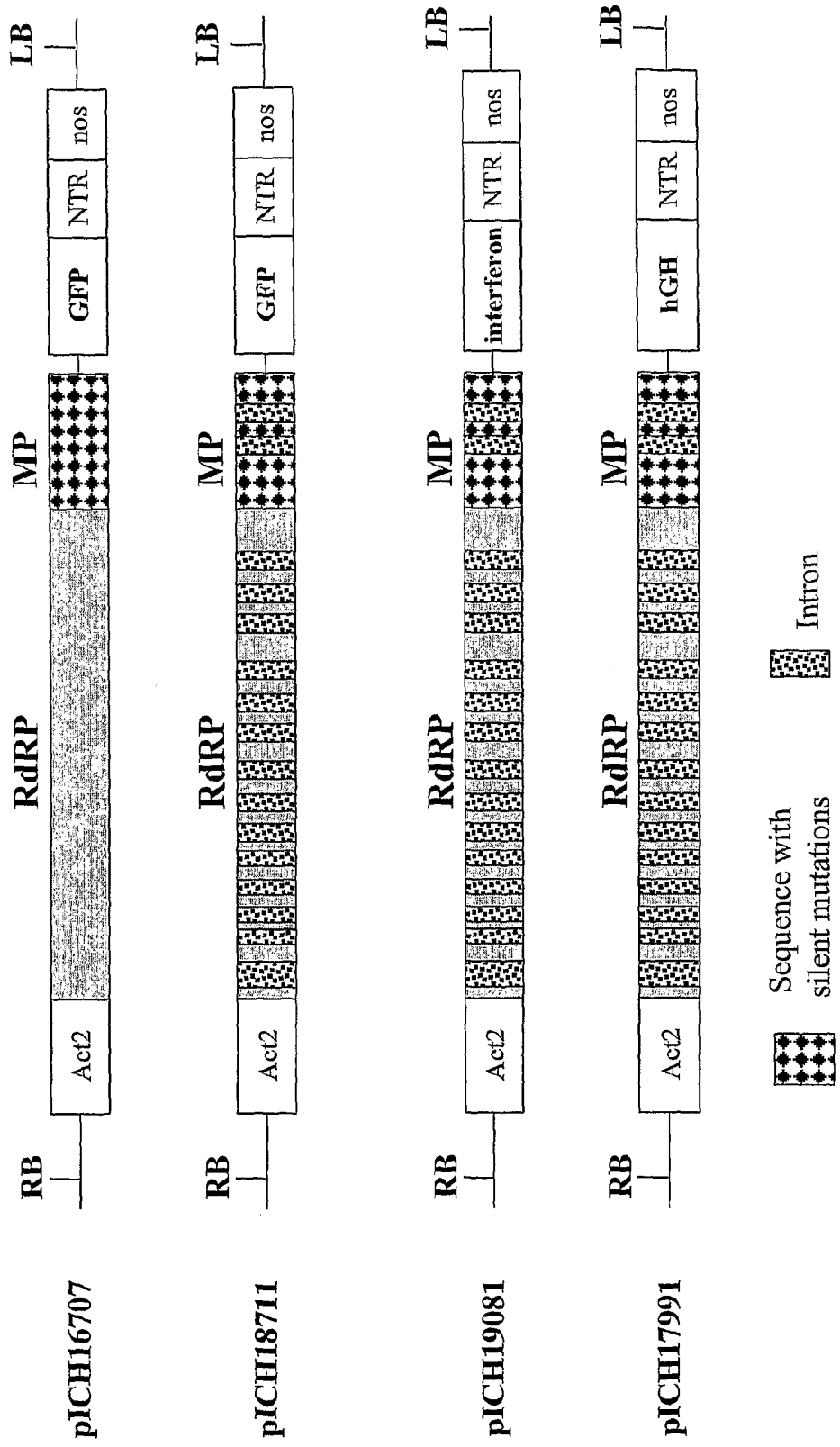

Expression of Pharmaceutical Proteins Using Vacuum Infiltration of Viral Vectors Delivered by Agrobacterium Two proteins of pharmaceutical interest were cloned instead of GFP in the improved vector described above. Cloning of the first protein, the human growth hormone (hGH) (sequence Genbank accession NM_000515), resulted in vector pICH17991 (FIG. 2C). Cloning of the second protein, the human interferon alpha (sequence Genbank accession V00548), resulted in vector pICH19081 (FIG. 2C). In this construct, the first 17 amino acids (LLVALLV-LSCKSSCSVG) of interferon were replaced by the Arabidopsis calreticulin apoplast targeting sequence (matqrranpss-lhlitvfsllvavvsaev). Constructs were inserted into agrobacterium strain GV3101 and used for whole plant infiltration. For both proteins, a high level of protein expression was obtained. For pICH17991, a high level of expression of hGH of 1 mg/g of infiltrated leaf tissue was obtained even though toxicity of the protein led to cell death in the infiltrated areas.

Example 4

Whole Plant Infiltration with a Vector Lacking MP

A frameshift was made at an Avrll site at the beginning of the MP in pICH17811 (FIG. 2C), resulting in construct pICH18722 (FIG. 5). This frameshift completely eliminates MP fucntion, and infiltration of this construct leads to replication and expression in individual cells only. However, because of the presence of introns, a large number of cells still expresses GFP.

The TVCV MP coding sequence was amplified by PCR from cloned TVCV cDNA (GenBank accession Z29370, bp 4802 to 5628) and subcloned in a binary vector under control of the 35S promoter, resulting in plasmid pICH10745. Coinfiltration of pICH18722 together with pICH10745 completely restores cell-to-cell movement, at least while MP is transiently expressed. pICH10745 was stably transformed in Nicotiana benthamiana. Infiltration of entire transformants expressing MP with pICH18722 led to GFP expression similar as infiltration of whole WT plants with pICH18711, while the infiltration of the wilt type plant does not lead to cell-to-cell movement of viral vector (see FIG. 16).

Example 5

Complementation of Mutant Agrobacteria to Provide for Transient Expression of Gene of Interest a) Complementation in Trans by a Transgenic Plant Host Expressing VirE2

The VirE2 gene was PCR-amplified from a DNA prep of A. tumefaciens C58 T-DNA (Gene Bank Accession No. AE009437, b.p 6368 to 8038) and cloned into vector pICH10745 replacing TVCV MP gene. The resulting construct pICHVirE2 (FIG. 15) were immobilized into A. tumefaciens (GV3101) and A. tumefaciens that lacks a functional VirE2 gene used for Agrobacterium-mediated leaf discs transfection of N. benthamiana plants (Horsh et al., 1985, Science, 227, 1229-1231) using 50 mg/L of kanamycin (Km) as selective agent. The construct pICH18722 with a frame shift within MP (FIG. 5) was transformed into an A. tumefaciens strain deficient in VirE2 function said deficiency caused by deletion in said gene and used in agro-infiltration experiments with wild type plants and plants transformed with pICH10745 plants.

The comparison of the efficiency of transient expression using competent and wild type host was performed by counting the number of cells expressing GFP per the same area of leaf surface or (more precisely) by determining and comparing the proportion of protoplasts expressing GFP in competent and wild type host, like it is shown in FIG. 10C for comparing frequencies of initiation of viral replication with control and modified viral vectors. Such comparative frequency of T-DNA delivery providing for transient expression can be used as measurement of the biosafety level of the system in comparison with system having no built in biosafety features.

Many other agrobacterial strains deficient in Vir E2 function can be used in this experiment, e.g. a strain carrying an insertional mutant of VirE2 (Christie et al, 1988, J. Bacteriol., 170, 2659-2667) or a strain carrying plasmid pSA with the osa gene that suppresses virE2 function (Lee, L-Y et al., 1999, J Bacteriol., 181, 186-196). Additionally, availability of agrobacterial genome sequence information including Ti plasmids (e.g. GeneBank Acc. No. NC003065; NC001277) and chromosomal DNA (e. g. GeneBank Acc. No. NC003063; NC003063) allows to generate any kind of mutants by replacing functional gene with its mutant form via homologous recombination.

An effect of VirE2 gene on T-DNA transfer efficiency into plant cells was tested by comparing different dilutions of overnight cultures of VirE2-containing and VirE2 deficient agrobacterial strains. Both agrobacterial strains contained pICH18711 viral vector (FIG. 2C) within T-DNA region of binary vector. The results of such comparison are shown in FIG. 17. It is evident from the picture that an efficiency of T-DNA transfer by VirE2 deficient agrobacterial strain is reduced at least by 10,0000 folds in comparison with agrobacteria containing functional VirE2 gene. A comparison of efficiency of transient expression in the leaves of competent (transformed with pICHVIRE2) and wild type N. benthamiana plants was performed and showed very efficient trans-complementation of VirE2 gene function from transgenic plant transformed with pICHVirE2 (FIG. 18). It was established by experimenting with different dilution series (not shown) that the efficiency of trans-complementation of VirE2 gene function from transgenic host is comparable with the use of agrobacterial strain carrying functional VirE2 gene.

b) Complementation in Trans by Mixing with a Wild Type Agrobacterial Strain Expressing VirE2

The experiment described in the previous example was repeated except that the complementation of virE2 function was achieved by mixing a strain deficient for virE2 function carrying pICH18722 with the *A. tumefaciens* strain C58 complementing virE2 function in trans. Freshly inoculated cultures of both agrobacterial strains were grown overnight to a density OD600 2.5-3.0 and mixed in equal proportions for infiltration of plant tissue. The final mixture for infiltration was diluted 50-, 100-, 1000- and 10000-fold. Infiltration of plant tissue was performed on *N. benthamiana* and *N. tabacum* leaves. Similar experiments were also performed but with ΔVirE2 strain carrying pICH18711 binary (having functional MP). The results of this experiment are shown in FIG. 19. It is evident that co-infiltration of mutant strain carrying pICH18711 binary (T-DNA+, ΔVirE2) with wild type strain (T-DNA-, VirE2) is no less efficient in delivery of T-DNA, than direct delivery of T-DNA by wild type strain (T-DNA+, VirE2).

Example 6

Figure 6A:
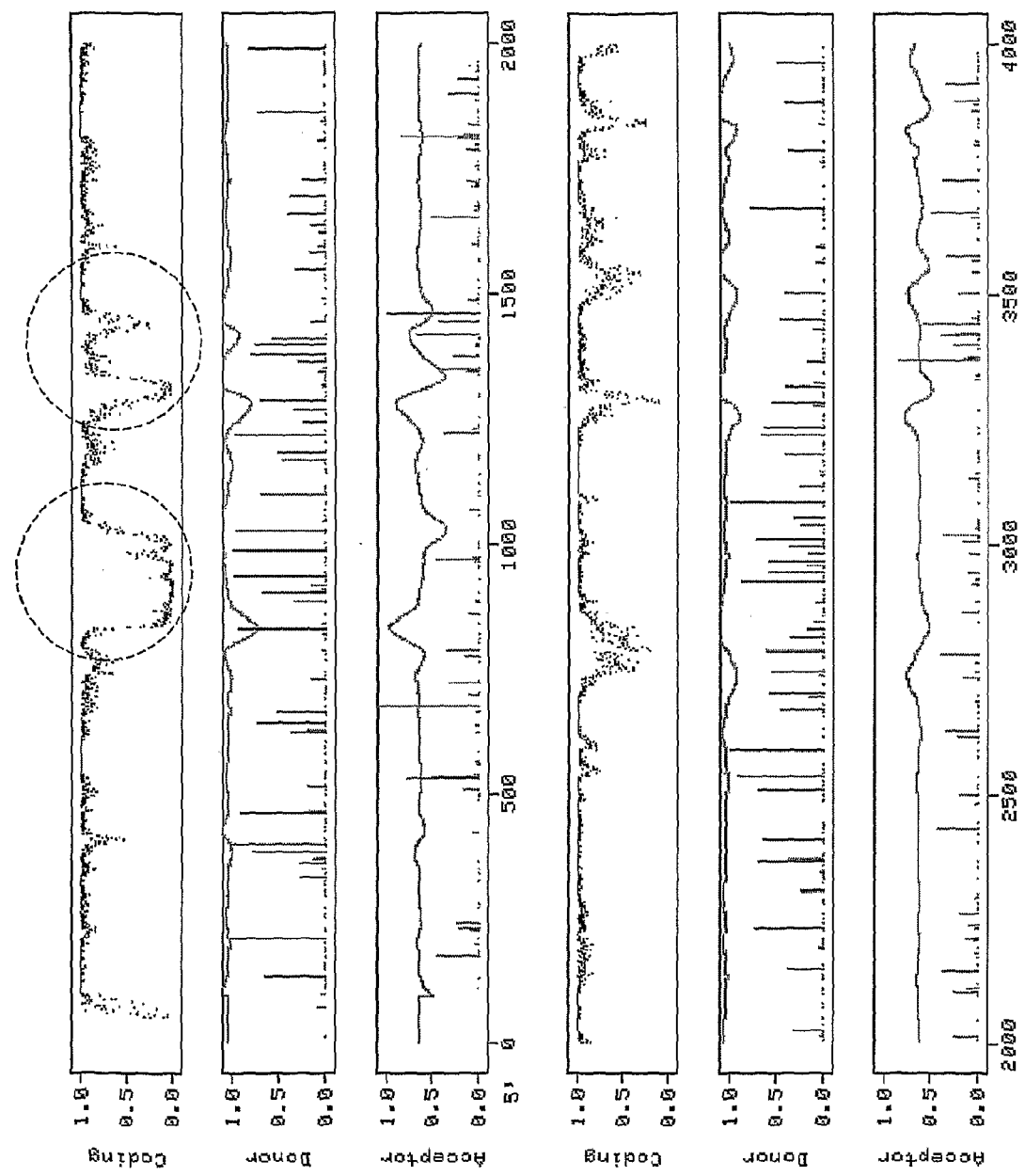
FIG. 6 shows the intron prediction profile of transcribed region of vector pICH8543. Nucleotide numbers are given on the horizontal axis. The vertical axis shows the probability for corresponding sequence/sequence region to be a coding sequence (coding), to serve as donor site (Donor) or as acceptor site (Acceptor). Circled parts correspond to selected localities where said function conservative differences should be introduced.
Figure 6B:
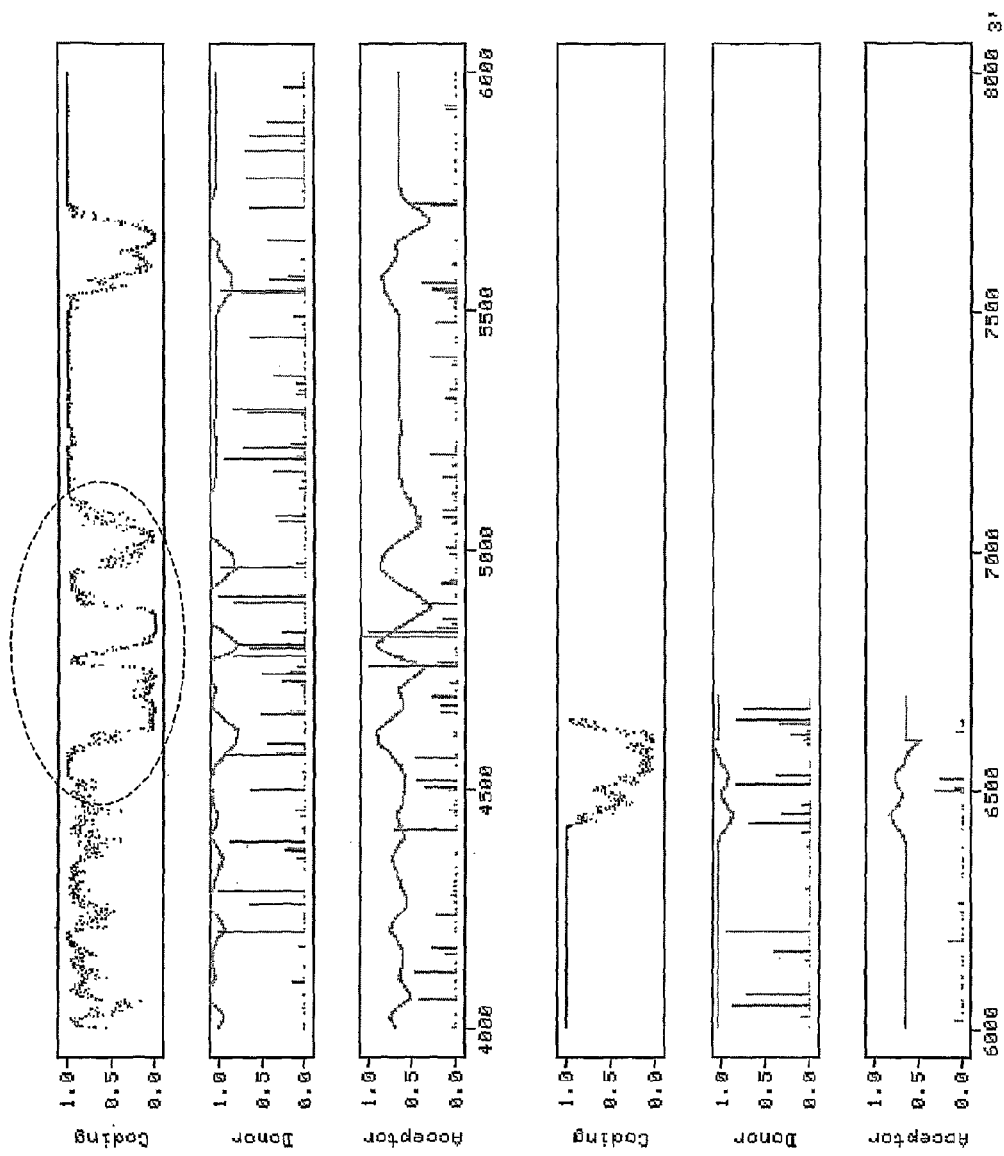
Figure 7:
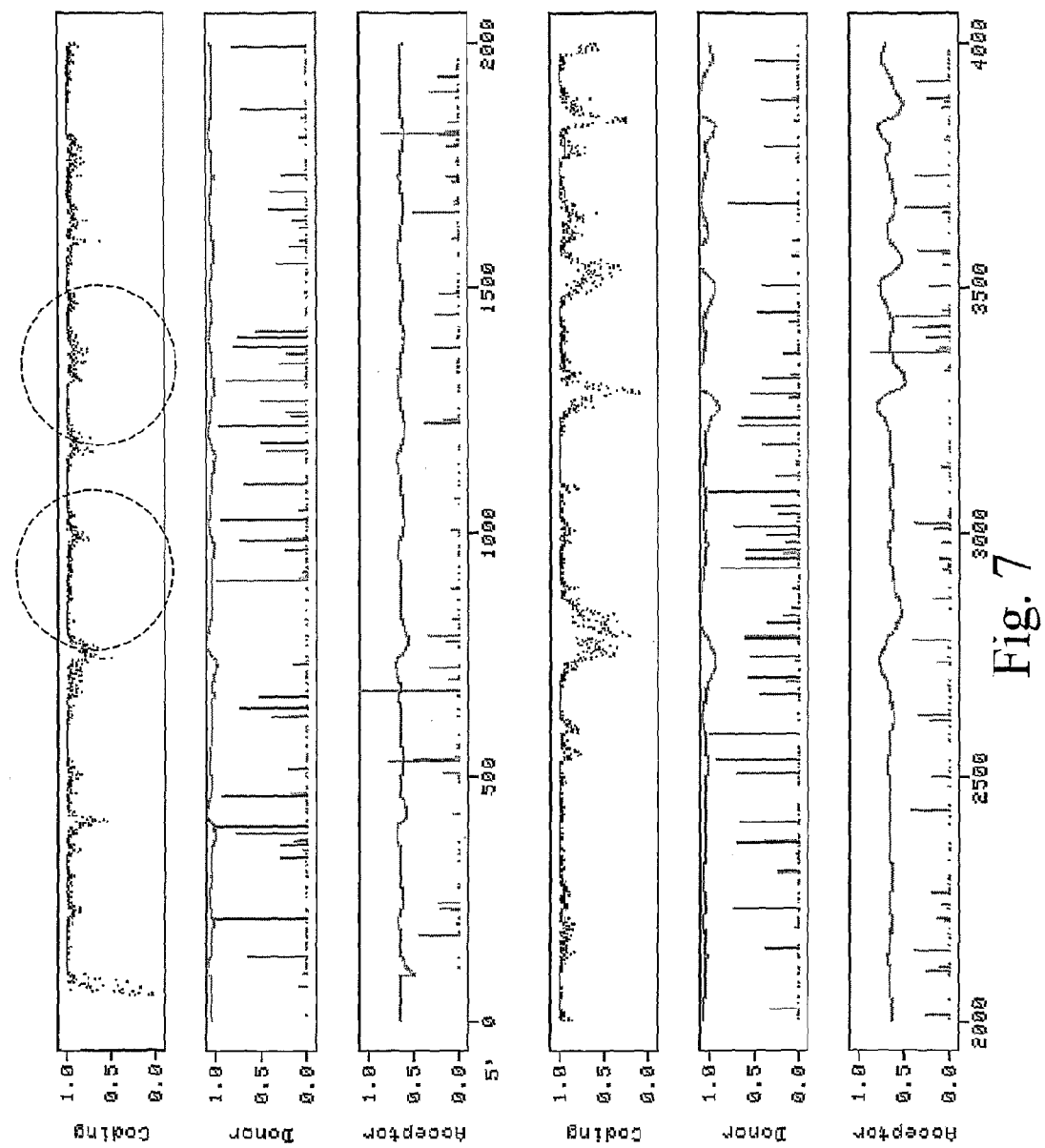
FIG. 7 shows the intron prediction profile of transcribed region of vector pICH15466

Removal of Intron-Like Sequences Increases the Frequency of Viral RNA Replicon Formation in the Cytoplasm We analyzed the sequence of the RNA replicon from pICH4351 using the Netgenell server program and noticed several intron-like sequence features that might induce alternative splicing events. One such feature is a 0.6 kb uridine-rich region (corresponding to nt 827 to 1462 in GenBank accession BRU03387) at the beginning of the RdRP (FIG. 6A). This region was replaced in pICH14833 by a PCR-mutagenized sequence that differs from the original sequence by a 54 nucleotide substitution (sequence given in annex as SEQ ID No. 2, FIG. 7). The 52 nucleotide substitution was made to replace T-rich sequences by more GC-rich sequences. All nucleotide substitutions were made silent so as not to change the RdRP protein sequence. This mutagenized fragment also contains two nucleotide substitutions (at position 829 and 1459; coordinates relative to GenBank accession BRU03387) that were introduced to remove putative cryptic splice donor and acceptor sites, respectively. To test the effect of these mutations, the resulting clone pICH15466 (FIG. 2A) was agroinfiltrated in *N. benthamiana* leaves with or without pICH10745 (movement protein in trans). Eight days after infiltration, a 10-fold increase in the number of GFP expressing cells was observed in the area infiltrated with pICH15466 (compared to pICH14833, FIG. 10). This suggests that removal of intron-like sequences from the viral replicon prevents unwanted alternative splicing events and results in more efficient initiation of viral replication. Coinfiltration of pICH15466 and pICH10745 leads to cell-to-cell movement of the modified replicon at a similar speed as a non-modified replicon. This shows that the modification of the RNA sequence did not affect cell to cell movement of the viral vector.

Example 7

Removal of Intron-Like Sequences in the MP Subgenomic Promoter

A second potentially problematic region corresponds to the MP subgenomic promoter (FIG. 6B). This region is very T-rich and resembles intron sequences very closely. As a consequence, many cryptic splice donor and acceptor sites are predicted in nearby sequences by intron prediction programs. Unfortunately, modifications cannot be made easily to this region without affecting subgenomic promoter function. We decided to completely mutagenize the entire region without regard of the subgenomic promoter, and to provide MP in trans to compensate for the expected loss of MP expression. As MP will not be expressed from this construct, we also deleted most of MP sequence except for the 3' sequences that contain the CP subgenomic promoter which is required to drive expression of the gene of interest. We therefore replaced a 383 bp fragment in pICH14833 (bp 4584 to 5455 in GenBank accession BRU03387) by a 297 bp mutagenized fragment. The resulting construct pICH15900 (FIG. 2A) was agroinfiltrated in *Nicotiana benthamiana* leaves with or without pICH10745. Interestingly, a huge increase in the numberof cells initiating replication was detected in comparison to leaf areas infiltrated by pICH14833. By counting GFP-expressing protoplasts prepared from infiltrated leaf areas, we estimate that this modification results in a 80 to 100-fold increase in the number of cells initiating viral replication compared to the unmodified pICH14833. pICH15900 was coinfiltrated with pICH10745 (p35S-MP expression cassette) and an increase in GFP fluorescence was detected due to cell to cell movement. This increase was, however, very limited because so many cells already expressed GFP even in the absence of cell-to-cell movement. A 1000-fold dilution of the agrobacterium suspension containing pICH15900 coinfiltrated with an undiluted suspsension of agrobacteria containing pICH10745 gave rise to separate GFP expression foci. Fluorescent foci were as bright and of the same size as control foci obtained with pICH14833. This shows that the modification in pICH15900 and the delivery of MP in trans does not compromize the functionality of the replicon regarding the level of replication, expression of the sequence of interest and cell-to-ell movement. The same constructs (pICH14933 and pICH15900, with or without pICH10745) were coinfiltrated to *Nicotiana tabacum* leaves. The modifications in pICH15900 lead to a similar increase in the number of cells initiating replication (in comparison to pICH14833) as they did in *N. benthamiana.*

Example 8

Addition of Introns Improves the Frequency of Formation of Functional RNA Replicons in the Cytoplasm We then tested whether the addition of introns into said sequence portion encoding said replicon would increase the frequency of initiation of replication. Two constructs were made, pICH15025 and pICH15034 (FIG. 2A), each containing three different *Arabidopsis thaliana* introns in two different regions of the RdRP. pICH15025 was designed to contain introns in the middle of the RdRP, while pICH15034 contains introns in the 3' end of the RdRP, upstream of the MP subgenomic promoter. The introns were amplified by PCR from arabidopsis genomic DNA and incorporated into viral sequences using PCR with primers overlapping the planned intron/exon junctions. The fragments containing the introns were subcloned into pICH14833 as an AvaI HindIII fragment (SEQ ID No. 4 in the annex) to make pICH15025 or as a Pst1 NcoI fragment (SEQ ID No. 5 in the annexe) to make pICH15034.

Both constructs were agroinfiltrated into *N. benthamiana* leaves and compared to pICH14833. Both constructs significantly increased the number of cells initiating viral replication (FIG. 10A). This increase was estimated to be on the order of a 50-fold improvement relative to pICH14833. Both constructs were also coinfiltrated with a MP expressing clone, and cell-to-cell movement was found to be identical as for clones without introns. Both constructs were also tested in *N. tabacum*, and the same improvement was observed as in *N. benthamiana* (FIG. 10B).

A third clone was made, pICH15499, which contained all 6 introns (FIG. 9, 2B, 10A, 10B). This construct was tested in *N. benthamiana* and *N. tabacum*. This construct was more efficient than each individual construct with 3 introns, but the improvement was however less than additive.

Example 9

Addition of Introns and Removal of Intron-Like Sequences Increases the Frequency of the Formation of Functional RNA Replicons in the Cytoplasm Removing intron-like features and adding additional introns in one construct showed that both types of modifications can contribute to improve initiation of viral replication. We subcloned the 6 introns of pICH15499 into pICH15900 which contains the mutagenized MP subgenomic promoter region. The resulting clone pICH15860 (FIG. 2B) was infiltrated into *N. benthamiana* leaves and found to work significantly better than either parental clones within the range of approximately 50% to 90% of all protoplasts expressing GFP (FIG. 10). The best performing construct contains introns within the RdRP region and modified MP subgenomic promoter region (pICH16191, FIG. 10C). In comparison to a clone without any modification, this represents an 80- to 300-fold improvement. This construct was also coinfiltrated with a MP-expressing construct (pICH10745) and it was found that the modifications did not compromize cell-to-cell movement or replication.

Example 10

Not all Intron Additions Increase the Frequency of Appearance of Functional RNA Replicons in the Cytoplasm We inserted two different *Arabidopsis* introns at the beginning of the RdRP, resulting in clone pICH15477 (FIG. 2B) (the sequence of this region is shown as SEQ ID No. 7 in the annex). The sequence in this region already looks very "exon-like" (e.g. GC-rich without cryptic splice sites) before the addition of introns. No improvement on replication of viral initiation was seen with this construct. Therefore, not any addition of an intron results in an improvement of the viral vector. It appears that the position chosen for intron insertion or mutagenesis is an important parameter. For example, all intron insertions or nucleotide substitutions that were made in regions near problematic structures such as the MP subgenomic promoter, resulted in large improvements, while insertions of introns into sequences that are already "exon-like" did not improve initiation of viral replication in a significant way.

Example 11

Insertion of Introns in MP Sequences Increase the Frequency of Viral Replicon Formation We first made a frameshift in the MP by digestion with the restriction enzyme AvrII, filling and religation. We then inserted two introns in the MP. The resulting clone pICH16422 (FIG. 2B) was infiltrated in *Nicotiana benthamiana* leaves. An about 100-fold increase in the number of cells containing the functional viral replicon was detected.

Example 12

Insertion of Introns into a MP Containing Vector Improves the Frequency of Initiation of Viral Replication of Autonomous Functional Clones A Kpn1 EcoRI fragment was subcloned from pICH15499 into pICH8543. The resulting clone, 16700 (FIG. 2B) contained a complete viral vector with 6 introns in the RdRP. This clone was infiltrated in *N. benthamiana* leaf and efficiently initiated replication. This clone was also able to move cell to cell without the need to provide additional MP in trans.

Example 13

Activation of an Agro-Delivered Inactive Replicon in an Engineered Host Plant It is also possible to agro-infiltrate intron-containing viral vector precursors in transgenic plants. To prevent accidental infection of plants not destined for producing said protein of interest (e.g. plants in open environment), an inactive clone can be made that has a part of the vector present in antisense orientation (FIG. 11). Incorporation of recombination sites and of introns sequences at the extremities of the inverted fragment allow for this fragment to be 'flipped' in the correct orientation by using an appropriate recombinase. Recombination sites will be completely eliminated from the replicon by splicing. Introns in the pro-replicon allow efficient initiation of replication after recombination and transcription. In one specific example, the recombination sites are located within the gene of interest and downstream of the pro-replicon. Such a configuration prevents any gene expression before recombination. Other configurations can be considered where the recombination sites are located in other areas of the pro-replicon such as the RdRP and upstream of the promoter. Intron sequences at the recombination site have the advantage of allowing to completely remove the recombination site from the replicon, but also increases the efficiency of viral replication, as described before. Transgenic plant host providing for recombinase activity can be engineered and used for agroinfiltration with a vector containing an inactive viral vector precursor. Said viral vector precursor can be activated only in the cells of said engineered plant host.

Example 14

Plant Viral RNA Sequences Contain Potentially Unstable Regions

The analysis of RNA profile of selected plant RNA viruses as well as one well characterised plant gene (AtDMC1) was performed by using the Netgenell server program. The RNA profile shown in FIG. 12 for AtDMC1 clearly reflects the presence of 14 introns (circled), previously identified by comparing the cDNA and genomic DNA sequences. It is evident that RNA profiles of two plant viruses have regions (see the FIGS. 13, 14) which might cause problems for the stability of said RNA, if they are placed in plant nuclear environment. We have analysed the RNA profiles of several other representatives of plant RNA viruses (not shown), such as Brome mosaic Virus, different strains of TMV, and many others. All of them have potential problematic regions that might compromise the efficiency of plant RNA virus-based replicon formation if delivered into the plant cell as DNA precursors.

Example 15

Whole Plant Infiltration with Geminiviral Vectors

The expression vectors pICH4300, pICH5202/3 and pICH5170 (FIG. 15) based on bean golden mosaic virus (BGMV) isolate DSMZ PV-0094 were made as described in examples 10 and 11 of WO02077246. Construct pICH5170 was used for stable transformation of N. benthamiana and N. tabacum plants, as described in EXAMPLE 5. Constructs pICH5202/3 and pICH5170 were immobilized into A. tumefaciens deficient for the VirE2 function and A. tumefaciens C58 strains. Strains with an immobilized viral replicon (pICH5202/3) were used for agroinfiltration of whole Nicotiana plants transformed with pICH5170. Transgenic plant host provided for replication of a DNA replicon carrying GFP with geminiviral origin of replication located within the so-called common region (CR). For agrobacterium strain deficient in VirE2 function, agroinfiltration was performed together with the non-transformed A. tumefaciens C58. Alternatively, N. benthamiana plants transformed with pICH-VirE2 were crossed with plants transformed with pICH5170. The F1 progeny containing T-DNA regions from both constructs was selected by PCR and used for agroinfiltration with agrobacterium function and carrying pICH5202/3.

Strains with immobilized viral replicon (pICH5170) were used for agroinfiltration of whole Nicotiana plants.

The results of the experiments described above showed that no GFP expression took place in infiltrated plants when the strain deficient for VirE2 function was used without complementation of said function with the help of either a transgenic host plant or agrobacteria expressing VirE2. However, the expression level in experiments where complementation of the VirE2 function was required in trans did not show a significant difference from that when vectors were immobilized in A. tumefaciens C58.

Example 16

Generation of Mutants Deficient in Conjugational Transfer of Bacterial Plasmids The tra and trb genes were described as being involved in conjugational transfer of the Ti plasmid (Farrand et al., 1996, J. Bacteriol., 178, 4233-4247; Li et al., 1999, J Bacteriol., 181, 5033-41). In order to delete these genes from the Ti plasmid of Agrobacterium tumefaciens strain C58, vectors containing flanking DNA regions were used for transformation, whereby the deletion was introduced by two sequential recombination events. Deletion vectors were based on vector pDNR-1r (Clontech) containing carbenicillin resistance as a positive selection marker and the sacB gene which causes sucrose intolerance, as a negative selection marker.

For the deletion of tra genes (traG, traD, traC, oriT, traA, traF, traB, traH, traM), flanking regions of around 700 bp were PCR-amplified from Agrobacterium C58 DNA with primers oSM570 (5'-gaggatccaacgtttaggagaaccag-3') plus oSM571 (5'-ttggtctcacggtatacgcacactgaacatgcg-3') and oSM572 (5'-ttggtctcaaccggtttccgtttgtctc-3') plus oSM573 (5'-acgtctagagatcgcgttccagaccaac-3'). Joining of the PCR fragments after restriction with BsaI created a Bst11071 restriction site without introducing additional nucleotides; at the outer ends, a BamHI site and an XbaI site were introduced by the primers. The two PCR fragments were joined in vector pDNR-1r restricted with BamHI and XbaI. The resulting plasmid pICF12721 was used for Agrobacterium transformation using electroporation, and selection was made first on carbenicillin, and hereafter without antibiotic, but in the presence of 5% sucrose in order to counterselect for cells with the double recombination event, which do not contain the vector backbone.

For the deletion of trb genes (trbB, trbC, trbD, trbE, trbJ), flanking regions of around 700 bp were PCR-amplified from Agrobacterium C58 DNA with primers oSM566 (5'-ctgaattcaggcaaacgcaccgtgagatg-3') plus oSM567 (5'-tcaccatgggtcacgcggcactcctg-3') and oSM568 (5'-tcaccatggcccaggcccggcgtgaac-3') plus oSM569 (5'-acatctagatgccggcatcgaagatgttg-3'). Joining of the PCR fragments created an NcoI restriction site without introducing additional nucleotides; at the outer ends, an EcoRI site and an XbaI site were introduced by the primers. The two PCR fragments were joined in vector pDNR-1r restricted with EcoRII and XbaI. The resulting plasmid pICF12711 was used for Agrobacterium transformation as described above.

In order to measure conjugational transfer between agrobacteria, a selectable Ti plasmid showing constitutive transfer was constructed by replacing the accR gene which codes for an opine-binding repressor by a kanamycin resistance cassette. This was made by transformation of Agrobacterium tumefaciens strain C58 with vector pICF12741 which is also based on vector pDNR-1r and contains two flanking regions PCR-amplified from Agrobacterium C58 DNA with primers oSM554 (5'-gagctagctccgtccttcacctgggc-3') plus oSM555 (5'-ttggtctcaccggccgatagccaaaaactgc-3') and oSM556 (5'-ttggtctcgccggccaaactccggtttgc-3') plus oSM557 (5'-atgggccct-tcgaacgcaattcctgttgc-3') and a kanamycin resistance (PCR amplified with primers oSM584 (5'-cctcggccgcgaacggcct-cac-3') and oSM585 (5'-ctacggccgctgacagctaaaacaattcatcc-3') from binary vector pICH18711) in the XmaIII site between them. The strain with the kanamycin-resistant Ti plasmid was incubated together with acceptor strain GV3101 carrying a chromosomal rifampicin resistance but no Ti plasmid on a nitrocellulose membrane for 2 hours at 28° C., similarly as described in Piper & Farrand (1999, Appl Environ Microbiol., 65, 2798-2801). Transconjugants were selected on plates with rifampicin and kanamycin. For the Ti plasmid carrying the acc deletion but intact tra and trb genes, a conjugation efficiency of around $3-4\times10^{-4}$ transconjugants per input donor was found. For tra and trb mutants the conjugation efficiency was below the detection limit ($<10^{-7}$).

The influence of the mutations on DNA transfer to plants was tested by infiltration of N. benthamiana plants with bacteria containing viral vector pICH18711 encoding GFP.

Bacteria were used in various dilutions so that single fluorescing spots could be observed on the leaves. The efficiency of DNA transfer to plants was comparable to bacteria without acc, tra, or trb deletions.

Example 17

Generation of Auxotrophic Mutants

The genes leuB encoding for 3-isopropylmalate dehydrogenase involved in leucine biosynthesis and pyrE encoding for orotate-phoshoribosyl transferase involved in uridine biosynthesis were selected for generation of auxotrophic agrobacterial strains.

The coding sequence for leuB can not be deleted completely as it overlaps with the 3' of hypothetical protein ATU2792 located at the reverse strand of agrobacterial chromosome. Therefore, bp 2792384-2793470 of chromosome 1 were selected for deletion by connecting 775 bp of the upstream sequence with 834 bp of the downstream sequence via BspHI restriction site occuring naturally at the 5'-end of leuB coding sequence. The vector pDNR-1r (Clontech) was used for generating deletions within agrabacterial target genes.

Similarly to leuB, no catabolic complementation of pyrE gene is possible. An uracil-phoshoribosyl transferase gene is present in Agrobacteria, so uridine supplementation can be replaced by the cheaper uracil. Moreover, the pyrE deletion can be used as positive selection marker. The selection takes advantage of the fact that wild type agrobacteria are sensitive to the toxic uracil analogue-5-fluoroorotic acid, whereas the pyrE mutant shall be resistant.

The start codon of pyrE is annotated differently (bp 394734-395534, Acc. No NP_531105 versus bp 394836-395534, Acc. No. Q8UI98) in different databases. However, homology to other pyrE sequences does not start before bp 394836. Nevertheless, two deletion variants (deletions starting at the positions 394760 or 394849 and both ending at the position 395531 of chromosome 1) were designed. The fragments containing deletions were cloned into the EcoRI-BamHI site of the vector pDNR-1r yielding vectors pICF1263 (ΔleuB bp 2792384-2793470), pICF1264 (ΔpyrE bp 394760-395531) and pICF1265 (ΔpyrE bp 394848-395531) (see FIG. 21).

Agrobacterium strain GV3101 was transformed with the plasmids pICF1263-3 (ΔleuB bp 2792384-2793470), pICF1264-1 (ΔpyrE bp 394760-395531) and pICF1265-10 (ΔpyrE bp 394848-395531). A small number of transformants (6-10 cfu/μg) were obtained after two days of selection on carbenicillin-containing media. The cointegrates were resolved by growing selected clones consecutively in liquid LB+rifampicin and LB+rifampicin+saccharose. The agrobacteial mutants containing the desired deletions in target genes were confirmed by PCR analysis of agrobacterium DNA isolated from the LB+rifampicin+saccharose cultures.

The mutant strains 1263-3-3 and 1263-3-10 and the wild type parent strain GV3101 were grown in LB-rich-medium and M9-minimal-medium without and with supplementation of 30 mg/l and 150 mg/l leucine. There was no difference in growth in LB-medium between mutant and wild type strains, whereas in M9-media only the wild type strain could grow. When the M9 medium was supplemented with leucine, both the wild type and the mutant strain could grow. The growth of different mutant strains on media with and without complementation is shown in FIGS. 22 and 23. The growth rate increased with higher leucine concentration. Agrobacterium mutant 1263-3-3 was transformed with the GFP plasmids pICH18711 to analyse the infection efficiency in N. benthamiana.

ANNEX

SEQ ID No. 1 (NcoI-EcoRI fragment of pICH14833):
ccatggacaaagtgataaaggcagcttttttgtggagacgatagcctga tttacattcctaaaggtttagacttgcctgatattcaggcgggcgcga acctcatgtggaacttcgaggccaaactcttcaggaagaagtatggtt acttctgtggtcgttatgttattcaccatgatagaggagccattgtgt attacgatccgcttaaactaatatctaagttaggttgtaaacatatta gagatgttgttcacttagaagagttacgcgagtctttgtgtgatgtag ctagtaacttaaataattgtgcgtattttcacagttagatgaggccg ttgccgaggttcataagaccgcggtaggcggttcgtttgcttttttgta gtataattaagtatttgtcagataagagattgtttagagatttgttct ttgtttgataatgtcgatagtctcgtacgaacctaaggtgagtgattt cctcaatctttcgaagaaggaagagatcttgccgaaggctctaacgag gttagaattc SEQ ID No. 2 (part of pICH15466):
ggagataacctgagcttcttcttccataatgagagcactctcaattac acccacagcttcagcaacatcatcaagtacgtgtgcaagacgttcttc cctgctagtcaacgcttcgtgtaccacaaggagttcctggtcactaga gtcaacacttggtactgcaagttcacgagagtggatacgttcactctg ttccgtggtgtgtaccacaacaatgtggattgcgaagagttttacaag gctatggacgatgcgtggcactacaaaaagacgttagcaatgcttaat gccgagaggaccatcttcaaggataacgctgcgttaaacttttggttc ccgaaagtgagagacatggttatcgtccctctctttgacgcttctatc acaactggtaggatgtctaggagagaggttatggtgaacaaggacttc gtctacacggtcctaaatcacatcaagacctatcaagctaaggcactg acgtacgcaaacgtgctgagcttcgtggagtctattaggtctagagtc ataattaacggtgtcactgccaggtctgaatgggacacagacaaggca attctaggtccattagcaatgacattcttcctgatcacgaagctgggt catgtgcaagat SEQ ID No. 3 (part of pICH15900):
gcggacgatacgtgatccaccatgatagaggagccattgtgtattacg atccgcttaaactaatatctaagctcggctgcaagcacatcagagacg tcgtgcacttagaagagttacgcgagtctttgtgcgacgtagctagta acttgaacaactgcgcctacttctcacagttagatgaggccgttgctg aggtccacaagactgcggtcggaggctccttcgcgttctgtagcatca tcaaatacttgtcagacaagaggctgttcagggacctgttcttcgtct gagttgacg SEQ ID No. 4 (part of pICH15025):
cccgagctatactgtaccttcgccgaccgattggtactacagtacaag aaggcggaggagttccaatcgtgtgatctttccaaacctctagaagag

ANNEX tcagagaagtactacaacgcattatccgagctatcagtgcttgagaat
ctcgactcttttgacttagaggcgtttaagactttatgtcagcagaag
aatgtggacccggatatggcagcaaaggtaaatcctggtccacacttt
tacgataaaaacacaagattttaaactatgaactgatcaataatcatt
cctaaaagaccacacttttgttttgttctaaagtaattttttactgtt
ataacaggtggtcgtagcaatcatgaagtcagaattgacgttgccttt
caagaaacctacagaagaggaaatctcggagtcgctaaaaccaggaga
ggggtcgtgtgcagagcataaggaagtgttgagcttacaaaatgatgc
tccgttcccgtgtgtgaaaaatctagttgaaggttccgtgccggcgta
tggaatgtgtcctaagggtggtggtttcgacaaattggatgtggacat
tgctgatttccatctcaagagtgtagatgcagttaaaaagggaactat
gatgtctgcggtgtacacagggtctatcaaagttcaacaaatgaagaa
ctacatagattacttaagtgcgtcgctggcagctacagtctcaaacct
ctgcaaggtaagaggtcaaaaggtttccgcaatgatccctcttttttt
gtttctctagtttcaagaatttgggtatatgactaacttctgagtgtt
ccttgatgcatatttgtgatgagacaaatgtttgttctatgttttagg
tgcttagagatgttcacggcgttgacccagagtcacaggagaaatctg
gagtgtgggatgttaggagaggacgttggttacttaaacctaatgcga
aaagtcacgcgtggggtgtggcagaagacgccaaccacaagttggtta
ttgtgttactcaactgggatgacggaaagccggtttgtgatgagacat
ggttcagggtggcggtgtcaagcgattccttgatatattcggatatgg
gaaaacttaagacgctcacgtcttgcagtccaaatggtgagccaccgg
agcctaacgccaaagtaattttggtcgatggtgttcccggttgtggaa
aaacgaaggagattatcgaaaaggtaagttctgcatttggttatgctc
cttgcatttttaggtgttcgtcgctcttccatttccatgaatagctaag
attttttttctctgcattcattcttcttgcctcagttctaactgtttg
tggtattttgtttttaattattgctacaggtaaacttctctgaagact
tgattttagtccctgggaaggaagctt SEQ ID No. 5 (part of pICH15034):
ctgcaggtaaaatattggatgccagacgtatattcttctttttgatttg
taacttttttcctgtcaaggtcgataaaatttatttttttttggtaaaag
gtcgataattttttttttggagccattatgtaattttcctaattaactg
aaccaaaattatacaaaccaggtttgctggaaaatttggttgcaatga
tcaaaagaaacatgaatgcgccggatttgacagggacaattgacattg
aggatactgcatctctggtggttgaaaagttttgggattcgtatgttg
acaaggaatttagtggaacgaacgaaatgaccatgacaagggagagct
tctccaggtaaggacttctcatgaatatagtggcagattagtgttgt
taaagtcttggttagataatcgatgcctcctaattgtccatgttttta
ctggttttctacaattaaaggtggctttcgaaacaagagtcatctaca SEQ ID No. 6 (fragment of pICH15477):
gttggtcagttagcggactttaactttgtggatttgccggcagtagat
gagtacaagcatatgatcaagagtcaaccaaagcaaaagttagacttg
agtattcaagacgaatatcctgcattgcagacgatagtctaccattcg
aaaaagatcaatgcgattttcggtccaatgttttcagaacttacgagg
atgttactcgaaaggattgactcttcgaagtttctgttctacaccaga
aagacacctgcacaaatagaggacttcttttctgacctagactcaacc
caggcgatggaaattctggaactcgacatttcgaagtacgataagtca
caaaacgagttccattgtgctgtagagtacaagatctgggaaaagtta
ggaattgatgagtggctagctgaggtctggaaacaaggtgagttccta
agttccatttttttgtaatccttcaatgttattttaacttttcagatc
aacatcaaaattaggttcaattttcatcaaccaaataatatttttcat
gtatatataggtcacagaaaaacgaccttgaaagattatacggccgga
atcaaaacatgtctttggtatcaaaggaaaagtggtgatgtgacaacc
tttattggtaataccatcatcattgccgcatgtttgagctcaatgatc
cccatgg gttttagttttattgcaacaacaacaacaaattacaataacaacaaac
aaaatacaaacaacaacaacatggcacaatttcaacaaacaattgaca
tgcaaactctccaagccgctgcgggacgcaacagcttggtgaatgatt
tggcatctcgtcgcgtttacgataatgcagtcgaggagctgaatgctc
gttccagacgtcccaaggtaaaacaacatttcattcacatatatgaat
acttttgtcattgagtacgaagaagacacttactacttgttgatgaaa
gtttccgcctttatacttatctatatcattttcatcatttcaaactag
tatgaaattaggtgatgtttatatgatatcatggaacattaatctata
gggaaactgttttgagttagttttgtataatatttttccctgtttgat
gttaggttcatttctccaaggcagtgtctacggaacagacactgattg
caacaaacgcatatccggagttcgagatttcctttactcatacgcaat
ccgctgtgcactccttggccggaggccttcggtcacttgagttggagt
atctcatgatgcaagttccgttcggctctctgacctacgacatcggcg
gaaacttctccgcgcacctcttcaaaggtaattttctttctctactca
attttctccaagatccaatatttgaagactgatctatagttaaaatta
atctctactccattcttgttacctcaggtcgcgattacgttcactgct
gcatgc

The invention claimed is:

1. A process of producing a protein of interest by expressing a sequence of interest in a plant or in plant leaves, comprising:
(a) transfecting said plant or said plant leaves with an Agrobacterium strain in the presence or in the absence of a complementing factor, said Agrobacterium strain containing in T-DNA a heterologous DNA sequence having a sequence portion encoding a replicon,
wherein said sequence encoding a replicon contains
(i) sequences necessary for replicon function of said replicon, said sequences being derived from a plant virus, and
(ii) said sequence of interest to be expressed,
(b) optionally isolating said protein of interest from said plant or said plant leaves infiltrated in step (a),
wherein said Agrobacterium strain is provided with a first genetic modification rendering said Agrobacterium strain defective for transfecting organisms with said T-DNA in the absence of said complementing factor, and
wherein said plant or said plant leaves are infiltrated in step (a) with a suspension of said Agrobacterium strain, said suspension having a concentration of cells of said Agrobacterium strain corresponding to a calculated optical density at 600 nm of at most 0.04.

2. The process according to claim 1, wherein said first genetic modification renders said Agrobacterium strain defective in a function required for introducing said T-DNA in cells of said plant or plant leaves.

3. The process according to claim 1, wherein said complementing factor provides a function required for transfecting cells of said plant or said plant leaves by said Agrobacterium strain with said T-DNA.

4. The process according to claim 3, wherein said function required for transfecting cells of said plant or said plant leaves with said T-DNA is provided by a gene or protein selected from the group consisting of VirE2, GALLS, and VirF.

5. The process according to claim 1, wherein, as said first genetic modification, a function of said Agrobacterium strain required for transfecting said organisms is placed under the control of a heterologous chemically regulated promoter; and
said complementing factor is a small molecular compound capable of regulating said chemically regulated promoter.

6. The process according to claim 1, wherein said complementing factor is provided to said plant or said plant leaves by a second Agrobacterium strain.

7. The process according to claim 1, wherein said plant is provided with a second genetic modification, said second genetic modification being or encoding said complementing factor.

8. The process according to claim 2, whereby said Agrobacterium strain is auxotrophic and is provided to said plant or to said plant leaves in the presence of an essential metabolite required for auxotrophic growth of said Agrobacterium strain.

9. The process according to claim 1, whereby said first genetic modification renders said Agrobacterium strain auxotrophic, and said complementing factor is an essential metabolite for said Agrobacterium strain required for auxotrophic growth of said Agrobacterium strain.

10. The process according to claim 2, whereby said Agrobacterium strain is conditionally lethal and is grown and/or provided to said plant or to said plant leaves in the presence of a metabolite required for survival of said Agrobacterium strain.

11. The process according to claim 1, whereby said first genetic modification renders said Agrobacterium strain conditionally lethal, and said complementing factor is an essential metabolite for said Agrobacterium strain required for survival of said Agrobacterium strain.

12. The process according to claim 1, whereby said Agrobacterium strain has a further genetic modification that renders said Agrobacterium strain defective for conjugative plasmid transfer from said or to said Agrobacterium.

13. The process according to claim 12, wherein said defectiveness for conjugative transfer is caused by a lack function of at least one of the following genes: oriT, traG, and traF.

14. The process according to claim 1, whereby said sequence portion encoding a replicon encodes a replicon that is defective in a function required for spreading of said replicon in said plant or in said plant leaves.

15. The process according to claim 14, wherein said sequence portion encodes a replicon that is defective in a function required for long-distance or cell-to-cell movement of said replicon.

16. The process according to claim 14, wherein said function required for spreading of said replicon is provided to said plant or said plant leaves by expressing said function in said plant or said plant leaves from a nucleic acid sequence other than said heterologous DNA sequence.

17. The process according to claim 1, wherein said *Agrobacterium* strain expresses the oncogenic suppressive activity protein Osa.

18. The process according to claim 1, whereby said *Agrobacterium* strain has a genetically modified quorum sensing or virulence induction regulatory systems for reducing T-DNA transfer to non-target organisms.

19. The process according to claim 1, wherein said complementing factor is provided in said plant or said plant leaves by trans-splicing of two RNA sequences, whereby at most one of said two RNA sequences is encoded by said *Agrobacterium* strain.

20. The process according to claim 1, wherein said replicon is a DNA replicon.

21. The process according to claim 1, wherein said replicon is an RNA replicon and said sequence portion encoding said RNA replicon is operably linked to a transcriptional promoter.

22. The process according to claim 21, wherein said sequences necessary for replicon function exhibit at selected localities function-conservative differences from said plant RNA virus, said differences causing an increased frequency of replicon formation compared to an RNA replicon not exhibiting said differences.

23. The process according to claim 22, wherein said function-conservative differences comprise removal of cryptic splicing sites flanking A/U-rich regions.

24. The process according to claim 22, wherein said function-conservative differences comprise the insertion of one or more nuclear introns or one or more sequences capable of forming nuclear introns near or within A/U-rich localities of said sequences necessary for replicon function.

25. The process according to claim 1, wherein said replicon is deficient for cell to cell movement in said plant or in said plant leaves.

26. The process according to claim 21, wherein said plant virus is a tobamovirus, preferably a tobacco mosaic virus.

27. The process according to claim 1, wherein said *Agrobacterium* strain is *A. tumefaciens* or *A. rhizogenes* or other microorganism engineered to contain *Agrobacterium*-derived functional T-DNA transfer genetic machinery.

28. The process according to claim 1, wherein said genetic modification is done on a bacterial chromosome and/or on a plasmid chromosome.

29. The process according to claim 1, wherein said plant or said plant leaves are infiltrated in step (a) with a suspension of said *Agrobacterium* strain, said suspension having a concentration of cells of said *Agrobacterium* strain corresponding to a calculated optical density at 600 nm of at most 0.04, preferably at most 0.01, more preferably at most 0.004, and most preferably at most 0.001,
whereby said calculated optical densities are defined by an at least 25-fold, preferably an at least 100-fold, more preferably an at least 250-fold, and most preferably an at least 1000-fold dilution, respectively, of a suspension of *Agrobacteria* of an OD at 600 nm of 1.0.

30. The process according to claim 1, wherein said plant or said plant leaves belongs to one of the following species: *Nicotiana benthamiana, Nicotiana tabacum, Petunia hybrida, Brassica campestris, B. juncea,* cress, arugula, mustard, Strawberry spinach, *Chenopodium capitatum,* lettuce, sunflower, and cucumber.

31. The process according to claim 1, wherein said transfecting is performed by infiltrating said plant or said plant leaves.

32. A process of producing a protein of interest by expressing a sequence of interest in a plant or in plant leaves, comprising:
(a) transfecting said plant or said plant leaves with an *Agrobacterium* strain in the presence or in the absence of a complementing factor, said *Agrobacterium* strain containing in T-DNA a heterologous DNA sequence having a sequence portion encoding a replicon,
wherein said sequence encoding an RNA replicon contains
(i) sequences necessary for replicon function of said RNA replicon, said sequences being derived from a plant virus, and
(ii) said sequence of interest to be expressed,
(b) optionally isolating said protein of interest from said plant or said plant leaves infiltrated in step (a),
wherein said *Agrobacterium* strain is provided with a first genetic modification rendering said *Agrobacterium* strain defective for transfecting organisms with said T-DNA in the absence of said complementing factor,
wherein said sequences necessary for replicon function exhibit at selected localities function-conservative differences from said plant RNA virus, said differences causing an increased frequency of replicon formation compared to an RNA replicon not exhibiting said differences, and
wherein said plant or said plant leaves are infiltrated in step (a) with a suspension of said *Agrobacterium* strain, said suspension having a concentration of cells of said *Agrobacterium* strain corresponding to a calculated optical density at 600 nm of at most 0.04.

33. A process of producing a protein of interest by expressing a sequence of interest in a plant or in plant leaves, comprising:
(a) transfecting said plant or said plant leaves with an *Agrobacterium* strain in the presence or in the absence of a complementing factor, said *Agrobacterium* strain containing in T-DNA a heterologous DNA sequence having a sequence portion encoding a replicon,
wherein said sequence encoding an RNA replicon contains
(i) sequences necessary for replicon function of said RNA replicon, said sequences being derived from a plant virus, and
(ii) said sequence of interest to be expressed,
(b) optionally isolating said protein of interest from said plant or said plant leaves infiltrated in step (a),
wherein said *Agrobacterium* strain is provided with a first genetic modification rendering said *Agrobacterium* strain defective for transfecting organisms with said T-DNA in the absence of said complementing factor and wherein said sequences necessary for replicon function contain one or more nuclear introns, and
wherein said plant or said plant leaves are infiltrated in step (a) with a suspension of said *Agrobacterium* strain, said suspension having a concentration of cells of said *Agrobacterium* strain corresponding to a calculated optical density at 600 nm of at most 0.04.

34. A process of producing a protein of interest by expressing a sequence of interest in a plant or in plant leaves, comprising:
(a) transfecting said plant or said plant leaves with an *Agrobacterium* strain in the presence or in the absence of a complementing factor, said *Agrobacterium* strain containing in T-DNA a heterologous DNA sequence having a sequence portion encoding a replicon, wherein said sequence encoding an RNA replicon contains
(i) sequences necessary for replicon function of said RNA replicon, said sequences being derived from a plant virus, and
(ii) said sequence of interest to be expressed,
(b) optionally isolating said protein of interest from said plant or said plant leaves infiltrated in step (a),
wherein said *Agrobacterium* strain is provided with a first genetic modification rendering said *Agrobacterium* strain defective in a function required for introducing said T-DNA in cells of said plant or plant leaves in the absence of said complementing factor, wherein said *Agrobacterium* strain has a further genetic modification that renders said *Agrobacterium* strain defective for conjugative transfer of plasmid DNA to other bacteria, and
wherein said plant or said plant leaves are infiltrated in step (a) with a suspension of said *Agrobacterium* strain, said suspension having a concentration of cells of said *Agrobacterium* strain corresponding to a calculated optical density at 600 nm of at most 0.04.

35. A process of producing a protein of interest by expressing a sequence of interest in a plant or in plant leaves, comprising:
(a) transfecting said plant or said plant leaves with an *Agrobacterium* strain in the presence or in the absence of a complementing factor, said *Agrobacterium* strain containing in T-DNA a heterologous DNA sequence having a sequence portion encoding a replicon,
wherein said sequence encoding an RNA replicon contains
(i) sequences necessary for replicon function of said RNA replicon, said sequences being derived from a plant virus, and
(ii) said sequence of interest to be expressed,
(b) optionally isolating said protein of interest from said plant or said plant leaves infiltrated in step (a),
wherein said *Agrobacterium* strain is provided with a first genetic modification rendering said *Agrobacterium* strain defective in a function required for introducing said T-DNA in cells of said plant or plant leaves in the absence of said complementing factor,
wherein said *Agrobacterium* strain is auxotrophic for an essential metabolite required for auxotrophic growth of said *Agrobacterium* strain, and
wherein said plant or said plant leaves are infiltrated in step (a) with a suspension of said *Agrobacterium* strain, said suspension having a concentration of cells of said *Agrobacterium* strain corresponding to a calculated optical density at 600 nm of at most 0.04.

36. A process of producing a protein of interest by expressing a sequence of interest in a plant or in plant leaves, comprising:
(a) transfecting said plant or said plant leaves with an *Agrobacterium* strain in the presence or in the absence of a complementing factor, said *Agrobacterium* strain containing in T-DNA a heterologous DNA sequence having a sequence portion encoding a replicon,
wherein said sequence encoding an RNA replicon contains
(i) sequences necessary for replicon function of said RNA replicon, said sequences being derived from a plant virus, and
(ii) said sequence of interest to be expressed,
(b) optionally isolating said protein of interest from said plant or said plant leaves infiltrated in step (a),
wherein
said *Agrobacterium* strain is provided with a first genetic modification rendering said *Agrobacterium* strain defective in a function required for introducing said T-DNA in cells of said plant or plant leaves in the absence of said complementing factor,
said *Agrobacterium* strain is auxotrophic for an essential metabolite required for auxotrophic growth of said *Agrobacterium* strain,
said sequences necessary for replicon function contain one or more nuclear introns, and
wherein said plant or said plant leaves are infiltrated in step (a) with a suspension of said *Agrobacterium* strain, said suspension having a concentration of cells of said *Agrobacterium* strain corresponding to a calculated optical density at 600 nm of at most 0.04.

* * * * *